US012144940B2

(12) United States Patent
Chou et al.

(10) Patent No.: US 12,144,940 B2
(45) Date of Patent: Nov. 19, 2024

(54) ASPIRATION CATHETER SYSTEMS AND METHODS OF USE

(71) Applicant: Route 92 Medical, Inc., San Mateo, CA (US)

(72) Inventors: Tony M. Chou, San Mateo, CA (US); Joey English, San Mateo, CA (US); Warren T. Kim, San Mateo, CA (US); Ian J. Clark, San Rafael, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 0 days.

(21) Appl. No.: 18/297,450

(22) Filed: Apr. 7, 2023

(65) Prior Publication Data

US 2023/0263995 A1 Aug. 24, 2023

Related U.S. Application Data

(63) Continuation of application No. 17/497,713, filed on Oct. 8, 2021.

(Continued)

(51) Int. Cl.
| | |
|---|---|
| *A61M 25/01* | (2006.01) |
| *A61B 17/12* | (2006.01) |
| *A61M 25/09* | (2006.01) |

(52) U.S. Cl.
CPC ... *A61M 25/0133* (2013.01); *A61B 17/12109* (2013.01); *A61M 25/0108* (2013.01); *A61M 25/09* (2013.01)

(58) Field of Classification Search
CPC ...... A61M 1/76; A61M 1/81; A61M 25/0662; A61M 2025/0004; A61M 2025/0006;

(Continued)

(56) References Cited

U.S. PATENT DOCUMENTS

| | | | |
|---|---|---|---|
| 2,623,520 | A | 12/1952 | Bamford, Jr. et al. |
| 2,730,101 | A | 1/1956 | Hoffman |

(Continued)

FOREIGN PATENT DOCUMENTS

| | | |
|---|---|---|
| CN | 101121055 A | 2/2008 |
| CN | 101588835 A | 11/2009 |

(Continued)

OTHER PUBLICATIONS

"2007 International Stroke Conference: Abstracts." Stroke, vol. 38, No. 2, 2007, pp. 454-607. Web. Downloaded Jun. 13, 2017.

(Continued)

*Primary Examiner* — Tiffany Legette
(74) *Attorney, Agent, or Firm* — Mintz Levin Cohn Ferris Glovsky and Popeo, P.C.

(57) ABSTRACT

Systems and methods are described for removing an embolus in a cerebral vessel of a patient. The assembled system of devices includes a catheter having a catheter lumen and a distal end and a catheter advancement element extending through the catheter lumen. A tapered distal end region of the catheter advancement element extends distal to the distal end of the catheter. The assembled system of devices is advanced together towards an occlusion site in a cerebral vessel of a patient visible on angiogram. The occlusion site includes an angiographic limit of contrast and an embolus downstream of the angiographic limit of contrast. The catheter advancement element is advanced to a location past the angiographic limit of contrast without crossing the embolus. The catheter is advanced to position the distal end of the catheter at a treatment site located past the angiographic limit of contrast and aspiration applied.

27 Claims, 24 Drawing Sheets

Related U.S. Application Data

(60) Provisional application No. 63/089,987, filed on Oct. 9, 2020.

(58) Field of Classification Search
CPC .......... A61M 25/0133; A61M 25/0108; A61B 2017/22072; A61B 2017/22074; A61B 2017/22079; A61B 17/12109; A61B 17/22

See application file for complete search history.

(56) References Cited

U.S. PATENT DOCUMENTS

| | | |
|---|---|---|
| 3,612,050 A | 10/1971 | Sheridan |
| 3,631,848 A | 1/1972 | Muller |
| 3,949,757 A | 4/1976 | Sabel |
| 3,996,938 A | 12/1976 | Clark, III |
| 4,013,080 A | 3/1977 | Froning |
| 4,020,829 A | 5/1977 | Willson et al. |
| 4,033,331 A | 7/1977 | Guss et al. |
| 4,174,715 A | 11/1979 | Hasson |
| 4,319,580 A | 3/1982 | Colley et al. |
| 4,323,071 A | 4/1982 | Simpson et al. |
| 4,406,656 A | 9/1983 | Hattler et al. |
| 4,571,240 A | 2/1986 | Samson et al. |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,762,128 A | 8/1988 | Rosenbluth |
| 4,771,777 A | 9/1988 | Horzewski et al. |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,840,690 A | 6/1989 | Melinyshyn et al. |
| 4,863,431 A | 9/1989 | Vaillancourt |
| 4,865,581 A | 9/1989 | Lundquist et al. |
| 4,873,978 A | 10/1989 | Ginsburg |
| 4,873,979 A | 10/1989 | Hanna |
| 4,883,460 A | 11/1989 | Zanetti |
| 4,887,613 A | 12/1989 | Farr et al. |
| 4,898,575 A | 2/1990 | Fischell et al. |
| 4,900,303 A | 2/1990 | Lemelson |
| 4,921,478 A | 5/1990 | Solano et al. |
| 4,921,479 A | 5/1990 | Grayze |
| 4,921,484 A | 5/1990 | Hillstead |
| 4,923,462 A | 5/1990 | Stevens |
| 4,946,440 A | 8/1990 | Hall |
| 4,946,443 A | 8/1990 | Hauser et al. |
| 4,994,033 A | 2/1991 | Shockey et al. |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,103,827 A | 4/1992 | Smith |
| 5,108,419 A | 4/1992 | Reger et al. |
| 5,135,484 A | 8/1992 | Wright |
| 5,152,277 A | 10/1992 | Honda et al. |
| 5,161,534 A | 11/1992 | Berthiaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,207,648 A | 5/1993 | Gross |
| 5,211,651 A | 5/1993 | Reger et al. |
| 5,217,705 A | 6/1993 | Reno et al. |
| 5,219,332 A | 6/1993 | Nelson et al. |
| 5,243,997 A | 9/1993 | Uflacker et al. |
| 5,250,060 A | 10/1993 | Carbo et al. |
| 5,257,979 A | 11/1993 | Jagpal |
| 5,267,960 A | 12/1993 | Hayman et al. |
| 5,269,297 A | 12/1993 | Weng et al. |
| 5,303,714 A | 4/1994 | Abele et al. |
| 5,308,318 A | 5/1994 | Plassche, Jr. |
| 5,312,338 A | 5/1994 | Nelson et al. |
| 5,312,356 A | 5/1994 | Engelson et al. |
| RE34,633 E | 6/1994 | Sos et al. |
| 5,318,032 A | 6/1994 | Lonsbury et al. |
| 5,324,262 A | 6/1994 | Fischell et al. |
| 5,325,868 A | 7/1994 | Kimmelstiel |
| 5,328,471 A | 7/1994 | Slepian |
| 5,338,300 A | 8/1994 | Cox |
| 5,352,197 A | 10/1994 | Hammersmark et al. |
| 5,364,358 A | 11/1994 | Hewitt et al. |
| 5,370,623 A | 12/1994 | Kreamer |
| 5,380,284 A | 1/1995 | Don Michael |
| 5,385,562 A | 1/1995 | Adams et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,429,605 A | 7/1995 | Richling et al. |
| 5,437,632 A | 8/1995 | Engelson |
| 5,438,993 A | 8/1995 | Lynch et al. |
| 5,441,051 A | 8/1995 | Hileman et al. |
| 5,443,454 A | 8/1995 | Tanabe et al. |
| 5,454,795 A | 10/1995 | Samson |
| 5,465,716 A | 11/1995 | Avitall |
| 5,466,222 A | 11/1995 | Ressemann et al. |
| 5,476,450 A | 12/1995 | Ruggio |
| 5,484,407 A | 1/1996 | Osypka |
| 5,484,412 A | 1/1996 | Pierpont |
| 5,484,418 A | 1/1996 | Quiachon et al. |
| 5,485,667 A | 1/1996 | Kleshinski |
| 5,490,859 A | 2/1996 | Mische et al. |
| 5,492,530 A | 2/1996 | Fischell et al. |
| 5,496,294 A | 3/1996 | Hergenrother et al. |
| 5,499,975 A | 3/1996 | Cope et al. |
| 5,501,694 A | 3/1996 | Ressemann et al. |
| 5,522,836 A | 6/1996 | Palermo |
| 5,527,292 A | 6/1996 | Adams et al. |
| 5,533,967 A | 7/1996 | Imran |
| 5,538,512 A | 7/1996 | Zenzon et al. |
| 5,542,936 A | 8/1996 | Razi |
| 5,542,937 A | 8/1996 | Chee et al. |
| 5,546,958 A | 8/1996 | Thorud et al. |
| 5,549,119 A | 8/1996 | Solar |
| 5,549,601 A | 8/1996 | McIntyre et al. |
| 5,549,626 A | 8/1996 | Miller et al. |
| 5,558,635 A | 9/1996 | Cannon |
| 5,571,122 A | 11/1996 | Kelly et al. |
| 5,573,520 A | 11/1996 | Schwartz et al. |
| 5,578,009 A | 11/1996 | Kraus et al. |
| 5,591,194 A | 1/1997 | Berthiaume |
| 5,599,307 A | 2/1997 | Bacher et al. |
| 5,599,326 A | 2/1997 | Carter |
| 5,603,698 A | 2/1997 | Roberts et al. |
| 5,628,754 A | 5/1997 | Shevlin et al. |
| 5,643,254 A | 7/1997 | Scheldrup et al. |
| 5,658,263 A | 8/1997 | Dang et al. |
| 5,658,264 A | 8/1997 | Samson |
| 5,658,309 A | 8/1997 | Berthiaume et al. |
| 5,662,622 A | 9/1997 | Gore et al. |
| 5,667,499 A | 9/1997 | Welch et al. |
| 5,676,659 A | 10/1997 | McGurk |
| 5,682,894 A | 11/1997 | Orr et al. |
| 5,693,029 A | 12/1997 | Leonhardt |
| 5,695,483 A | 12/1997 | Samson |
| 5,702,373 A | 12/1997 | Samson |
| 5,702,439 A | 12/1997 | Keith et al. |
| 5,707,376 A | 1/1998 | Kavteladze et al. |
| 5,720,764 A | 2/1998 | Naderlinger |
| 5,730,734 A | 3/1998 | Adams et al. |
| 5,749,849 A | 5/1998 | Engelson |
| 5,749,858 A | 5/1998 | Cramer |
| 5,766,191 A | 6/1998 | Trerotola |

(56) References Cited

U.S. PATENT DOCUMENTS

| | | |
|---|---|---|
| 5,776,141 A | 7/1998 | Klein et al. |
| 5,776,142 A | 7/1998 | Gunderson |
| 5,794,629 A | 8/1998 | Frazee |
| 5,795,341 A | 8/1998 | Samson |
| 5,810,869 A | 9/1998 | Kaplan et al. |
| 5,810,874 A | 9/1998 | Lefebvre |
| 5,814,064 A | 9/1998 | Daniel et al. |
| 5,817,101 A | 10/1998 | Fiedler |
| 5,827,229 A | 10/1998 | Auth et al. |
| 5,827,242 A | 10/1998 | Follmer et al. |
| 5,833,650 A | 11/1998 | Imran |
| 5,836,868 A | 11/1998 | Ressemann et al. |
| 5,836,926 A | 11/1998 | Peterson et al. |
| 5,836,955 A | 11/1998 | Buelna et al. |
| 5,843,002 A | 12/1998 | Pecor et al. |
| 5,843,051 A | 12/1998 | Adams et al. |
| 5,843,103 A | 12/1998 | Wulfman |
| 5,846,251 A | 12/1998 | Hart |
| 5,851,189 A | 12/1998 | Forber |
| 5,851,210 A | 12/1998 | Torossian |
| 5,853,400 A | 12/1998 | Samson |
| 5,876,367 A | 3/1999 | Kaganov et al. |
| 5,876,375 A | 3/1999 | Penny |
| 5,876,386 A | 3/1999 | Samson |
| 5,882,329 A | 3/1999 | Patterson et al. |
| 5,882,334 A | 3/1999 | Sepetka et al. |
| 5,885,209 A | 3/1999 | Green |
| 5,891,114 A | 4/1999 | Chien et al. |
| 5,895,399 A | 4/1999 | Barbut et al. |
| 5,897,567 A | 4/1999 | Ressemann et al. |
| 5,899,890 A | 5/1999 | Chiang et al. |
| 5,899,892 A | 5/1999 | Mortier et al. |
| 5,908,407 A | 6/1999 | Frazee et al. |
| 5,910,154 A | 6/1999 | Tsugita et al. |
| 5,911,725 A | 6/1999 | Boury |
| 5,911,734 A | 6/1999 | Tsugita et al. |
| 5,913,848 A | 6/1999 | Luther et al. |
| 5,916,192 A | 6/1999 | Nita et al. |
| 5,916,208 A | 6/1999 | Luther et al. |
| 5,921,952 A | 7/1999 | Desmond, III et al. |
| 5,928,192 A | 7/1999 | Maahs |
| 5,928,260 A | 7/1999 | Chin et al. |
| 5,935,122 A | 8/1999 | Fourkas et al. |
| 5,935,139 A | 8/1999 | Bates |
| 5,938,645 A | 8/1999 | Gordon |
| 5,941,869 A | 8/1999 | Patterson et al. |
| 5,957,882 A | 9/1999 | Nita et al. |
| 5,972,019 A | 10/1999 | Engelson et al. |
| 5,976,093 A | 11/1999 | Jang |
| 5,976,178 A | 11/1999 | Goldsteen et al. |
| 5,997,508 A | 12/1999 | Lunn et al. |
| 5,997,523 A | 12/1999 | Jang |
| 5,997,557 A | 12/1999 | Barbut et al. |
| 6,004,310 A | 12/1999 | Bardsley et al. |
| 6,007,530 A | 12/1999 | Dornhofer et al. |
| 6,010,522 A | 1/2000 | Barbut et al. |
| 6,013,085 A | 1/2000 | Howard |
| 6,022,336 A | 2/2000 | Zadno-Azizi et al. |
| 6,022,340 A | 2/2000 | Sepetka et al. |
| 6,030,349 A | 2/2000 | Wilson et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,066,149 A | 5/2000 | Samson et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,090,118 A | 7/2000 | McGuckin, Jr. |
| 6,106,530 A | 8/2000 | Harada |
| 6,110,139 A | 8/2000 | Loubser |
| 6,117,141 A | 9/2000 | Ouchi |
| 6,120,480 A | 9/2000 | Zhang et al. |
| 6,135,991 A | 10/2000 | Muni et al. |
| 6,139,524 A | 10/2000 | Killion |
| 6,142,958 A | 11/2000 | Hammarstrom et al. |
| 6,142,987 A | 11/2000 | Tsugita |
| 6,146,370 A | 11/2000 | Barbut |
| 6,146,373 A | 11/2000 | Cragg et al. |
| 6,146,396 A | 11/2000 | Konya et al. |
| 6,146,415 A | 11/2000 | Fitz |
| 6,152,909 A | 11/2000 | Bagaoisan et al. |
| 6,152,912 A | 11/2000 | Jansen et al. |
| 6,156,005 A | 12/2000 | Theron |
| 6,159,195 A | 12/2000 | Ha et al. |
| 6,159,230 A | 12/2000 | Samuels |
| 6,161,547 A | 12/2000 | Barbut |
| 6,165,163 A | 12/2000 | Chien et al. |
| 6,165,167 A | 12/2000 | Delaloye |
| 6,165,199 A | 12/2000 | Barbut |
| 6,168,579 B1 | 1/2001 | Tsugita |
| 6,171,295 B1 | 1/2001 | Garabedian et al. |
| 6,176,844 B1 | 1/2001 | Lee |
| 6,197,016 B1 | 3/2001 | Fourkas et al. |
| 6,203,561 B1 | 3/2001 | Ramee et al. |
| 6,206,868 B1 | 3/2001 | Parodi |
| 6,210,370 B1 | 4/2001 | Chi-Sing et al. |
| 6,221,038 B1 | 4/2001 | Brisken |
| 6,221,049 B1 | 4/2001 | Selmon et al. |
| 6,228,046 B1 | 5/2001 | Brisken |
| 6,228,052 B1 | 5/2001 | Pohndorf |
| 6,234,971 B1 | 5/2001 | Jang |
| 6,238,402 B1 | 5/2001 | Sullivan, III et al. |
| 6,238,412 B1 | 5/2001 | Dubrul et al. |
| 6,238,430 B1 | 5/2001 | Klumb et al. |
| 6,240,231 B1 | 5/2001 | Ferrera et al. |
| 6,254,628 B1 | 7/2001 | Wallace et al. |
| 6,258,052 B1 | 7/2001 | Milo |
| 6,258,080 B1 | 7/2001 | Samson |
| 6,258,115 B1 | 7/2001 | Dubrul |
| 6,270,477 B1 | 8/2001 | Bagaoisan et al. |
| 6,277,115 B1 | 8/2001 | Saadat |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,309,379 B1 | 10/2001 | Willard et al. |
| 6,346,116 B1 | 2/2002 | Brooks et al. |
| 6,355,027 B1 | 3/2002 | Le et al. |
| 6,361,545 B1 | 3/2002 | Macoviak et al. |
| 6,364,894 B1 | 4/2002 | Healy et al. |
| 6,364,900 B1 | 4/2002 | Heuser |
| 6,368,316 B1 | 4/2002 | Jansen et al. |
| 6,368,338 B1 | 4/2002 | Konya et al. |
| 6,368,344 B1 | 4/2002 | Fitz |
| 6,368,355 B1 | 4/2002 | Uflacker |
| 6,379,325 B1 | 4/2002 | Benett et al. |
| 6,383,172 B1 | 5/2002 | Barbut |
| 6,391,044 B1 | 5/2002 | Yadav et al. |
| 6,394,976 B1 | 5/2002 | Winston et al. |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,451,005 B1 | 9/2002 | Saitou et al. |
| 6,454,741 B1 | 9/2002 | Muni et al. |
| 6,454,775 B1 | 9/2002 | Demarais et al. |
| 6,458,151 B1 | 10/2002 | Saltiel |
| 6,464,664 B1 | 10/2002 | Jonkman et al. |
| 6,468,219 B1 | 10/2002 | Njemanze |
| 6,475,195 B1 | 11/2002 | Voda |
| 6,475,244 B2 | 11/2002 | Herweck et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,485,466 B2 | 11/2002 | Hamilton |
| 6,485,500 B1 | 11/2002 | Kokish et al. |
| 6,485,501 B1 | 11/2002 | Green |

(56) References Cited

U.S. PATENT DOCUMENTS

| | | |
|---|---|---|
| 6,508,824 B1 | 1/2003 | Flaherty et al. |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,517,520 B2 | 2/2003 | Chang et al. |
| 6,524,303 B1 | 2/2003 | Garibaldi |
| 6,527,746 B1 | 3/2003 | Oslund et al. |
| 6,533,800 B1 | 3/2003 | Barbut |
| 6,537,241 B1 | 3/2003 | Odland |
| 6,537,295 B2 | 3/2003 | Petersen |
| 6,540,712 B1 | 4/2003 | Parodi et al. |
| 6,540,768 B1 | 4/2003 | Diaz et al. |
| 6,544,276 B1 | 4/2003 | Azizi |
| 6,549,800 B1 | 4/2003 | Atalar et al. |
| 6,551,268 B1 | 4/2003 | Kaganov et al. |
| 6,551,273 B1 | 4/2003 | Olson et al. |
| 6,551,302 B1 | 4/2003 | Rosinko et al. |
| 6,554,820 B1 | 4/2003 | Wendlandt et al. |
| 6,554,827 B2 | 4/2003 | Chandrasekaran et al. |
| 6,555,057 B1 | 4/2003 | Barbut et al. |
| 6,558,377 B2 | 5/2003 | Lee et al. |
| 6,558,405 B1 | 5/2003 | McInnes |
| 6,562,049 B1 | 5/2003 | Norlander et al. |
| 6,562,052 B2 | 5/2003 | Nobles et al. |
| 6,569,148 B2 | 5/2003 | Bagaoisan et al. |
| 6,579,246 B2 | 6/2003 | Jacobsen et al. |
| 6,579,260 B2 | 6/2003 | Maki et al. |
| 6,579,264 B1 | 6/2003 | Rossi |
| 6,579,484 B1 | 6/2003 | Tiernan et al. |
| 6,582,390 B1 | 6/2003 | Sanderson |
| 6,582,396 B1 | 6/2003 | Parodi |
| 6,582,440 B1 | 6/2003 | Brumbach |
| 6,582,448 B1 | 6/2003 | Boyle et al. |
| 6,589,262 B1 | 7/2003 | Honebrink et al. |
| 6,592,616 B1 | 7/2003 | Stack et al. |
| 6,595,953 B1 | 7/2003 | Coppi et al. |
| 6,595,980 B1 | 7/2003 | Barbut |
| 6,596,011 B2 | 7/2003 | Johnson et al. |
| 6,605,074 B2 | 8/2003 | Zadno-Azizi et al. |
| 6,610,077 B1 | 8/2003 | Hancock et al. |
| 6,612,999 B2 | 9/2003 | Brennan et al. |
| 6,616,681 B2 | 9/2003 | Hanson et al. |
| 6,620,148 B1 | 9/2003 | Tsugita |
| 6,622,367 B1 | 9/2003 | Bolduc et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,673,025 B1 | 1/2004 | Richardson et al. |
| 6,676,637 B1 | 1/2004 | Bonnette et al. |
| 6,679,893 B1 | 1/2004 | Tran |
| 6,682,505 B2 | 1/2004 | Bates et al. |
| 6,685,672 B1 | 2/2004 | Forman |
| 6,685,722 B1 | 2/2004 | Rosenbluth et al. |
| 6,689,144 B2 | 2/2004 | Gerberding |
| 6,692,473 B2 | 2/2004 | St. Cyr et al. |
| 6,695,858 B1 | 2/2004 | Dubrul et al. |
| 6,695,865 B2 | 2/2004 | Boyle et al. |
| 6,702,782 B2 | 3/2004 | Miller et al. |
| 6,702,834 B1 | 3/2004 | Boylan et al. |
| 6,706,055 B2 | 3/2004 | Douk et al. |
| 6,711,436 B1 | 3/2004 | Duhaylongsod |
| 6,716,183 B2 | 4/2004 | Clayman et al. |
| 6,719,717 B1 | 4/2004 | Johnson et al. |
| 6,723,064 B2 | 4/2004 | Babaev |
| 6,726,675 B1 | 4/2004 | Beyar |
| 6,730,104 B1 | 5/2004 | Sepetka et al. |
| 6,733,517 B1 | 5/2004 | Collins |
| 6,740,104 B1 | 5/2004 | Solar et al. |
| 6,749,627 B2 | 6/2004 | Thompson et al. |
| 6,755,803 B1 | 6/2004 | Le et al. |
| 6,755,812 B2 | 6/2004 | Peterson et al. |
| 6,755,847 B2 | 6/2004 | Eskuri |
| 6,758,854 B1 | 7/2004 | Butler et al. |
| 6,761,708 B1 | 7/2004 | Chiu et al. |
| 6,764,464 B2 | 7/2004 | McGuckin, Jr. et al. |
| 6,773,448 B2 | 8/2004 | Kusleika et al. |
| 6,790,204 B2 | 9/2004 | Zadno-Azizi et al. |
| 6,805,684 B2 | 10/2004 | Bonnette et al. |
| 6,805,692 B2 | 10/2004 | Muni et al. |
| 6,824,545 B2 | 11/2004 | Sepetka et al. |
| 6,824,550 B1 | 11/2004 | Noriega et al. |
| 6,824,553 B1 | 11/2004 | Samson et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,911,036 B2 | 6/2005 | Douk et al. |
| 6,926,658 B2 | 8/2005 | Farnan |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zadno-Azizi |
| 6,960,189 B2 | 11/2005 | Bates et al. |
| 6,969,395 B2 | 11/2005 | Eskuri |
| 6,972,030 B2 | 12/2005 | Lee et al. |
| 6,977,068 B1 | 12/2005 | Nair et al. |
| 6,991,642 B2 | 1/2006 | Petersen |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,325 B1 | 4/2006 | Sullivan |
| 7,033,336 B2 | 4/2006 | Hogendijk |
| 7,033,344 B2 | 4/2006 | Imran |
| 7,037,267 B1 | 5/2006 | Lipson et al. |
| 7,048,758 B2 | 5/2006 | Boyle et al. |
| 7,052,500 B2 | 5/2006 | Bashiri et al. |
| 7,056,328 B2 | 6/2006 | Arnott |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,115,134 B2 | 10/2006 | Chambers |
| 7,115,138 B2 | 10/2006 | Renati et al. |
| 7,118,539 B2 | 10/2006 | Vrba et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,166,120 B2 | 1/2007 | Kusleika |
| 7,169,165 B2 | 1/2007 | Belef et al. |
| 7,172,621 B2 | 2/2007 | Theron |
| 7,220,271 B2 | 5/2007 | Clubb et al. |
| 7,223,253 B2 | 5/2007 | Hogendijk |
| 7,229,431 B2 | 6/2007 | Houser et al. |
| 7,229,463 B2 | 6/2007 | Sutton et al. |
| 7,229,464 B2 | 6/2007 | Hanson et al. |

(56) References Cited

U.S. PATENT DOCUMENTS

| | | |
|---|---|---|
| 7,232,452 B2 | 6/2007 | Adams et al. |
| 7,235,061 B2 | 6/2007 | Tsugita |
| 7,242,977 B2 | 7/2007 | Partridge et al. |
| 7,250,042 B2 | 7/2007 | Kataishi et al. |
| 7,285,126 B2 | 10/2007 | Sepetka et al. |
| 7,306,585 B2 | 12/2007 | Ross |
| 7,309,334 B2 | 12/2007 | von Hoffmann |
| 7,316,678 B2 | 1/2008 | Nash et al. |
| 7,329,278 B2 | 2/2008 | Seguin et al. |
| 7,367,982 B2 | 5/2008 | Nash et al. |
| 7,374,560 B2 | 5/2008 | Ressemann et al. |
| 7,374,561 B2 | 5/2008 | Barbut |
| 7,374,564 B2 | 5/2008 | Brown |
| 7,381,200 B2 | 6/2008 | Katoh et al. |
| 7,384,412 B2 | 6/2008 | Coppi |
| 7,402,151 B2 | 7/2008 | Rosenman et al. |
| 7,422,579 B2 | 9/2008 | Wahr et al. |
| 7,449,010 B1 | 11/2008 | Hayase et al. |
| 7,458,980 B2 | 12/2008 | Barbut |
| 7,476,232 B2 | 1/2009 | Deal |
| 7,497,844 B2 | 3/2009 | Spear et al. |
| 7,507,229 B2 | 3/2009 | Hewitt et al. |
| 7,524,303 B1 | 4/2009 | Don Michael et al. |
| 7,534,250 B2 | 5/2009 | Schaeffer et al. |
| 7,537,568 B2 | 5/2009 | Moehring |
| 7,549,974 B2 | 6/2009 | Nayak |
| 7,558,622 B2 | 7/2009 | Tran |
| 7,604,612 B2 | 10/2009 | Ressemann et al. |
| 7,615,042 B2 | 11/2009 | Beyar et al. |
| 7,625,207 B2 | 12/2009 | Hershey et al. |
| 7,691,121 B2 * | 4/2010 | Rosenbluth .......... A61B 17/221 604/523 |
| 7,717,934 B2 | 5/2010 | Kusleika |
| 7,731,683 B2 | 6/2010 | Jang et al. |
| 7,736,355 B2 | 6/2010 | Itou et al. |
| 7,766,049 B2 | 8/2010 | Miller et al. |
| 7,766,820 B2 | 8/2010 | Core |
| 7,771,358 B2 | 8/2010 | Moehring et al. |
| 7,785,286 B2 | 8/2010 | Magnin et al. |
| 7,803,136 B2 | 9/2010 | Schatz |
| 7,806,906 B2 | 10/2010 | Don Michael |
| 7,815,626 B1 | 10/2010 | McFadden et al. |
| 7,837,692 B2 | 11/2010 | Mulholland et al. |
| 7,842,055 B2 | 11/2010 | Pintor et al. |
| 7,842,065 B2 | 11/2010 | Belef et al. |
| 7,850,642 B2 | 12/2010 | Moll et al. |
| 7,850,654 B2 | 12/2010 | Belhe et al. |
| 7,854,746 B2 | 12/2010 | Dorn et al. |
| 7,867,216 B2 | 1/2011 | Wahr et al. |
| 7,879,062 B2 | 2/2011 | Galdonik et al. |
| 7,905,856 B2 | 3/2011 | McGuckin, Jr. et al. |
| 7,905,877 B1 | 3/2011 | Jimenez et al. |
| 7,905,891 B2 | 3/2011 | Self |
| 7,909,812 B2 | 3/2011 | Jansen et al. |
| 7,927,309 B2 | 4/2011 | Palm |
| 7,927,347 B2 | 4/2011 | Hogendijk et al. |
| 7,931,659 B2 | 4/2011 | Bose et al. |
| 7,938,820 B2 | 5/2011 | Webster et al. |
| 7,967,789 B2 | 6/2011 | Solar et al. |
| 7,972,294 B2 | 7/2011 | Nash et al. |
| 7,972,298 B2 | 7/2011 | Wallace et al. |
| 7,972,308 B2 | 7/2011 | Putz |
| 7,988,646 B2 | 8/2011 | Taber |
| 7,998,104 B2 | 8/2011 | Chang |
| 8,021,351 B2 | 9/2011 | Boldenow et al. |
| 8,029,533 B2 | 10/2011 | Bagaoisan et al. |
| 8,043,279 B2 | 10/2011 | Hisamatsu et al. |
| 8,048,032 B2 | 11/2011 | Root et al. |
| 8,052,636 B2 | 11/2011 | Moll et al. |
| 8,052,640 B2 | 11/2011 | Fiorella et al. |
| 8,066,757 B2 | 11/2011 | Ferrera et al. |
| 8,070,694 B2 | 12/2011 | Galdonik et al. |
| 8,084,246 B2 | 12/2011 | Hoon et al. |
| 8,092,483 B2 | 1/2012 | Galdonik et al. |
| 8,114,032 B2 | 2/2012 | Ferry et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,172,831 B2 | 5/2012 | Webler, Jr. |
| 8,181,324 B2 | 5/2012 | McFadden et al. |
| 8,211,023 B2 | 7/2012 | Swan et al. |
| 8,221,348 B2 | 7/2012 | Hackett et al. |
| 8,231,600 B2 | 7/2012 | von Hoffmann |
| 8,235,968 B2 | 8/2012 | Tremaglio |
| 8,251,978 B2 | 8/2012 | Nash et al. |
| 8,252,010 B1 | 8/2012 | Raju et al. |
| 8,252,014 B2 | 8/2012 | Fisher |
| 8,257,302 B2 | 9/2012 | Beyar et al. |
| 8,292,850 B2 | 10/2012 | Root et al. |
| 8,308,712 B2 | 11/2012 | Provost et al. |
| 8,343,089 B2 | 1/2013 | Chang |
| 8,361,105 B2 | 1/2013 | Adams et al. |
| 8,366,735 B2 | 2/2013 | Bose et al. |
| 8,414,516 B2 | 4/2013 | Chang |
| 8,419,786 B2 | 4/2013 | Cottone, Jr. et al. |
| 8,425,549 B2 | 4/2013 | Lenker et al. |
| 8,460,312 B2 | 6/2013 | Bose et al. |
| 8,465,456 B2 | 6/2013 | Stivland |
| 8,523,801 B2 | 9/2013 | Nash et al. |
| 8,535,272 B2 | 9/2013 | Wang et al. |
| 8,540,759 B2 | 9/2013 | Porter |
| 8,545,552 B2 | 10/2013 | Garrison et al. |
| 8,574,245 B2 | 11/2013 | Garrison et al. |
| 8,600,477 B2 | 12/2013 | Beyar et al. |
| 8,609,426 B2 | 12/2013 | Silver |
| 8,636,714 B2 | 1/2014 | McFerran |
| 8,663,259 B2 | 3/2014 | Levine et al. |
| 8,682,411 B2 | 3/2014 | Kassab et al. |
| 8,690,907 B1 | 4/2014 | Janardhan et al. |
| 8,702,680 B2 | 4/2014 | Jimenez et al. |
| 8,708,954 B2 | 4/2014 | Webler |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,764,813 B2 | 7/2014 | Jantzen et al. |
| 8,795,305 B2 | 8/2014 | Martin et al. |
| 8,801,670 B2 | 8/2014 | Drontle et al. |
| 8,801,749 B2 | 8/2014 | Adams et al. |
| 8,814,892 B2 | 8/2014 | Galdonik et al. |
| 8,870,805 B2 | 10/2014 | Chang |
| 8,876,776 B2 | 11/2014 | Kassab et al. |
| 8,932,286 B2 | 1/2015 | Terry et al. |
| 8,932,320 B1 | 1/2015 | Janardhan et al. |
| RE45,380 E | 2/2015 | Root et al. |
| 8,961,533 B2 | 2/2015 | Stahler et al. |
| 8,961,549 B2 | 2/2015 | Conn |
| 8,974,411 B2 | 3/2015 | McKinnon |
| 8,996,095 B2 | 3/2015 | Anderson et al. |
| 9,014,786 B2 | 4/2015 | Carmeli et al. |
| 9,023,070 B2 | 5/2015 | Levine et al. |
| 9,034,007 B2 | 5/2015 | Janardhan |
| 9,107,691 B2 | 8/2015 | Fojtik |
| 9,119,656 B2 | 9/2015 | Bose et al. |
| 9,126,018 B1 | 9/2015 | Garrison |
| 9,144,383 B2 | 9/2015 | Zharov |
| 9,144,662 B2 | 9/2015 | Di Caprio et al. |
| RE45,760 E | 10/2015 | Root et al. |
| RE45,776 E | 10/2015 | Root et al. |
| 9,199,057 B2 | 12/2015 | Nielsen |
| 9,211,132 B2 | 12/2015 | Bowman |
| 9,220,562 B2 | 12/2015 | Brannan et al. |
| 9,233,230 B2 | 1/2016 | Puhasmagi et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,352,123 B2 | 5/2016 | Zhou et al. |

(56) References Cited

U.S. PATENT DOCUMENTS

| | | |
|---|---|---|
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,433,427 B2 | 9/2016 | Look et al. |
| 9,439,791 B2 | 9/2016 | Vong et al. |
| 9,445,828 B2 | 9/2016 | Turjman et al. |
| 9,445,927 B2 | 9/2016 | Lee et al. |
| 9,451,884 B2 | 9/2016 | Zharov et al. |
| 9,451,963 B2 | 9/2016 | Cruise et al. |
| 9,486,221 B2 | 11/2016 | Cruise et al. |
| 9,486,611 B2 | 11/2016 | Petersen et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,615,832 B2 | 4/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,764,118 B2 | 9/2017 | Anderson et al. |
| 9,770,251 B2 | 9/2017 | Bowman et al. |
| 9,789,242 B2 | 10/2017 | Criado et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,867,725 B2 | 1/2018 | Tieu et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 10,058,339 B2 | 8/2018 | Galdonik et al. |
| 10,124,146 B2 | 11/2018 | Di Caprio et al. |
| 10,183,146 B2 | 1/2019 | Yang et al. |
| 10,192,230 B2 | 1/2019 | Look et al. |
| 10,299,944 B2 | 5/2019 | Al-Lamee et al. |
| 10,327,790 B2 | 6/2019 | Garrison et al. |
| 10,441,301 B2 | 10/2019 | Vale et al. |
| 10,456,552 B2 | 10/2019 | Goyal |
| 10,485,956 B2 | 11/2019 | O'Donovan |
| 10,667,871 B2 | 6/2020 | Romo et al. |
| 11,020,133 B2 | 6/2021 | Wilson et al. |
| 11,065,019 B1 | 7/2021 | Chou et al. |
| 11,400,255 B1 | 8/2022 | Chou et al. |
| 11,576,691 B2 | 2/2023 | Chou et al. |
| 2001/0014790 A1 | 8/2001 | Heller et al. |
| 2001/0027310 A1 | 10/2001 | Parisi et al. |
| 2001/0031980 A1 | 10/2001 | Wensel et al. |
| 2001/0044598 A1 | 11/2001 | Parodi |
| 2001/0044600 A1 | 11/2001 | Elkins |
| 2001/0044632 A1 | 11/2001 | Daniel et al. |
| 2001/0049486 A1 | 12/2001 | Evans et al. |
| 2001/0049517 A1 | 12/2001 | Zadno-Azizi et al. |
| 2001/0051811 A1 | 12/2001 | Bonnette et al. |
| 2002/0016565 A1 | 2/2002 | Zadno-Azizi et al. |
| 2002/0026145 A1 | 2/2002 | Bagaoisan et al. |
| 2002/0035347 A1 | 3/2002 | Bagaoisan et al. |
| 2002/0055747 A1 | 5/2002 | Cano et al. |
| 2002/0062133 A1 | 5/2002 | Gilson et al. |
| 2002/0072705 A1 | 6/2002 | Vrba et al. |
| 2002/0077600 A1 | 6/2002 | Sirimanne |
| 2002/0087076 A1 | 7/2002 | Meguro et al. |
| 2002/0087119 A1 | 7/2002 | Parodi |
| 2002/0095174 A1 | 7/2002 | Tsugita et al. |
| 2002/0111648 A1 | 8/2002 | Kusleika et al. |
| 2002/0111666 A1 | 8/2002 | Hart et al. |
| 2002/0123765 A1 | 9/2002 | Sepetka et al. |
| 2002/0128679 A1 | 9/2002 | Turovskiy et al. |
| 2002/0133111 A1 | 9/2002 | Shadduck |
| 2002/0138094 A1 | 9/2002 | Borillo et al. |
| 2002/0143362 A1 | 10/2002 | Macoviak et al. |
| 2002/0151922 A1 | 10/2002 | Hogendijk et al. |
| 2002/0151927 A1 | 10/2002 | Douk et al. |
| 2002/0156455 A1 | 10/2002 | Barbut |
| 2002/0156460 A1 | 10/2002 | Ye et al. |
| 2002/0165571 A1 | 11/2002 | Hebert et al. |
| 2002/0165574 A1 | 11/2002 | Ressemann et al. |
| 2002/0165598 A1 | 11/2002 | Wahr et al. |
| 2002/0169472 A1 | 11/2002 | Douk et al. |
| 2002/0173785 A1 | 11/2002 | Spear et al. |
| 2002/0173815 A1 | 11/2002 | Hogendijk et al. |
| 2002/0177869 A1 | 11/2002 | Eidenschink et al. |
| 2002/0177899 A1 | 11/2002 | Eum et al. |
| 2002/0183782 A1 | 12/2002 | Tsugita et al. |
| 2002/0183783 A1 | 12/2002 | Shadduck |
| 2003/0023263 A1 | 1/2003 | Krolik et al. |
| 2003/0040762 A1 | 2/2003 | Dorros et al. |
| 2003/0050600 A1 | 3/2003 | Ressemann et al. |
| 2003/0065353 A1 | 4/2003 | Horzewski et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0120208 A1 | 6/2003 | Houser et al. |
| 2003/0130577 A1 | 7/2003 | Purdy et al. |
| 2003/0135193 A1 | 7/2003 | Hilgers et al. |
| 2003/0135198 A1 | 7/2003 | Berhow et al. |
| 2003/0135232 A1 | 7/2003 | Douk et al. |
| 2003/0153942 A1 | 8/2003 | Wang et al. |
| 2003/0186203 A1 | 10/2003 | Aboud |
| 2003/0191492 A1 | 10/2003 | Gellman et al. |
| 2003/0212304 A1 | 11/2003 | Lattouf |
| 2003/0212384 A1* | 11/2003 | Hayden ............... A61M 29/02 604/533 |
| 2003/0233038 A1 | 12/2003 | Hassett |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0019322 A1 | 1/2004 | Hoffmann |
| 2004/0059243 A1 | 3/2004 | Flores et al. |
| 2004/0116878 A1 | 6/2004 | Byrd et al. |
| 2004/0122360 A1 | 6/2004 | Waldhauser et al. |
| 2004/0133232 A1 | 7/2004 | Rosenbluth et al. |
| 2004/0138608 A1 | 7/2004 | Barbut et al. |
| 2004/0153049 A1 | 8/2004 | Hewitt et al. |
| 2004/0153118 A1 | 8/2004 | Clubb et al. |
| 2004/0193177 A1 | 9/2004 | Houghton et al. |
| 2004/0210194 A1 | 10/2004 | Bonnette et al. |
| 2004/0220611 A1 | 11/2004 | Ogle |
| 2004/0230285 A1 | 11/2004 | Gifford, III et al. |
| 2004/0236215 A1 | 11/2004 | Mihara et al. |
| 2004/0243102 A1 | 12/2004 | Berg et al. |
| 2004/0254602 A1 | 12/2004 | Lehe et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0021075 A1 | 1/2005 | Bonnette et al. |
| 2005/0021152 A1 | 1/2005 | Ogle et al. |

(56) References Cited

U.S. PATENT DOCUMENTS

| | | |
|---|---|---|
| 2005/0027236 A1 | 2/2005 | Douk |
| 2005/0049574 A1 | 3/2005 | Petrick et al. |
| 2005/0059957 A1 | 3/2005 | Campbell et al. |
| 2005/0065467 A1 | 3/2005 | Pudelko et al. |
| 2005/0065498 A1 | 3/2005 | McFerran |
| 2005/0085746 A1 | 4/2005 | Adams et al. |
| 2005/0085847 A1 | 4/2005 | Galdonik et al. |
| 2005/0090802 A1 | 4/2005 | Connors et al. |
| 2005/0103332 A1 | 5/2005 | Gingles et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0182386 A1 | 8/2005 | Aggerholm |
| 2005/0209559 A1 | 9/2005 | Thornton et al. |
| 2005/0209631 A1 | 9/2005 | Galdonik et al. |
| 2005/0209674 A1 | 9/2005 | Kutscher et al. |
| 2005/0209675 A1 | 9/2005 | Ton et al. |
| 2005/0228479 A1 | 10/2005 | Pavcnik et al. |
| 2005/0245892 A1 | 11/2005 | Elkins et al. |
| 2005/0273051 A1 | 12/2005 | Coppi |
| 2005/0277976 A1 | 12/2005 | Galdonik et al. |
| 2006/0020165 A1 | 1/2006 | Adams |
| 2006/0030835 A1 | 2/2006 | Sherman et al. |
| 2006/0030876 A1 | 2/2006 | Peacock et al. |
| 2006/0047301 A1 | 3/2006 | Ogle |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064036 A1 | 3/2006 | Osborne et al. |
| 2006/0069381 A1 | 3/2006 | Itou et al. |
| 2006/0079787 A1 | 4/2006 | Whiting et al. |
| 2006/0089618 A1 | 4/2006 | McFerran et al. |
| 2006/0095062 A1 | 5/2006 | Stephens |
| 2006/0100530 A1 | 5/2006 | Kliot et al. |
| 2006/0129091 A1 | 6/2006 | Bonnette et al. |
| 2006/0135961 A1 | 6/2006 | Rosenman et al. |
| 2006/0155367 A1 | 7/2006 | Hines |
| 2006/0173440 A1 | 8/2006 | Lamson et al. |
| 2006/0195137 A1 | 8/2006 | Sepetka et al. |
| 2006/0200047 A1 | 9/2006 | Galdonik et al. |
| 2006/0200191 A1 | 9/2006 | Zadno-Azizi |
| 2006/0217664 A1 | 9/2006 | Hattler et al. |
| 2006/0247755 A1 | 11/2006 | Pal et al. |
| 2006/0258987 A1 | 11/2006 | Lentz et al. |
| 2006/0259063 A1 | 11/2006 | Bates et al. |
| 2006/0264759 A1 | 11/2006 | Moehring et al. |
| 2006/0271098 A1 | 11/2006 | Peacock |
| 2007/0005084 A1 | 1/2007 | Clague et al. |
| 2007/0016132 A1 | 1/2007 | Oepen et al. |
| 2007/0021778 A1 | 1/2007 | Carly |
| 2007/0043333 A1 | 2/2007 | Kampa et al. |
| 2007/0060888 A1 | 3/2007 | Goff et al. |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0073264 A1 | 3/2007 | Stedman et al. |
| 2007/0106211 A1 | 5/2007 | Provost-Tine et al. |
| 2007/0135733 A1 | 6/2007 | Soukup et al. |
| 2007/0173784 A1 | 7/2007 | Johansson et al. |
| 2007/0185501 A1 | 8/2007 | Martin et al. |
| 2007/0185521 A1 | 8/2007 | Bui et al. |
| 2007/0185522 A1 | 8/2007 | Davies et al. |
| 2007/0191820 A1 | 8/2007 | Maksimovich |
| 2007/0197956 A1 | 8/2007 | Le et al. |
| 2007/0198028 A1 | 8/2007 | Miloslavski et al. |
| 2007/0198049 A1 | 8/2007 | Barbut |
| 2007/0208302 A1 | 9/2007 | Webster et al. |
| 2007/0213765 A1 | 9/2007 | Adams et al. |
| 2007/0227543 A1 | 10/2007 | Peichel |
| 2007/0239261 A1 | 10/2007 | Bose et al. |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2007/0260219 A1 | 11/2007 | Root et al. |
| 2008/0027379 A1 | 1/2008 | Wilkins |
| 2008/0033525 A1 | 2/2008 | Shaked et al. |
| 2008/0058839 A1 | 3/2008 | Nobles et al. |
| 2008/0082107 A1 | 4/2008 | Miller et al. |
| 2008/0082109 A1 | 4/2008 | Moll et al. |
| 2008/0086110 A1 | 4/2008 | Galdonik et al. |
| 2008/0097251 A1 | 4/2008 | Babaev |
| 2008/0109088 A1 | 5/2008 | Galdonik et al. |
| 2008/0119890 A1 | 5/2008 | Adams et al. |
| 2008/0140010 A1 | 6/2008 | Kennedy et al. |
| 2008/0167678 A1 | 7/2008 | Morsi |
| 2008/0172066 A9 | 7/2008 | Galdonik et al. |
| 2008/0177245 A1 | 7/2008 | Mesallum |
| 2008/0183128 A1 | 7/2008 | Morriss et al. |
| 2008/0188888 A1 | 8/2008 | Adams et al. |
| 2008/0195140 A1 | 8/2008 | Myla et al. |
| 2008/0200946 A1 | 8/2008 | Braun et al. |
| 2008/0234723 A1 | 9/2008 | Buiser et al. |
| 2008/0243222 A1 | 10/2008 | Schafersman et al. |
| 2008/0262350 A1 | 10/2008 | Unger |
| 2008/0262472 A1 | 10/2008 | Lunn et al. |
| 2008/0262506 A1 | 10/2008 | Griffin et al. |
| 2008/0281248 A1 | 11/2008 | Angheloiu et al. |
| 2008/0294111 A1 | 11/2008 | Tal et al. |
| 2008/0312639 A1 | 12/2008 | Weber |
| 2009/0018455 A1 | 1/2009 | Chang |
| 2009/0018525 A1 | 1/2009 | Waite et al. |
| 2009/0024072 A1 | 1/2009 | Criado et al. |
| 2009/0024089 A1 | 1/2009 | Levine et al. |
| 2009/0030400 A1 | 1/2009 | Bose et al. |
| 2009/0082800 A1 | 3/2009 | Janardhan |
| 2009/0124956 A1 | 5/2009 | Swetlin et al. |
| 2009/0163891 A1 | 6/2009 | Ewing et al. |
| 2009/0165881 A1 | 7/2009 | Tegg et al. |
| 2009/0198172 A1 | 8/2009 | Garrison et al. |
| 2009/0209857 A1 | 8/2009 | Secretain et al. |
| 2009/0227992 A1 | 9/2009 | Nir et al. |
| 2009/0234321 A1 | 9/2009 | Shapland et al. |
| 2009/0247987 A1 | 10/2009 | Chevalier, Jr. et al. |
| 2009/0254166 A1 | 10/2009 | Chou et al. |
| 2009/0264865 A1 | 10/2009 | Kawai |
| 2009/0270800 A1 | 10/2009 | Spurchise et al. |
| 2009/0281379 A1 | 11/2009 | Binmoeller et al. |
| 2009/0299393 A1 | 12/2009 | Martin et al. |
| 2009/0312699 A1 | 12/2009 | Pudelko et al. |
| 2009/0312786 A1 | 12/2009 | Trask et al. |
| 2010/0004607 A1 | 1/2010 | Wilson et al. |
| 2010/0022948 A1 | 1/2010 | Wilson et al. |
| 2010/0030141 A1 | 2/2010 | Chermoni |
| 2010/0030186 A1 | 2/2010 | Stivland |
| 2010/0042118 A1 | 2/2010 | Garrison et al. |
| 2010/0049168 A1 | 2/2010 | Parker et al. |
| 2010/0057051 A1 | 3/2010 | Howat et al. |
| 2010/0063479 A1 | 3/2010 | Merdan et al. |
| 2010/0063480 A1 | 3/2010 | Shireman |
| 2010/0094330 A1 | 4/2010 | Barbut |
| 2010/0114017 A1 | 5/2010 | Lenker et al. |
| 2010/0125322 A1 | 5/2010 | Fitzgerald et al. |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0211050 A1 | 8/2010 | Luther |
| 2010/0217235 A1 | 8/2010 | Thorstenson et al. |
| 2010/0217276 A1 | 8/2010 | Garrison et al. |
| 2010/0228269 A1 | 9/2010 | Garrison et al. |
| 2010/0256600 A1 | 10/2010 | Ferrera |
| 2010/0268029 A1 | 10/2010 | Phan et al. |
| 2010/0312141 A1 | 12/2010 | Keast et al. |
| 2010/0318097 A1 | 12/2010 | Ferrera et al. |
| 2011/0009875 A1 | 1/2011 | Grandfield et al. |
| 2011/0015482 A1 | 1/2011 | Carrillo, Jr. |
| 2011/0022149 A1 | 1/2011 | Cox et al. |
| 2011/0034986 A1 | 2/2011 | Chou et al. |
| 2011/0046709 A1 | 2/2011 | Coffey et al. |
| 2011/0082373 A1 | 4/2011 | Gurley et al. |
| 2011/0087147 A1 | 4/2011 | Garrison et al. |
| 2011/0106200 A1 | 5/2011 | Ziegler |
| 2011/0112567 A1 | 5/2011 | Lenker et al. |
| 2011/0125181 A1 | 5/2011 | Brady et al. |

(56) References Cited

U.S. PATENT DOCUMENTS

| | | |
|---|---|---|
| 2011/0152760 A1 | 6/2011 | Parker |
| 2011/0160833 A1 | 6/2011 | Gonzalez et al. |
| 2011/0172678 A1 | 7/2011 | Behl et al. |
| 2011/0172700 A1 | 7/2011 | Bose et al. |
| 2011/0213297 A1* | 9/2011 | Aklog .............. A61B 17/22 604/28 |
| 2011/0230859 A1 | 9/2011 | Galdonik et al. |
| 2011/0238041 A1 | 9/2011 | Lim et al. |
| 2011/0238083 A1 | 9/2011 | Moll et al. |
| 2011/0245751 A1 | 10/2011 | Hofmann |
| 2011/0264133 A1 | 10/2011 | Hanlon et al. |
| 2012/0040858 A1 | 2/2012 | Ford et al. |
| 2012/0065479 A1 | 3/2012 | Lahiji et al. |
| 2012/0065490 A1 | 3/2012 | Zharov et al. |
| 2012/0071838 A1 | 3/2012 | Fojtik |
| 2012/0071856 A1 | 3/2012 | Goldfarb et al. |
| 2012/0078140 A1 | 3/2012 | Nita |
| 2012/0095485 A1 | 4/2012 | Cully et al. |
| 2012/0101561 A1 | 4/2012 | Porter |
| 2012/0109044 A1 | 5/2012 | Santamore et al. |
| 2012/0116350 A1 | 5/2012 | Strauss et al. |
| 2012/0123466 A1 | 5/2012 | Porter et al. |
| 2012/0148175 A1 | 6/2012 | Wesselmann |
| 2012/0150147 A1 | 6/2012 | Leynov et al. |
| 2012/0165756 A1 | 6/2012 | Root et al. |
| 2012/0172918 A1 | 7/2012 | Fifer et al. |
| 2012/0179097 A1 | 7/2012 | Cully et al. |
| 2012/0253313 A1 | 10/2012 | Galdonik et al. |
| 2012/0271281 A1 | 10/2012 | Schertiger |
| 2012/0277671 A1 | 11/2012 | Fuentes |
| 2012/0296275 A1 | 11/2012 | Martin et al. |
| 2012/0310212 A1 | 12/2012 | Fischell et al. |
| 2012/0310319 A1 | 12/2012 | Tieu et al. |
| 2012/0330196 A1 | 12/2012 | Nita |
| 2013/0006174 A1 | 1/2013 | Phan |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |
| 2013/0053792 A1 | 2/2013 | Fischell et al. |
| 2013/0116701 A1 | 5/2013 | Wang et al. |
| 2013/0131691 A1 | 5/2013 | Kozak et al. |
| 2013/0158507 A1 | 6/2013 | Brown |
| 2013/0158578 A1 | 6/2013 | Ghodke et al. |
| 2013/0165873 A1 | 6/2013 | Morriss et al. |
| 2013/0172851 A1 | 7/2013 | Shimada et al. |
| 2013/0184735 A1 | 7/2013 | Fischell et al. |
| 2013/0197621 A1 | 8/2013 | Ryan et al. |
| 2013/0226276 A1 | 8/2013 | Newell et al. |
| 2013/0274783 A1 | 10/2013 | Wynberg |
| 2013/0281788 A1 | 10/2013 | Garrison |
| 2014/0012281 A1 | 1/2014 | Wang et al. |
| 2014/0018732 A1 | 1/2014 | Bagaoisan et al. |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0046297 A1 | 2/2014 | Shimada et al. |
| 2014/0081243 A1 | 3/2014 | Zhou et al. |
| 2014/0088510 A1 | 3/2014 | Nimkar et al. |
| 2014/0114287 A1 | 4/2014 | Beasley et al. |
| 2014/0155783 A1 | 6/2014 | Starksen et al. |
| 2014/0155908 A1 | 6/2014 | Rosenbluth et al. |
| 2014/0155932 A1 | 6/2014 | Weishaupt et al. |
| 2014/0180246 A1 | 6/2014 | Comerota et al. |
| 2014/0207043 A1 | 7/2014 | Anand et al. |
| 2014/0228808 A1 | 8/2014 | Webster et al. |
| 2014/0236120 A1 | 8/2014 | Tsai et al. |
| 2014/0249508 A1 | 9/2014 | Wang et al. |
| 2014/0257018 A1 | 9/2014 | Farnan |
| 2014/0257186 A1 | 9/2014 | Kerr |
| 2014/0273920 A1 | 9/2014 | Smith |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296769 A1 | 10/2014 | Hyde et al. |
| 2014/0296868 A1 | 10/2014 | Garrison et al. |
| 2014/0296889 A1 | 10/2014 | Avneri et al. |
| 2014/0343537 A1 | 11/2014 | Eversull et al. |
| 2014/0358123 A1 | 12/2014 | Ueda et al. |
| 2014/0358178 A1 | 12/2014 | Hewitt et al. |
| 2014/0371709 A1 | 12/2014 | Allen et al. |
| 2015/0025562 A1 | 1/2015 | Dinh et al. |
| 2015/0080939 A1 | 3/2015 | Adams et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0151090 A1 | 6/2015 | Sutton et al. |
| 2015/0165160 A1 | 6/2015 | Thungana et al. |
| 2015/0173782 A1 | 6/2015 | Garrison et al. |
| 2015/0174368 A1* | 6/2015 | Garrison .......... A61M 25/0041 604/525 |
| 2015/0196210 A1 | 7/2015 | McCaffrey et al. |
| 2015/0245848 A1 | 9/2015 | Shimon |
| 2015/0265802 A1 | 9/2015 | Fukuoka et al. |
| 2015/0282821 A1 | 10/2015 | Look et al. |
| 2015/0327843 A1 | 11/2015 | Garrison |
| 2015/0327919 A1 | 11/2015 | Clopp et al. |
| 2015/0335857 A1 | 11/2015 | Ishikawa |
| 2015/0352330 A1 | 12/2015 | Wasdyke et al. |
| 2016/0008025 A1 | 1/2016 | Gupta et al. |
| 2016/0008572 A1 | 1/2016 | Di Caprio et al. |
| 2016/0015935 A1 | 1/2016 | Chan et al. |
| 2016/0022964 A1 | 1/2016 | Goyal |
| 2016/0058459 A1 | 3/2016 | Bowman |
| 2016/0066931 A1 | 3/2016 | Kugler et al. |
| 2016/0081825 A1 | 3/2016 | Sudin et al. |
| 2016/0096002 A1 | 4/2016 | Di Caprio et al. |
| 2016/0100819 A1 | 4/2016 | Tieu |
| 2016/0121081 A1 | 5/2016 | Iwano et al. |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0136398 A1 | 5/2016 | Heilman et al. |
| 2016/0143661 A1 | 5/2016 | Wood et al. |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206322 A1 | 7/2016 | Fitz et al. |
| 2016/0220396 A1 | 8/2016 | Zhou et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346502 A1 | 12/2016 | Fuller et al. |
| 2016/0346508 A1 | 12/2016 | Williams et al. |
| 2016/0346509 A1 | 12/2016 | Anderson et al. |
| 2016/0361180 A1 | 12/2016 | Vong et al. |
| 2016/0361459 A1 | 12/2016 | Baldwin |
| 2016/0367272 A1* | 12/2016 | Garrison .............. A61M 25/10 |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072165 A1 | 3/2017 | Lim et al. |

(56) References Cited

U.S. PATENT DOCUMENTS

| | | |
|---|---|---|
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0231647 A1 | 8/2017 | Saunders et al. |
| 2017/0238950 A1 | 8/2017 | Yang et al. |
| 2017/0239440 A1 | 8/2017 | Yang et al. |
| 2017/0239447 A1 | 8/2017 | Yang et al. |
| 2017/0246014 A1 | 8/2017 | Rapaport et al. |
| 2017/0252043 A1 | 9/2017 | Fuller et al. |
| 2017/0252536 A1 | 9/2017 | Yang et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0333060 A1 | 11/2017 | Panian |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Greene, Jr. et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Panian |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Baldwin et al. |
| 2018/0064453 A1 | 3/2018 | Garrison et al. |
| 2018/0116684 A1 | 5/2018 | Garrison et al. |
| 2018/0133436 A1 | 5/2018 | Garrison et al. |
| 2018/0193042 A1 | 7/2018 | Wilson et al. |
| 2018/0207399 A1 | 7/2018 | Chou et al. |
| 2018/0242978 A1 | 8/2018 | Chou et al. |
| 2018/0339130 A1 | 11/2018 | Ogle |
| 2018/0361114 A1 | 12/2018 | Chou et al. |
| 2019/0008534 A1 | 1/2019 | Garrison et al. |
| 2019/0046218 A1 | 2/2019 | Garrison et al. |
| 2019/0133744 A1 | 5/2019 | Janardhan et al. |
| 2019/0224456 A1 | 7/2019 | Kon et al. |
| 2019/0269538 A1 | 9/2019 | Chou et al. |
| 2019/0351182 A1 | 11/2019 | Chou et al. |
| 2019/0366042 A1 | 12/2019 | Garrison et al. |
| 2019/0366043 A1 | 12/2019 | Garrison et al. |
| 2020/0009301 A1 | 1/2020 | Yee |
| 2020/0016369 A1 | 1/2020 | Garrison et al. |
| 2020/0023160 A1 | 1/2020 | Chou et al. |
| 2020/0038628 A1 | 2/2020 | Chou et al. |
| 2020/0046939 A1 | 2/2020 | Garrison et al. |
| 2020/0046940 A1 | 2/2020 | Garrison et al. |
| 2020/0060722 A1 | 2/2020 | O'Connell et al. |
| 2020/0086089 A1 | 3/2020 | Kugler et al. |
| 2020/0164178 A1 | 5/2020 | Garrison et al. |
| 2020/0179661 A1 | 6/2020 | Fischell et al. |
| 2020/0187965 A1 | 6/2020 | Garrison et al. |
| 2020/0215306 A1 | 7/2020 | Garrison et al. |
| 2020/0253670 A1 | 8/2020 | Doisneau et al. |
| 2020/0289136 A1 | 9/2020 | Chou |
| 2020/0337716 A1 | 10/2020 | Garrison et al. |
| 2020/0345981 A1 | 11/2020 | Garrison et al. |
| 2021/0045758 A1 | 2/2021 | Garrison et al. |
| 2021/0052296 A1 | 2/2021 | Garrison |
| 2021/0059713 A1 | 3/2021 | Patel et al. |
| 2021/0069467 A1 | 3/2021 | Garrison et al. |
| 2021/0128183 A1 | 5/2021 | Lee |
| 2021/0138193 A1 | 5/2021 | Garrison et al. |
| 2021/0138194 A1 | 5/2021 | Garrison et al. |
| 2021/0212707 A1 | 7/2021 | Chou et al. |
| 2021/0259718 A1 | 8/2021 | Wilson et al. |
| 2021/0275197 A1* | 9/2021 | Vale ............... A61M 25/0074 |
| 2021/0298773 A1 | 9/2021 | Echarri et al. |
| 2021/0330332 A1 | 10/2021 | Chou et al. |
| 2021/0338256 A1 | 11/2021 | Chou et al. |
| 2022/0047285 A1 | 2/2022 | Chou et al. |
| 2022/0080156 A1 | 3/2022 | Kugler et al. |

FOREIGN PATENT DOCUMENTS

| | | |
|---|---|---|
| CN | 103260689 A | 8/2013 |
| CN | 103284775 A | 9/2013 |
| CN | 103648574 A | 3/2014 |
| CN | 104394785 A | 3/2015 |
| CN | 104739486 A | 7/2015 |
| CN | 105920720 A | 9/2016 |
| CN | 106039526 A | 10/2016 |
| CN | 114391960 A | 4/2022 |
| DE | 102006039236 A1 | 2/2008 |
| EP | 117940 A2 | 9/1984 |
| EP | 0427429 A2 | 5/1991 |
| EP | 1226795 A2 | 7/2002 |
| EP | 1440663 A1 | 7/2004 |
| EP | 1639951 A1 | 3/2006 |
| EP | 2 069 528 B1 | 3/2013 |
| EP | 2821094 A1 | 1/2015 |
| GB | 2020557 A | 11/1979 |
| JP | 3026200 U | 7/1996 |
| JP | H11-146883 A | 6/1999 |
| JP | 2002291756 A | 10/2002 |
| JP | 2006-087643 A | 4/2006 |
| JP | 2008-503249 A | 2/2008 |
| JP | 2008517652 A | 5/2008 |
| JP | 3142466 U | 6/2008 |
| JP | 2014-138756 A | 7/2014 |
| WO | WO-93/17750 A1 | 9/1993 |
| WO | WO-94/02194 A1 | 2/1994 |
| WO | WO-95/05209 A1 | 2/1995 |
| WO | WO-98/38930 A1 | 9/1998 |
| WO | WO-99/45835 A2 | 9/1999 |
| WO | WO-00/16705 A1 | 3/2000 |
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-02/055146 A1 | 7/2002 |
| WO | WO-02/085092 A2 | 10/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2005/084130 A2 | 9/2005 |
| WO | WO-2006/111944 A1 | 10/2006 |
| WO | WO-2006/127929 A2 | 11/2006 |
| WO | WO-2006/132434 A1 | 12/2006 |
| WO | WO-2007/098494 A1 | 8/2007 |
| WO | WO-2008/006111 A2 | 1/2008 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |

(56) References Cited

FOREIGN PATENT DOCUMENTS

| WO | WO-2010/039456 A1 | 4/2010 |
|----|-------------------|---------|
| WO | WO-2010/075445 A1 | 7/2010 |
| WO | WO-2011/011493 A1 | 1/2011 |
| WO | WO-2012/009518 A1 | 1/2012 |
| WO | WO-2012/035633 A1 | 3/2012 |
| WO | WO-2012/047803 A2 | 4/2012 |
| WO | WO-2014/008489 A1 | 1/2014 |
| WO | WO-2014/203336 A1 | 12/2014 |
| WO | WO-2015/042368 A2 | 3/2015 |
| WO | WO-2015/100178 A1 | 7/2015 |
| WO | WO-2015/157330 A1 | 10/2015 |
| WO | WO-2017/118818 A1 | 7/2017 |
| WO | WO-2020/061240 A1 | 3/2020 |
| WO | WO-2020/132003 A1 | 6/2020 |
| WO | WO-2021/007346 A1 | 1/2021 |
| WO | WO-2021/011554 A1 | 1/2021 |

OTHER PUBLICATIONS

"2012 Buyer's Guide: Microcatheters." Endovascular Today, 2012, pp. 48-51.
"2017 Buyer's Guide: Microcatheters." Endovascular Today, http://evtoday.com/buyers-guide/chart.asp?id=25. Accessed on Oct. 10, 2017. 11 pages.
"Asahi Fubuki Catheter Dilator Kit." Asahi-Intecc USA Medical. 2017. Web. Accessed Oct. 2, 2017. 3 pages. www.asahi-inteccusa-medical.com/medical-product/fubuki-dilator-kit/. Accessed Oct. 2, 2017.
Adami, M.D., et al., (2002). "Use of the Parodi Anti-Embolism System in Carotid Stenting: Italian Trial Results" J Endovasc Ther, 9:147-154.
Alexandrescu et al. (2006) "Filter-protected carotid stenting via a minimal cervical access with transitory aspirated reversed flow during initial passage of the target lesion." J. Endovasc. Ther. 13(2):196-20.
Alvarez et al. (2008). "Transcervical carotid stenting with flow reversal is safe in octogenarians: A preliminary safety study" J. Vasc. Surg. 47:96-100.
Arslanian, R., M. Gounis, and J. Chueh. "Pump or Syringe? Evaluation of Aspiration Efficacy with Neurovascular Catheters," (Oral Presentation, SNIS 2018), 2 pages. Web. Date accessed Feb. 10, 2020.
Bates M.D., et al. (2003). "Reversal of the Direction of Internal Carotid Artery Blood Flow by Occlusion of the Common and External Carotid Arteries in a Swine Model" Catherization and Cardiovascular Intervention 60:270-275.
Bates, M.D., et al. (2004). "Internal Carotid Artery Flow Arrest/Reversal Cerebral Protection Techniques" The West Virginal Medical Journal, vol. 99:60-63.
Bergeron et al. (1999). "Percutaneous stenting of the internal carotid artery: the European CAST I Study" J. Endovasc. Surg. 6:155-159.
Bergeron et al. (2008). MEET Presentation, Cannes, French Riviera "Why I do not use routine femoral access for CAS." 12 pages.
Bergeron P. et al. (1996). "Recurrent Carotid Disease: Will Stents be an alternative to surgery?" J Endovasc Surg; 3: 76-79.
Bourekas, E. C., A. P. Slivka, et al. (2004). "Intraarterial thrombolytic therapy within 3 hours of the onset of stroke." Neurosurgery 54(1): 39-44; discussion 44-6.
Caldwell, J. (2021). "Aspiration thrombectomy using a novel 088 catheter and specialized delivery catheter." Journal of NeuroInterventional Surgery, Published Online First: Dec. 14, 2021. 5 pages. doi: 10.1136/neurintsurg-2021-018318.
Chang, D.W. et al. (2004). "A new approach to carotid angioplasty and stenting with transcervical occlusion and protective shunting: Why it may be a better carotid artery intervention" (J Vasc Surg 2004; 39:994-1002.).
Chang, M.D., "Carotid Angioplasty And Stenting Using Transcervical Occlusion And Protective Shunting Via A Mini Incision In The Neck: A New Technique For Difficult Femoral Access Or Filter Placement May Be The Better Carotid Artery Intervention" 30th Global: Vascular and Endovascular Issues, Techniques and Horizons Symposium, New York, NY, Nov. 20-23, 2003; XXVII 6.1-XXVII 6.2.
Cohen et al., "A reappraisal of the common carotid artery as an access site in interventional procedures for acute stroke therapies", Case Reports, Journal of Clinical Neuroscience 19 (2012) pp. 323-326.
Coppi et al. (2005). "PRIAMUS Proximal flow blockage cerebral protection during carotid stenting: Results from a multicenter Italian regiStry" J. Cardiovasc. Surg. 46:219-227.
Criado et al. (1997) "Evolving indications for and early results of carotid artery stenting" Am. J. Surg.; 174:111-114.
Criado et al. (2004). "Transcervical carotid artery angioplasty and stenting with carotid flow reversal: Surgical technique" J. Vasc. Surg. 18:257-261.
Criado et al. (2004). "Transcervical carotid stenting with internal carotid artery flow reversal: Feasibility and preliminary results" J. Vasc. Surg. 40:476-483.
Criado, et al. (2007). "Transcervical carotid stenting with carotid artery flow reversal: 3-year follow-up of 103 stents." J Vasc Surg 46(5): 864-9.
Criado, F.J., et al. (2000). Access strategies for carotid artery intervention. J Invasive Cardiol, 12(1): p. 61-8.
Criado, M.D., et al. (2004) "Carotid angioplasty with internal carotid artery flow reversal is well tolerated in the awake patient" Journal of Vascular Surgery, 40(1):92-7.
Delgado Almandoz, Josser E., et al. "Comparison of clinical outcomes in patients with acute ischemic strokes treated with mechanical thrombectomy using either Solumbra or ADAPT techniques." *Journal of NeuroInterventional Surgery*, vol. 8, 2016, pp. 1123-1128.
Diederich et al. (2004) "First Clinical experiences with an endovascular clamping system for neuroprotection during carotid stenting" *Eur. J. Vasc. Endovasc. Surg*. 28:629-633.
Diethrich et al., (1996). "Percutaneous techniques for endoluminal carotid interventions" J. Endovasc. Surg. 3:182-202.
Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.
Farooq, Vasim et al. "Forward and Back Aspiration during ST-Elevation Myocardial Infarction: a Feasibility Study." EuroIntervention, vol. 11, No. 14, 2016, pp. 1639-1648.
Farooq, Vasim et al. "The Use of A Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.
Feldman. (1987)."Transcatheter Aspiration of a Thrombus in an Aortocoronary Saphenous Vein Graft," *American Journal of Cardiology*, 60(4):379-380.
Feldtman, R. W., C. J. Buckley, et al. (2006). "How I do it: cervical access for carotid artery stenting." Am J Surg 192(6): 779-81.
Fiorella, D., M. Kelly, et al. (2008). "Endovascular Treatment of Cerebral Aneurysms." Endovascular Today Jun. 2008. pp. 53-64.
Fischell, Tim et al. (2021). "A Next-Generation Guide Extension System for Percutaneous Coronary Intervention" Cardiovascular Revascularization Medicine 2021. 32:50-55. Publ. Web Dec. 23, 2020.
Frazee, J. G. and X. Luo (1999). "Retrograde transvenous perfusion." Crit Care Clin 15(4): 777-88, vii.
Frazee, J. G., X. Luo, et al. (1998). "Retrograde transvenous neuroperfusion: a back door treatment for stroke." Stroke 29(9): 1912-6.
Friedrich, Benjamin, et al. "Distance to Thrombus in Acute Middle Cerebral Artery Occlusion." Stroke, vol. 46, No. 3, 2015, pp. 692-696.
Frölich AM, et al. (2020, Epub Sep. 3, 2020). "The novel Tenzing 7 delivery catheter designed to deliver intermediate catheters to the face of embolus without crossing: clinical performance predicted in anatomically challenging model." J NeuroIntervent Surg, 5 pages. doi:10.1136/ neurintsurg-2020-016412.

(56) References Cited

OTHER PUBLICATIONS

Goldstein (2007). "Acute Ischemic Stroke Treatment in 2007" *Circ* 116:1504-1514.
Goyal, M. et al. (Mar. 12, 2015, e-published Feb. 11, 2015). "Randomized Assessment of Rapid Endovascular Treatment of Ischemic Stroke." *N Engl J Med*, 372(11):1019-1030.
Gray et al. (2007) "The CAPTURE registry: Results of carotid stenting with embolic protection in the post approval setting" *Cath. Cardovasc. Interven.* 69:341-348.
Guidezilla Guide Extension Catheter, Boston Scientific 510k Submission, Feb. 19, 2013, 5 pages. Web. Accessed Oct. 23, 2017.
Heart and Stroke Foundation of Canada. "Vacuum cleaner sucks up strokes." *ScienceDaily*, Jun. 8, 2010, 4 pages, www.sciencedaily.com/releases/2010/06/100608162240.htm.
Henry, et al. (1999). "Carotid Stenting With Cerebral Protection: First Clinical Experience Using the PercuSurge GuardWire System" *J. Endovasc. Surg.* 6:321-331.
Hoffer et al. (2003). "Percutaneous Arterial Closure Devices" J. Vasc. Interv. Radiol. 14:865-885.
Hopf-Jensen, S. (Nov. 2016, e-published Jul. 1, 2016) "Impact and Effectiveness of Dual Aspiration Technique in Stent-Assisted Mechanical Thrombectomy: Recent Improvements in Acute Stroke Management," *Cardiovasc Intervent Radiol*, 39:1620-1628.
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Jankowitz, Brian, et al. "Manual Aspiration Thrombectomy Adjunctive Endovascular Recanalization Technique in Acute Stroke Interventions." *Stroke*, vol. 43, No. 5, 2012, pp. 1408-1411.
Kayan, Y. and J. Delgado, "Neurointerventional Treatment of Acute Stroke in 2015 at Abbott Northwestern Hospital," (Nov. 16, 2015). 75 pages. (https://www.slideshare.net/AllinaHealth/neurointerventional-treatment-of-acute-stroke-in-2015-at-abbott-northwestern-hospital).
Koebbe, C. J., E. Veznedaroglu, et al. (2006). "Endovascular management of intracranial aneurysms: current experience and future advances." Neurosurgery 59(5 Suppl 3): S93-102; discussion S3-13.
Kopeck, Rachel. "Penumbra, Inc. Launches 5MAX™ ACE—The Newest Clot Extraction Device to Treat Acute Ischemic Stroke Patients." *Penumbra Inc.*, Jul. 8, 2013, 3 pages, http://www.penumbrainc.com/news/penumbra-inc-launches-5max-ace-the-newest-clot-extraction-device-to-treat-acute-ischemic-stroke-patients/.
Lin et al. (2005) "Protected carotid artery stenting and angioplasty via transfemoral versus transcervical approaches." Vasc. Endovasc. Surg. 39(6):499-503.
Lo et al. (2005) "Advantages and indications of transcervical carotid artery stenting with carotid flow reversal" J. Cardovasc. Surg (Torino). 46(3):229-239.
Luebke, T et al. (2007) "Meta-analysis of randomized trials comparing carotid endarterectomy and endovascular treatment." *Eur. J. Vasc. Endovasc. Surg.* 34:470-479.
Macdonald, S. (2006) "Is there any evidence that cerebral protection is beneficial?" *J. Cardiovasc. Surg.* 47:127-36.
Mas et al. (2006). "Endarterectomy versus stenting in patients with symptomatic severe carotid stenosis" *NEJM* 355:1660-71.
Matas et al. (2007). "Transcervical carotid stenting with flow reversal protection: Experience in high-risk patients" J. Vasc. Surg. 46:49-54.
Merit Medical Systems Acquired Distal Access's SPINR Platform, Jul. 15, 2015, Digital Access, LLC; Merit Medical Systems, 5 pages. Web. Accessed Oct. 23, 2017.
Mokin, Maxim, et al. "Primary stentriever versus combined stentriever plus aspiration thrombectomy approaches: in vitro stroke model comparison." *Journal of NeuroInterventional Surgery*, vol. 7, 2015, pp. 453-457.
MomaPresn (AET). Biamino, G. MO.MA as a distal protective device, University of Leipzig, Heart Center Department of Clinical and Interventional, Angiology Leipzig, Germany, 2002. 37 pages.

Nesbit, G. M., G. Luh, et al. (2004). "New and future endovascular treatment strategies for acute ischemic stroke." J Vasc Interv Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ohki, M.D., et al., "Efficacy of a proximal occlusion catheter with reversal of flow in the prevention of embolic events during carotid artery stenting: An experimental analysis" (J Vasc Surg 2001; 33:504-9).
Ouriel, K., R. K. Greenberg, et al. (2001). "Hemodynamic conditions at the carotid bifurcation during protective common carotid occlusion." J Vasc Surg 34(4): 577-80.
Parodi (2005). "Is flow reversal the best method of protection during carotid stenting?" J Endovasc. Ther. 12:166-170.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Patel, Tejas et al. (2014) "Balloon-Assisted Tracking: A Must-Know Technique to Overcome Difficult Anatomy During Transradial Approach," *Catheter Cardiovasc. Interv.* 83(2):211-220.
Paullus WS, Pait TG, Rhoton Al Jr. Microsurgical exposure of the petrous portion of the carotid artery. J Neurosurg. 1977;47(5):713-726. (Year: 1977).
Pena, Carlos. "Letter to Sequent Medical Inc Re: K150894, Trade/Device Name: VIA™ 21 Microcatheter." Department of Health & Human Services, Aug. 28, 2015, 14 pages.
Penumbra, Inc., "Penumbra, Inc. Completes Pivotal Stroke Trial of Intracranial Revascularization," Press Release, (2007). Web. Accessed Jun. 14, 2017. 2 pages.
Penumbra, Inc., "The Penumbra Pivotal Stroke Trial: Safety and Effectiveness of a New Generation of Mechanical Devices for Clot Removal in Intracranial Large Vessel Occlusive Disease," *Stroke* 2009, 40:2761-2768. Web. Downloaded Jun. 15, 2017.
Pereira, V.M. et al. (2020, e-published Mar. 3, 2020). "First-in-human, robotic-assisted neuroendovascular intervention." Journal of Neurointerventional Surgery, 12(4), 338-340. https://doi.org/10.1136/neurintsurg-2019-015671.rep.
Perez-Arjona, E. A., Z. DelProsto, et al. (2004). "Direct percutaneous carotid artery stenting with distal protection: technical case report." Neurol Res 26(3): 338-41.
Pipinos et al. (2005). "Transcervical approach with protective flow reversal for carotid angioplasty and stenting" J. Endovasc. Ther. 12:446-453.
Pipinos et al. (2006). "Transcervical carotid stenting with flow reversal for neuroprotection: Technique, results, advantages, and limitations" 14(5):245-255.
Powers, W.J., et al. (2015, e-published online before print Jun. 29, 2015). "2015 AHA/ASA Focused Update of the 2013 Guidelines for the Early Management of Patients With Acute Ischemic Stroke Regarding Endovascular Treatment: A Guideline for Healthcare Professionals From the American Heart Association/American Stroke Association Powers et al. on behalf of the American Heart Association Stroke Council Stroke." *Stroke*. 46:3020-3035.
Reeder et al., "Aspiration Thrombectomy for Removal of Coronary Thrombus," *American Journal of Cardiology*. (Jul. 1, 1992) 70:107-110 (Abstract only).
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results froma prospective multicenter registry" J. Endovasc. Ther. 12:156-165.
Request for Ex Parte Reexamination Transmittal Form and Request for Ex Parte Reexamination pursuant to 37 CFR 1.150 of U.S. Pat. No. 9,820,761 issued Nov. 21, 2017. Request filed May 11, 2018 and assigned U.S. Appl. No. 90/014,136. 35 pages.

(56) References Cited

OTHER PUBLICATIONS

Ribo et al. (2006). "Transcranial doppler monitoring of transcervical carotid stenting with flow reversal protection: a novel carotid revascularization technique" 27:2846-2849 (originally published online Sep. 28, 2006).
Ribo, M., C. Molina, et al. (2008). "Buying Time for Recanalization in Acute Stroke: Arterial Blood Infusion Beyond the Occluding Clot as a Neuroprotective Strategy." J Neuroimaging. 4 pages.
Ross, I. B. and G. D. Luzardo (2006). "Direct access to the carotid circulation by cut down for endovascular neuro-interventions." Surg Neurol 65(2): 207-11; discussion 211.
Saver, J.L. et al. (Jun. 11, 2015, e-published Apr. 17, 2015). "Stent-Retriever Thrombectomy after Intravenous t-PA vs. t-PA Alone in Stroke." *N Engl J Med*, 372(24):2285-2295.
Seidel, A. et al. (2005). "Relationship between the diameter of great saphenous vein and body mass index," J Vasc Bras, vol. 4, No. 3, p. 265-269.
Simon et al., Hydrodynamic comparison of the Penumbra system and commonly available syringes in forced-suction thrombectomy, J. Neuro Intervent Surg 2014, 6, pp. 205-211. Web. Downloaded Oct. 18, 2017.
Simon, S. et al. (2014, e-published Nov. 14, 2013) "Exploring the efficacy of cyclic vs static aspiration in a cerebral thrombectomy model: an initial proof of concept study." *J. NeuroIntervent Surg* 6: 677-683. Web. Date accessed Oct. 18, 2017.
Spinnaker® Elite™ Flow Directed Catheters Go with the Flow. Indications for Use. 2 page. Web. Aug. 27, 2019.
Spinnaker® Elite™ Flow Directed Catheters Go with the Flow. Promotional Brochure. 1 page. Web. Aug. 27, 2019.
Spiotta et al., Evolution of thrombectomy approaches and devices for acute stroke: a technical review, J. Neuro Intervent Surg 2015, 7, pp. 2-7. Web. Downloaded Oct. 18, 2017.
Stecker et al., (2002). "Stent placement in common carotid and internal carotid artery stenoses with use of an open transcervical approach in a patient with previous endarterectomy" J. Vasc. Interv. Radiol. 13:413-417.
Stejskal, et al. "Experience of 500 Cases of Neurophysiological Monitoring in Carotid Endarterectomy", Acta Neurochir, 2007, 149:681-689.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).
Theron, et al. "New Triple Coaxial Catheter System for Carotid Angioplasty with Cerebral Protection" AJNR 11:869-874, Sep./Oct. 1990 0195-6108/90/1106-0869 @ American Society of Neurology.
Trevo ProVue Retriever. Stryker Trevo® ProVue™ Retrieval System (bu Concentric Medical®). (2016) Web. Apr. 13, 2018. 2 pages.
Turk, Aquilla S et al. (2014, e-published Apr. 27, 2013) "Initial clinical experience with the ADAPT technique: A direct aspiration first pass technique for stroke thrombectomy." J NeuroIntervent Surg 2014;6:231-237. doi:10.1136/neurintsurg-2013-010713. Web. Accessed Sep. 26, 2018.
Vijaywargiya et al. "Anatomical study of petrous and cavernous parts of internal carotid artery". Anatomy and Cell Biology 2017;50: 163-170. (Year: 2017).
Vuong, S. M. et al. (2017). "Application of emerging technologies to improve access to ischemic stroke care." Neurosurgical Focus, 42(4), E8. 7 pages. https://doi.org/10.3171/2017.1.FOCUS16520.
Webb et al. (1999). "Retrieval and Analysis of Particulate Debris After Saphenous Vein Graft Intervention," *Journal of the American College of Cardiology*, 34(2);468-475.
Yoo et al. (2012). "The Penumbra Stroke System: a technical review." *Journal of NeuroInterventional Surgery*. 4:199-205 (2012). Web. Downloaded Jun. 15, 2017.
Zuckerman, Bram. "Letter to Cathera Inc: Re K151638, Trade/Device Name: Phenom™ Catheters." Department of Health & Human Services, Nov. 13, 2015, 6 pages.
U.S. Appl. No. 16/596,535, filed Oct. 8, 2019, US 2020-0046940.
U.S. Appl. No. 16/925,708, filed Jul. 10, 2020, US 2020-0337716.
U.S. Appl. No. 17/152,581, filed Jan. 19, 2021, US 2021-0138194.
U.S. Appl. No. 17/481,639, filed Sep. 22, 2021, US 2022-0175565.
U.S. Appl. No. 17/883,430, filed Aug. 8, 2022, US 2022-0370761.
U.S. Appl. No. 18/067,666, filed Dec. 16, 2022, US 2023-0122587.
Fargen KM. (2021). "A unifying theory explaining venous sinus stenosis and recurrent stenosis following venous sinus stenting in patients with idiopathic intracranial hypertension." Journal of NeuroInterventional Surgery, 13(7):587-592. doi: 10.1136/neurintsurg-2020-017208. PMID: 33579755.
Mayfield Brain & Spine. (Jun. 2017). Stroke Care Enters New Era with World's First Use of Robot-Assisted Endovascular Neurosurgery by Mayfield and TriHealth Neuroscience Institute. Mayfield Clinic. Retrieved Aug. 22, 2023, from https://mayfieldclinic.com/mc_pr/pr_17june.htm 2 pages.
Narsinh, K.H. et al. (2022, first published online Aug. 16, 2021). "Robotics for neuroendovascular intervention: Background and primer." The Neuroradiology Journal. 2022;35(1):25-35. doi:10.1177/19714009211034829.
Nicholson, P. et al. (2019). "Venous sinus stenting for idiopathic intracranial hypertension: a systematic review and meta-analysis." Journal of Neurointerventional Surgery, 11(4):380-385. doi: 10.1136/neurintsurg-2018-014172. PMID: 30166333.
Stryker. (n.d.). Instructions For Use of the Surpass Evolve Flow Diverter System. Stryker Neurovascular. Retrieved [Jul. 31, 2023], from https://www.stryker.com/content/dam/stryker/neurovascular/products/surpass-evolve-flow-diverter/downloads/US_Surpass%20Evolve%20DFU%20.pdf, 1 page.
Tekle, W. G. & Hassan, A. E. (2021). "Intracranial Atherosclerotic Disease: Current Concepts in Medical and Surgical Management." Neurology, 97 (20 Suppl 2), S145-S157.
U.S. Appl. No. 18/297,429, filed Apr. 7, 2023, US 2023-0241347.
U.S. Appl. No. 16/584,351, filed Sep. 26, 2019, US 2020-0038628.
U.S. Appl. No. 16/890,962, filed Jun. 2, 2020, US 2020-0289136.
U.S. Appl. No. 17/011,448, filed Sep. 3, 2020, US 2021-0052296.
U.S. Appl. No. 17/089,495, filed Nov. 4, 2020, US 2021-0045758.
U.S. Appl. No. 17/093,401, filed Nov. 9, 2020, US 2021-0069467.
U.S. Appl. No. 17/319,943, filed May 13, 2021, US 2021-0259718.
U.S. Appl. No. 17/497,713, filed Oct. 8, 2021, US 2022-0111177.
U.S. Appl. No. 17/545,885, filed Dec. 8, 2021, US 2022-0096103.
U.S. Appl. No. 17/849,379, filed Jun. 24, 2022, US 2022-0313292.
U.S. Appl. No. 17/859,955, filed Jul. 7, 2022, US 2022-0338888.
U.S. Appl. No. 17/883,295, filed Aug. 8, 2022, US 2022-0370767.
U.S. Appl. No. 17/981,164, filed Nov. 4, 2022, US 2023-0059721.
U.S. Appl. No. 18/065,527, filed Dec. 13, 2022, US 2023-0248366.
U.S. Appl. No. 18/159,491, filed Jan. 25, 2023, US 2023-0165597.
U.S. Appl. No. 18/184,495, filed Mar. 15, 2023, US 2023-0293851.
U.S. Appl. No. 18/185,710, filed Mar. 17, 2023, US 2023-0277805.
U.S. Appl. No. 18/297,443, filed Apr. 7, 2023, US 2023-0241348.
U.S. Appl. No. 18/309,173, filed Apr. 28, 2023, US 2023-0277806.
U.S. Appl. No. 18/311,797, filed May 3, 2023, US 2023-0355255.
U.S. Appl. No. 18/311,802, filed May 3, 2023, US 2023-0355413.
U.S. Appl. No. 18/323,756, filed May 25, 2023, US 2023-0380915.
U.S. Appl. No. 18/350,533, filed Jul. 11, 2023, US 2024-0016633.
U.S. Appl. No. 18/369,695, filed Sep. 18, 2023, US 2024-0009425.
U.S. Appl. No. 18/485,168, filed Oct. 11, 2023, US 2024-0042170.
U.S. Appl. No. 18/514,553, filed Nov. 20, 2023, US 2024-0082542.
U.S. Appl. No. 16/584,351, filed Sep. 26, 2019.
U.S. Appl. No. 16/890,962, filed Jun. 2, 2020.
U.S. Appl. No. 17/011,448, filed Sep. 3, 2020.
U.S. Appl. No. 17/089,495, filed Nov. 4, 2020.
U.S. Appl. No. 17/093,401, filed Nov. 9, 2020.
U.S. Appl. No. 17/319,943, filed May 13, 2021.
U.S. Appl. No. 17/497,713, filed Oct. 8, 2021.
U.S. Appl. No. 17/545,885, filed Dec. 8, 2021.
U.S. Appl. No. 17/849,379, filed Jun. 24, 2022.
U.S. Appl. No. 17/859,955, filed Jul. 7, 2022.
U.S. Appl. No. 17/883,295, filed Aug. 8, 2022.
U.S. Appl. No. 17/981,164, filed Nov. 4, 2022.
U.S. Appl. No. 18/065,527, filed Dec. 13, 2022.
U.S. Appl. No. 18/159,491, filed Jan. 25, 2023.
U.S. Appl. No. 18/184,495, filed Mar. 15, 2023.
U.S. Appl. No. 18/185,710, filed Mar. 17, 2023.
U.S. Appl. No. 18/297,443, filed Apr. 7, 2023.

(56) References Cited

OTHER PUBLICATIONS

U.S. Appl. No. 18/309,173, filed Apr. 28, 2023.
U.S. Appl. No. 18/311,797, filed May 3, 2023.
U.S. Appl. No. 18/311,802, filed May 3, 2023.
U.S. Appl. No. 18/323,756, filed May 25, 2023.
U.S. Appl. No. 18/350,533, filed Jul. 11, 2023.
U.S. Appl. No. 18/369,695, filed Sep. 18, 2023.
U.S. Appl. No. 18/485,168, filed Oct. 11, 2023.
U.S. Appl. No. 18/514,553, filed Nov. 20, 2023.
U.S. Appl. No. 18/625,031, filed Apr. 2, 2024.
PCT/US2023/20868, May 3, 2023, WO 2023/215402.
PCT/US2023/20871, May 3, 2023, WO 2023/215403.
PCT/US2023/23574, May 3, 2023, WO 2023/230259.
PCT/US2023/27404, Jul. 11, 2023, WO 2024/015382.
PCT/US2023/64454, Mar. 15, 2023, WO 2023/178189.

\* cited by examiner

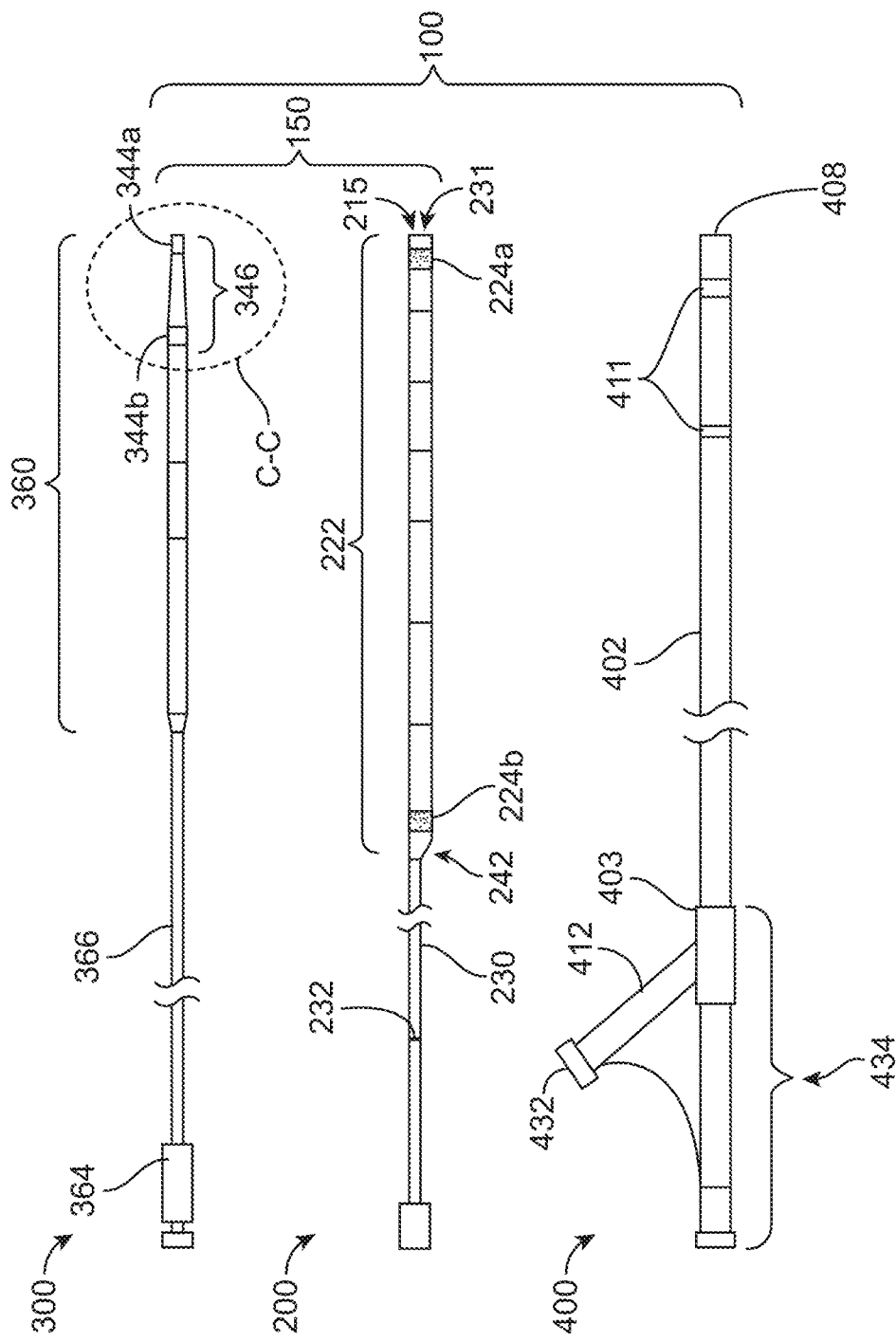

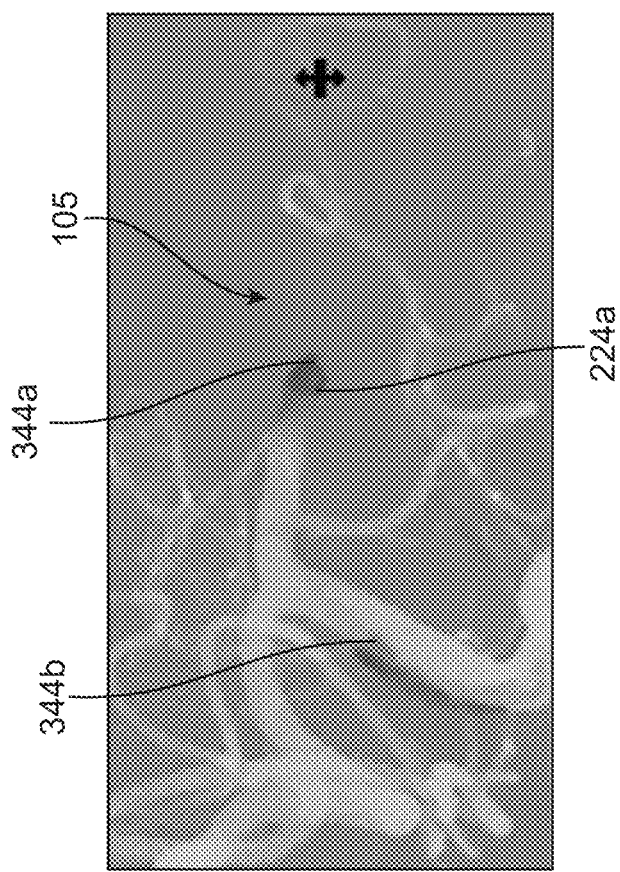
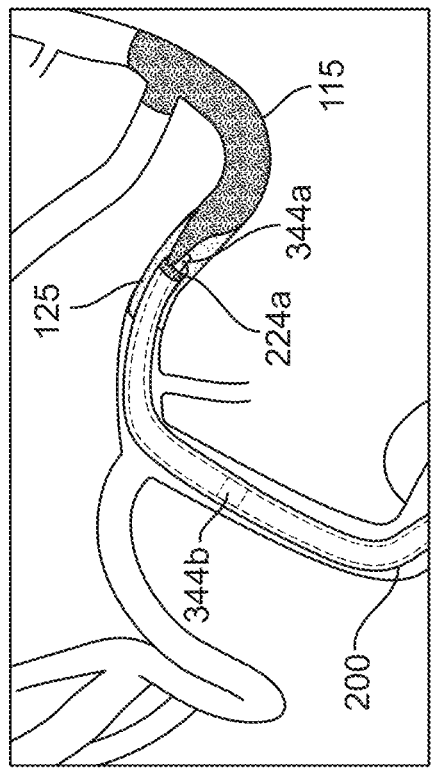
FIG. 7A
FIG. 7B

1400 ↘

```
┌──────────────────────────────────────────────────────────┐
│ Assemble catheter system comprising CAE that substantially│─ 1405
│    fills a catheter lumen along a length to create a     │
│                   piston arrangement                      │
└──────────────────────────────────────────────────────────┘
                            │
                            ▼
┌──────────────────────────────────────────────────────────┐
│         Advance catheter system towards occlusion site    │─ 1410
└──────────────────────────────────────────────────────────┘
                            │
                            ▼
┌──────────────────────────────────────────────────────────┐
│  Position tapered distal end region of CAE within occlusive│─ 1415
│              material at the occlusion site              │
└──────────────────────────────────────────────────────────┘
                            │
                            ▼
┌──────────────────────────────────────────────────────────┐
│                 Withdraw CAE through lumen                │─ 1420
└──────────────────────────────────────────────────────────┘
                            │
                            ▼
┌──────────────────────────────────────────────────────────┐
│  Piston arrangement creates an aspiration pressure at the │─ 1425
│   distal end of the catheter sufficient to draw a portion │
│      of the occlusive material into the catheter lumen    │
└──────────────────────────────────────────────────────────┘
```

FIG. 14

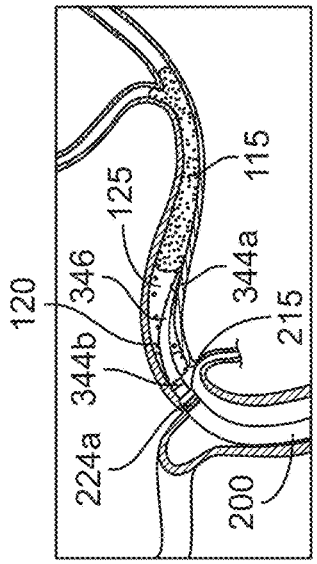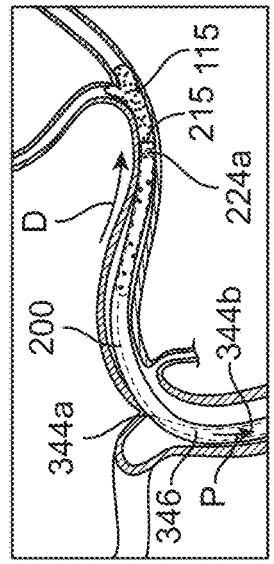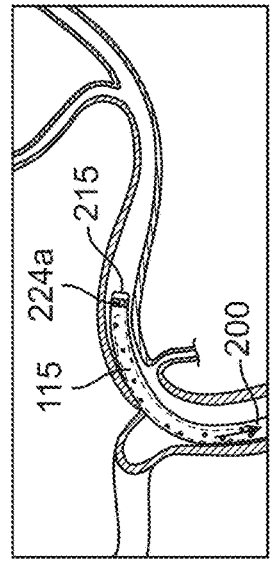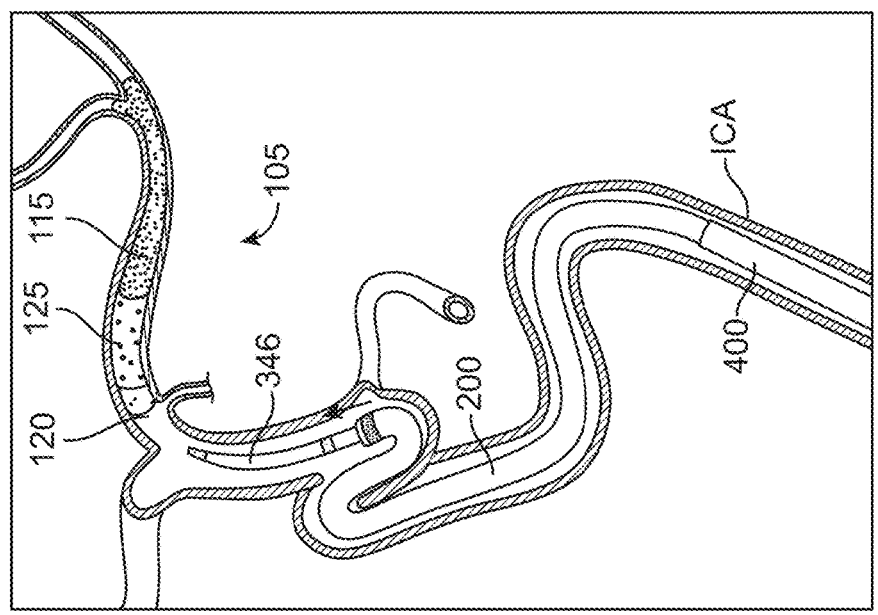

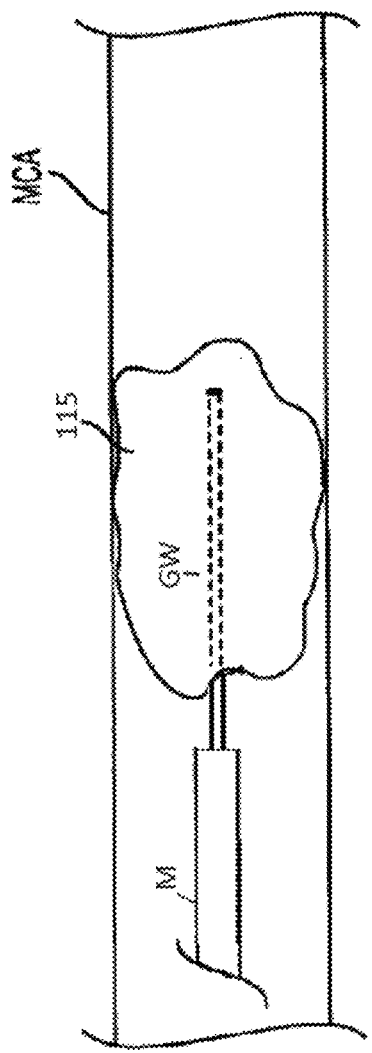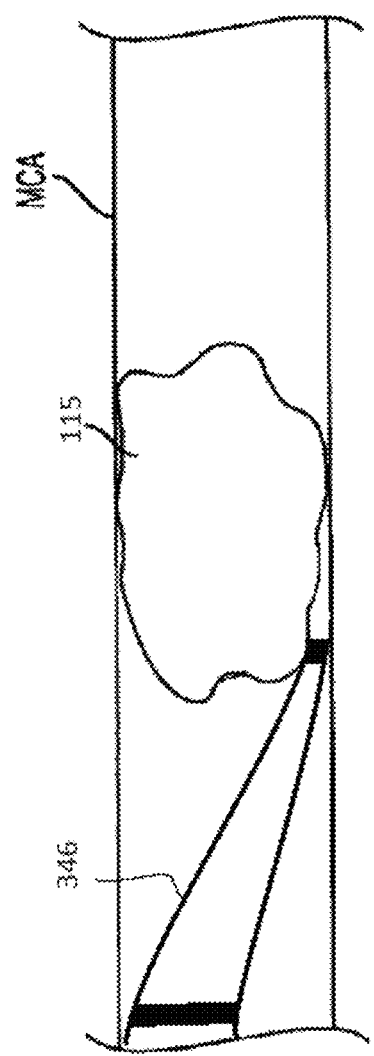

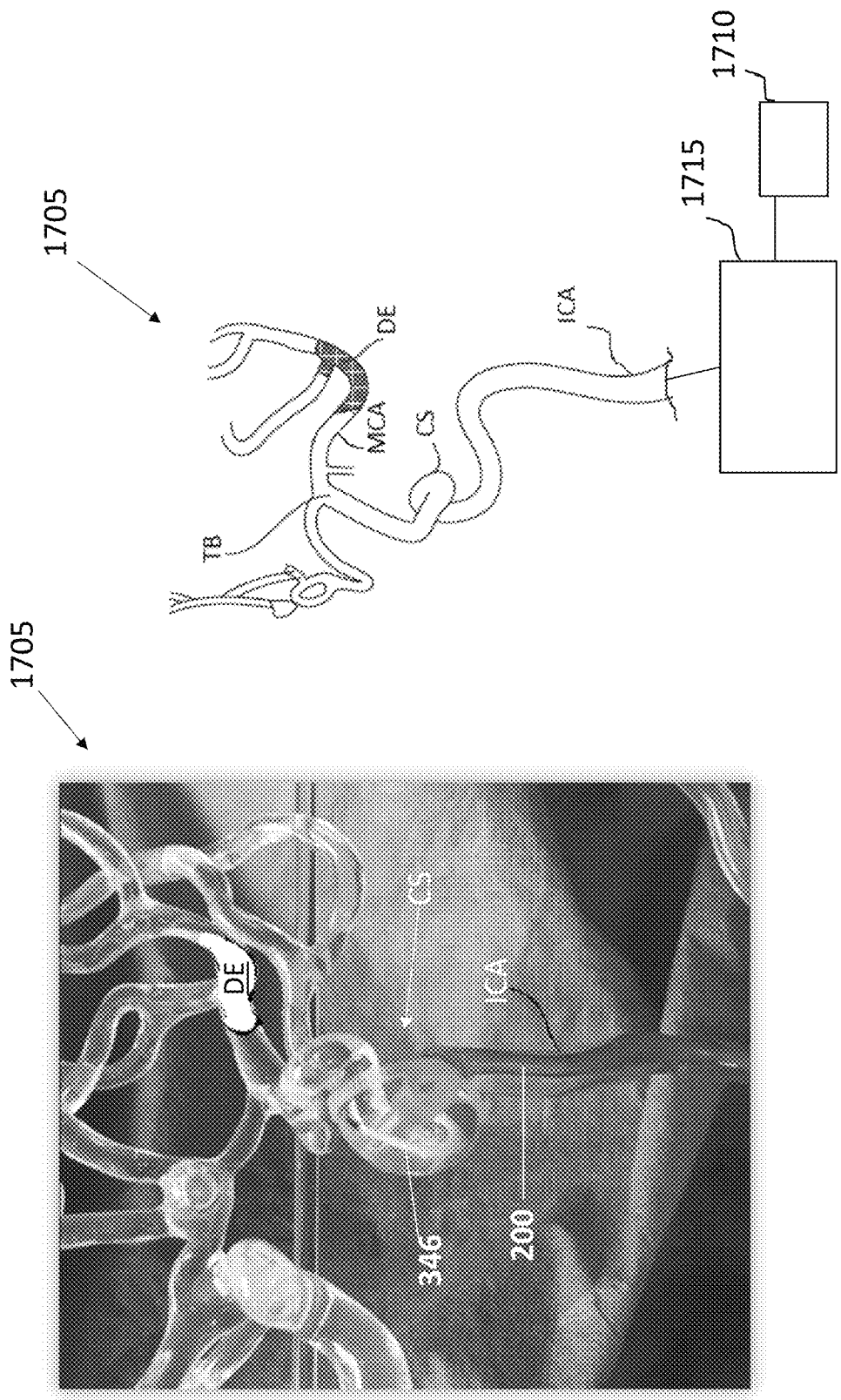

ASPIRATION CATHETER SYSTEMS AND METHODS OF USE

CROSS-REFERENCE TO PRIORITY DOCUMENT

This application is a continuation of U.S. patent application Ser. No. 17/497,713 filed Oct. 8, 2021, which claims the benefit of priority to U.S. Provisional Application Ser. No 63/089,987, filed Oct. 9, 2020. The full disclosure is incorporated herein by reference in their entirety.

BACKGROUND

The present disclosure relates generally to medical methods and devices for the treatment of acute ischemic stroke. More particularly, the present disclosure relates to methods and systems for effectively locating and removing cerebral occlusions.

Acute ischemic stroke is the sudden blockage of adequate blood flow to a section of the brain, usually caused by emboli lodging or thrombus forming in situ in one of the blood vessels supplying the brain. If this blockage is not quickly resolved, ischemia may lead to permanent neurologic deficit or death. The timeframe for effective treatment of stroke is within 3 hours for intravenous (IV) thrombolytic therapy and 6 hours for site-directed intra-arterial thrombolytic therapy or up to 8 hours for interventional recanalization of a blocked cerebral artery. Re-perfusing the ischemic brain after this time period has no overall benefit to the patient, and may in fact cause harm due to the increased risk of intracranial hemorrhage from fibrinolytic use. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death and the leading cause of serious, long-term disability in the United States.

Endovascular treatment of acute stroke is comprised of either the intra-arterial administration of thrombolytic drugs such as recombinant tissue plasminogen activator (rtPA), mechanical removal of the blockage, or a combination of the two. As mentioned above, these interventional treatments must occur within hours of the onset of symptoms. Both intra-arterial (IA) thrombolytic therapy and interventional thrombectomy (sometimes referred to as embolectomy) involve accessing the blocked cerebral artery via endovascular techniques and devices.

Like IV thrombolytic therapy, IA thrombolytic therapy alone has the limitation in that it may take several hours of infusion to effectively dissolve the clot. Interventional thrombectomy therapies have involved capturing and removing the clot using snares, coils or temporary stents (also known as retrievable stent devices), and suctioning the clot with or without adjunct disruption of the clot. Retrievable stent devices are also used to restore flow quickly to the vessel during the intervention. Hybrid procedures are also used, combining retrievable stent devices and aspiration via the guide catheter or via intermediate catheters to aid in the removal of the clot and reduce the risk of distal emboli. Finally, balloons or stents have been used to create a patent lumen through the clot when clot removal or dissolution was not possible.

Guide catheters or guide sheaths are used to guide interventional devices to access the cerebral anatomy and the target anatomy from an arterial access site, typically the femoral artery. Often, devices are used in a nested fashion, namely, a guidewire inside a microcatheter inside an intermediate catheter and are advanced as an assembly to the target site in a stepwise fashion with the inner, most atraumatic elements advancing distally first and providing support for advancement of the outer elements. The length of each element of the coaxial assemblage takes into account the length of the guide, the length of proximal connectors on the catheters, and the length needed to extend from the distal end.

Some exemplary issues with current technology include the ability to locate the interventional device at the site of the occlusion and optimized aspiration of the clot in a first attempt, while minimizing the chance of liberating emboli.

SUMMARY

Provided is a system of removing an embolus in a cerebral vessel of a patient with an assembled system of devices including a catheter having a catheter lumen and a distal end; and a catheter advancement element extending through the catheter lumen. The catheter advancement element comprises a lumen having a distal opening and a tapered distal end region. The tapered distal end region of the catheter advancement element extends distal to the distal end of the catheter. The assembled system of devices is configured for advancement together towards an occlusion site in a cerebral vessel of a patient visible on angiogram. The occlusion site includes an angiographic limit of contrast and an embolus downstream of the angiographic limit of contrast. The catheter advancement element tapered distal end region has a flexibility and taper configured to be delivered to a location past the angiographic limit of contrast without crossing the embolus.

The assembled system of devices can further include a guidewire having a distal end positioned within the lumen of the catheter advancement element and located a distance proximal to the distal opening of the catheter advancement element during advancement of the assembled system of devices together. The guidewire is extendable out the distal opening of the catheter advancement element for navigation. The distal end region of the catheter advancement element can taper distally from a first outer diameter to a second outer diameter that is smaller than the first outer diameter. The catheter advancement element can further include a proximal portion extending proximally from the catheter advancement element to outside the body of the patient. The proximal portion can have a single lumen that communicates with the lumen of the catheter advancement element. The tapered distal end region can be formed of a material having a material hardness of about Shore 62A and Shore 35D that transitions proximally towards increasingly harder materials. The tapered distal end region can taper over a length of 2 cm to 5 cm. The tapered distal end region can taper over a length of 0.05 cm to 2 cm. The tapered distal end region can taper along a distance that is between 1 cm and 3 cm. The first outer diameter can be at least 1.5 times the second outer diameter. The distal opening from the lumen of the catheter advancement element can have an inner diameter between 0.018" and 0.024". The second outer diameter is about 0.026" up to about 0.040". The first outer diameter can be about 0.062" up to about 0.080".

The catheter advancement element can include at least one radiopaque marker along its length. The catheter advancement can include at least one radiopaque marker identifying the tapered distal end region of the catheter advancement element. A first radiopaque marker can be disposed near the first outer diameter and a second radiopaque marker can be disposed near the second outer diameter. The catheter can include a flexible distal luminal portion and a proximal tether element extending proximally from a point of attachment near a proximal end of the flexible distal luminal portion. The proximal tether element can extend proximally to outside the body of the patient. An outer diameter of the proximal tether element near the point of attachment can be smaller than an outer diameter of the distal luminal portion near the point of attachment. The embolus has a proximal face, and the tapered distal end region can be configured to deflect upon contact with the proximal face of the embolus. The tapered distal end region can have a distal-facing contact surface sized to apply a force per unit area of about 2 N/mm$^2$ to about 4 N/mm$^2$ upon an applied force of 1 N. The taper of the distal end region can have a length of about 1 cm to about 5 cm from a proximal outer diameter between 1.58 mm and 2.03 mm to a distal outer diameter that is about 0.79 mm at the distal opening.

In an interrelated aspect, provided is a method of removing an embolus in a cerebral vessel of a patient including assembling a system of devices and advancing the assembled system of devices together towards an occlusion site in a cerebral vessel of a patient visible on angiogram, the occlusion site having an angiographic limit of contrast and an embolus downstream of the angiographic limit of contrast. The assembled system of devices includes a catheter having a catheter lumen and a distal end and a catheter advancement element extending through the catheter lumen. A tapered distal end region of the catheter advancement element extends distal to the distal end of the catheter. The method further includes advancing the catheter advancement element to a location past the angiographic limit of contrast without crossing the embolus, advancing the catheter over the catheter advancement element to position the distal end of the catheter at a treatment site located past the angiographic limit of contrast, and applying aspiration to the catheter.

Advancing the catheter advancement element can include positioning a distal end of the catheter advancement element between a portion of the embolus and a vessel wall. Advancing the catheter can include positioning the distal end of the catheter at a proximal face of the embolus. Positioning the distal end of the catheter at the proximal face of the embolus can compress the embolus. Advancing the catheter can include advancing the distal end of the catheter through a soft clot material proximal of the embolus to reach the proximal face of the embolus. Advancing the catheter can include positioning the distal end of the catheter past a proximal face of the embolus without crossing the embolus. Advancing the catheter advancement element can include positioning a distal end of the catheter advancement element without crossing the embolus with the distal end of the catheter advancement element. Advancing the catheter can include positioning the distal end of the catheter past the angiographic limit of contrast until resistance is felt indicating a proximal face of the embolus. The step of advancing the catheter advancement element can include advancing a distal end of the catheter advancement element as far as possible without buckling of the catheter advancement element. The step of advancing the catheter advancement element can include interrogating the treatment site to locate a proximal face of the embolus. The step of advancing the catheter advancement element can include using the tapered distal end region of the catheter advancement element to dissect past a soft clot material at a proximal face of the embolus and probe denser material of the embolus.

The method can further include remove the catheter advancement element after the catheter is at the treatment site. The method can further include capturing occlusive material while applying the aspiration at, within, or through the distal end of the catheter. The method can further include injecting contrast agent into the cerebral vessel to visualize the occlusion site by angiogram. The contrast agent can form a plurality of visible zones. A first zone of the plurality of visible zones can include a high contrast region located proximal to the angiographic limit of contrast. The high contrast region can identify blood flow through the cerebral vessel. A second zone of the plurality of visible zones can include a low contrast region located distal to the angiographic limit of contrast. The low contrast region can infiltrate slowly or minimally with contrast. The low contrast region can identify a location of the embolus and/or soft clot material proximal of the location of the embolus. The step of advancing the catheter advancement element can include positioning a distal end of the catheter advancement element past the low contrast region and positioning the distal end of the catheter can include positioning the distal end of the catheter past the low contrast region.

The distal end region of the catheter advancement element can taper distally from a first outer diameter to a second outer diameter that is smaller than the first outer diameter. The catheter advancement element can further include a proximal portion extending proximally from the catheter advancement element to outside the body of the patient. The proximal portion can have a single lumen that communicates with a lumen of the catheter advancement element. The distal end region can be formed of a material having a material hardness of about Shore 62A and Shore 35D that transitions proximally towards increasingly harder materials. The distal end region can taper over a length of 2 cm to 5 cm. The distal end region can taper over a length of 0.05 cm to 2 cm. The distal end region can taper along a distance that is between 1 cm and 3 cm.

A guidewire can be positioned within the lumen of the catheter advancement element such that a distal end of the guidewire is within the catheter advancement element during the step of advancing the assembled system of devices together and is extendable from the catheter advancement element when needed for navigation. The first outer diameter can be at least 1.5 times the second outer diameter. A distal opening from the lumen of the catheter advancement element can have an inner diameter between 0.018" and 0.024". The second outer diameter can be about 0.026" up to about 0.040". The first outer diameter can be about 0.062" up to about 0.080". The catheter advancement element can include at least one radiopaque marker along its length. The catheter advancement element can include at least one radiopaque marker identifying the distal end region of the catheter advancement element. A first radiopaque marker can be disposed near the first outer diameter and a second radiopaque marker can be disposed near the second outer diameter. The catheter can include a flexible distal luminal portion and a proximal tether element extending proximally from a point of attachment near a proximal end of the flexible distal luminal portion, the proximal tether element extending proximally to outside the body of the patient. An outer diameter of the proximal tether element at the point of attachment can be smaller than an outer diameter of the distal luminal portion at the point of attachment. The assembled system of devices can further include a guidewire positioned within the lumen of the catheter advancement element during the advancing step. The guidewire can be positioned within the lumen of the catheter advancement element such that a distal end of the guidewire protrudes from a distal end of the catheter advancement element during at least one of the advancing steps.

In an interrelated implementation, provided is a method of removing an embolus in a cerebral vessel of a patient including assembling a system of devices and advancing the assembled system of devices together towards an occlusion site in a cerebral vessel of a patient visible on angiogram, the occlusion site having an angiographic limit of contrast and an embolus downstream of the angiographic limit of contrast. The assembled system of devices includes a catheter having a catheter lumen and a distal end; and a catheter advancement element extending through the catheter lumen. A tapered distal end region of the catheter advancement element extends distal to the distal end of the catheter. The method further includes advancing the catheter advancement element to a location past the angiographic limit of contrast without crossing the embolus; advancing the catheter to position the distal end of the catheter at a treatment site located past the angiographic limit of contrast; and applying aspiration to the catheter.

The method can further include withdrawing the catheter advancement element relative to the catheter. The method can further include automatically creating vacuum within the catheter due to withdrawing the catheter advancement element. The vacuum automatically created can occur prior to applying aspiration to the catheter. The step of advancing the catheter can include advancing the catheter to a first location and then allowing the distal end of the catheter to passively move in a distal direction to the treatment site driven by release of forces stored in the system of device due to withdrawing the catheter advancement element. Allowing the distal end of the catheter to passively advance in the distal direction seats the distal end of the catheter against a proximal face of the embolus. The method can further include applying a force on the catheter to advance the catheter to the first location. The force can be applied manually or automatically. The first location can be past the angiographic limit of contrast. The method can further include automatically creating vacuum within the catheter due to withdrawing the catheter advancement element. The vacuum automatically created can occur prior to applying aspiration to the catheter. The step of advancing the catheter advancement element can include positioning a distal end of the catheter advancement element between a portion of the embolus and a vessel wall. The step of advancing the catheter can include positioning the distal end of the catheter at a proximal face of the embolus. Positioning the distal end of the catheter at the proximal face of the embolus can compress the embolus. The step of advancing the catheter can include advancing the distal end of the catheter through a soft clot material proximal of the embolus to reach the proximal face of the embolus. The step of advancing the catheter can include positioning the distal end of the catheter past a proximal face of the embolus without crossing the embolus. The step of advancing the catheter advancement element can include advancing a distal end of the catheter advancement element as far as possible without buckling of the catheter advancement element.

The distal end region of the catheter advancement element can taper distally from a first outer diameter to a second outer diameter that is smaller than the first outer diameter. The catheter advancement element can further include a proximal portion extending proximally from the catheter advancement element to outside the body of the patient, the proximal portion having a single lumen that communicates with a lumen of the catheter advancement element. The distal end region can taper over a length of 2 cm to 5 cm. The distal end region can taper over a length of 0.05 cm to 2 cm. The distal end region can taper along a distance that is between 1 cm and 3 cm. A guidewire can be positioned within the lumen of the catheter advancement element such that a distal end of the guidewire is within the catheter advancement element during the step of advancing the assembled system of devices together and is extendable from the catheter advancement element when needed for navigation. The first outer diameter can be at least 1.5 times the second outer diameter.

The method can further include removing the catheter advancement element before the catheter is at the treatment site. The method can further include capturing occlusive material at, within, or through the distal end of the catheter while removing the catheter advancement element. The step of capturing occlusive material at, within, or through the distal end of the catheter can occur before the step of applying aspiration to the catheter. The step of applying aspiration to the catheter can be performed through a rotating hemostatic valve (RHV) of a base sheath through which the system of devices is positioned. The step of applying aspiration to the catheter can be performed by removing the catheter advancement element. The method can further include a second step of applying aspiration to the catheter that is performed through an RHV of a base sheath through which the system of devices is positioned. The method can further include injecting contrast agent into the cerebral vessel to visualize the occlusion site by angiogram. The contrast agent can form a plurality of visible zones having a high contrast region located proximal to the angiographic limit of contrast. The high contrast region can identify blood flow through the cerebral vessel. The plurality of visible zone can also include a low contrast region located distal to the angiographic limit of contrast. The low contrast region can infiltrate slowly or minimally with contrast and identify a location of the embolus and/or soft clot material proximal of the location of the embolus. Advancing the catheter advancement element can include positioning a distal end of the catheter advancement element past the low contrast region. Positioning the distal end of the catheter can include positioning the distal end of the catheter past the low contrast region.

In an interrelated aspect, provided is a method of treating a cerebral vessel of a patient including assembling a system of devices and advancing the assembled system of devices together towards an occlusion site having occlusive material lodged in a cerebral vessel of a patient. The assembled system of devices includes a catheter having a catheter lumen and a distal end; and a catheter advancement element extending through the catheter lumen. A tapered distal end region of the catheter advancement element extends distal to the distal end of the catheter. The catheter advancement element substantially fills the catheter lumen along a length to create a piston arrangement. The method includes advancing the catheter to position the distal end of the catheter at a first location relative to the occlusion site; withdrawing the catheter advancement element through the catheter lumen with a velocity that the piston arrangement creates an aspiration pressure at the distal end of the catheter sufficient to draw the occlusive material into the catheter lumen; and applying further aspiration to the catheter with an external aspiration source to further aspirate the embolus.

The occlusive material can include dense embolus and less dense clot. The step of withdrawing the catheter advancement element can cause the catheter to advance and seat the distal end of the catheter against a proximal face of the embolus. The step of withdrawing the catheter advancement element can cause the catheter to move in a distal direction towards the occlusion site driven by release of forces stored in the system of devices during delivery. A combination of the aspiration pressure from withdrawing the catheter advancement element and distal motion of the catheter can cause the portion of the occlusive material to enter the catheter lumen. The step of withdrawing the catheter advancement element can occur prior to applying the further aspiration to the catheter with the external aspiration source. The occlusive material can include dense embolus and less dense clot. The method can further include removing the catheter advancement element before the distal end of the catheter is at the embolus. Withdrawing the catheter advancement element from the catheter lumen can include capturing occlusive material at, within, or through the distal end of the catheter while removing the catheter advancement element. The step of applying further aspiration to the catheter can be performed through an RHV of a base sheath through which the system of devices is positioned. A clearance between the catheter advancement element and the catheter lumen can be less than about 0.006" along the length to create the piston arrangement. The length to create the piston arrangement can be at least 10 cm of the catheter length. The distal end region of the catheter advancement element can taper along a distance that is between 5 mm and 40 mm. The distal end region of the catheter advancement element can taper along a distance that is between 10 mm and 30 mm. The tapered distal end region of the catheter advancement element can taper from a first outer diameter to a second outer diameter at a distal tip. The first outer diameter can be at least 1.5 times the second outer diameter.

In an interrelated aspect, provided is a method of treating a cerebral vessel of a patient including assembling a system of devices and advancing the assembled system of devices together towards an occlusion site in a cerebral vessel of a patient visible on angiogram and positioning the tapered distal end region within occlusive material at the occlusion site. The assembled system of devices includes a catheter having a catheter lumen and a distal end; and a catheter advancement element extending through the catheter lumen. A tapered distal end region of the catheter advancement element extends distal to the distal end of the catheter. The catheter advancement element substantially fills the catheter lumen along a length to create a piston arrangement. The method includes withdrawing the catheter advancement element through the catheter lumen causing the piston arrangement to create an aspiration pressure at the distal end of the catheter sufficient to draw a portion of the occlusive material into the catheter lumen.

The occlusive material can include dense embolus and less dense clot. The step of withdrawing the catheter advancement element can cause the distal end of the catheter to advance and seat against a proximal face of the embolus. The step of withdrawing the catheter advancement element can cause the distal end of the catheter to move in a distal direction towards the occlusion site driven by release of forces stored in the system of devices during delivery. A combination of the aspiration pressure from withdrawing the catheter advancement element and distal motion of the distal end of the catheter causes the portion of the occlusive material to enter the catheter lumen. The method can further include a step of applying further aspiration to the catheter with an external aspiration source following the step of withdrawing the catheter advancement element. The step of applying further aspiration to the catheter can be performed through an RHV of a base sheath through which the system of devices is positioned. The method can further include removing the catheter advancement element before the distal end of the catheter is at a face of the embolus. A clearance between the catheter advancement element and the catheter lumen can be less than about 0.006" along the length to create the piston arrangement. The length to create the piston arrangement can be at least 10 cm of the catheter length. The distal end region of the catheter advancement element can taper along a distance that is between 5 mm and 40 mm. The distal end region of the catheter advancement element can taper along a distance that is between 10 mm and 30 mm. The tapered distal end region of the catheter advancement element can taper from a first outer diameter to a second outer diameter at a distal tip. The first outer diameter can be at least 1.5 times the second outer diameter.

BRIEF DESCRIPTION OF THE DRAWINGS

These and other aspects will now be described in detail with reference to the following drawings. Generally, the figures are not to scale in absolute terms or comparatively, but are intended to be illustrative. Also, relative placement of features and elements may be modified for the purpose of illustrative clarity.

FIG. 1A shows a catheter system for accessing an occlusion site in a cerebral vessel;

FIG. 7A shows an angiogram of the catheter system of FIG. 5A positioned with distal tip markers aligned;

FIG. 7B shows the angiogram of FIG. 7A in schematic;

FIG. 14 is a flow diagram of an interrelated implementation of a method of aspiration embolectomy in a cerebral vessel;

FIGS. 15A-15D show schematics of a method for removing an embolus using a catheter system that generates a piston effect;

FIG. 16A shows a schematic of a conventional guidewire centered by a microcatheter and penetrating an embolus;

FIG. 16B shows a schematic of a catheter advancement element positioned within a vessel and the tapered distal tip region deflecting upon reaching a proximal face of an embolus;

FIG. 17A shows an implementation of a test rig for assessing deflection of a tapered distal tip region upon reaching a proximal face of an embolus;

FIG. 17B is a schematic of an implementation of a test rig.

Figure 1B:
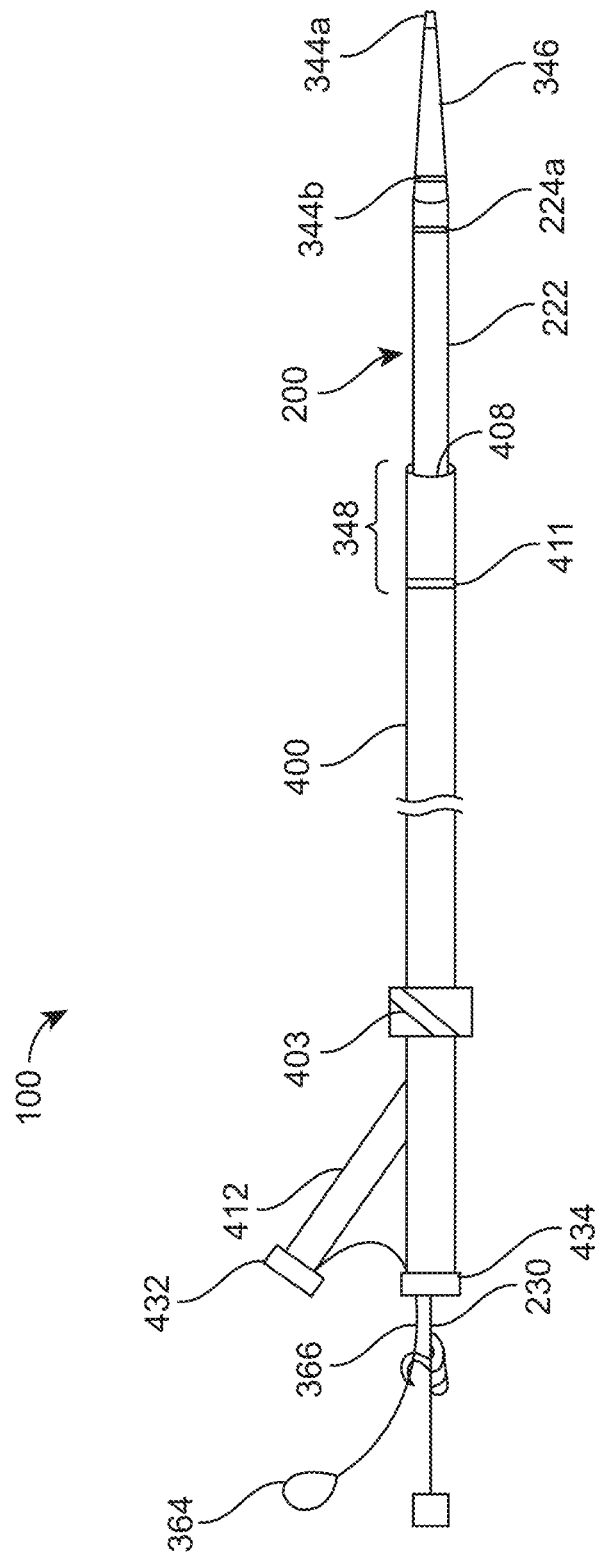
FIG. 1B shows the catheter system of FIG. 1A assembled.

It should be appreciated that the drawings are for example only and are not meant to be to scale. It is to be understood that devices described herein may include features not necessarily depicted in each figure.

DETAILED DESCRIPTION

One of the major drawbacks to current acute stroke intervention procedures is the amount of time required to restore blood perfusion to the brain. This time includes the time it takes to access the occlusive site or sites in the cerebral artery, and the time it takes to completely remove the occlusion from the artery. Typically, more than one attempt is made to completely remove the occlusion and each attempt is associated with potential procedural risk due to device advancement in the delicate cerebral vasculature. Reducing the number of attempts as well as reducing the time required to exchange devices for additional attempts are important factors in minimizing the overall time to perform a successful stroke intervention.

Repeated attempts also increase procedural risk to the medical staff. Determination of the location, size, and shape of a blockage is typically performed by fluoroscopic visualization after introduction of a radiopaque substance. Angiography is an industry standard for imaging vascular anatomy within the body. Angiography involves injection of contrast media and use of x-ray fluoroscopic imaging to visualize internal anatomy of the vasculature to evaluate blood flow, constrictions, or blockage, and to plan an appropriate treatment. Contrast media is introduced prior to or during imaging (intra-arterially or intravenously). The presence of the contrast media blocks or limits the ability of the x-rays to pass through. As a result, any region that temporarily contains the contrast media changes its appearance on the images. The x-ray angiography provides high resolution imaging showing the vasculature anatomical details.

Computed tomography (CT) is an imaging technique that combines data from serial x-ray slices to produce detailed 2D and 3D images of structures in the body. Computed tomography angiography (CTA) uses CT with contrast to visualize blood flow in arterial and venous vessels throughout the body. CTA combines the use of x-rays with computerized analysis of the images. Beams of x-rays are passed from a rotating device through the area of interest from several different angles to create cross-sectional images, which are assembled by computer into a three-dimensional picture of the area.

Magnetic resonance angiography (MRA) uses magnetic resonance imagining (MRI) to image blood vessels. MRA is divided into two categories depending on whether contrast media is used to enhance the image. Gadolinium is a paramagnetic contrast material that can be given prior to imaging to make the MRI images even clearer. Gadolinium alters magnetic properties of nearby hydrogen nuclei to enhance the quality of the MR images. MRO may use flow-related enhancement (e.g., 2D and 3D time-of-flight sequences), in which most of the signal on an image is due to blood that has recently moved into that plane. MRA may also use fast low angle shot magnetic resonance imaging (FLASH MRI).

Digital subtraction angiography (DSA) is an imaging method that permits direct visualization of the vasculature in skeletal or dense soft tissue environment. The target tissue is exposed to x-ray or MRI to obtain a first set of images. A contrast media is administered into the vasculature and additional x-ray or MRI are performed. The first set of images is overlaid and subtracted from the second set of images acquired using contrast allowing for visualization of the vascular structure free of the surrounding tissue.

Other imaging techniques include Positron Emission Tomography (PET), Ultrasound imaging, and Optical imaging. Photoacoustic imaging (PAI) is based on exciting a tissue of interest by a pulsed laser and thermal excitation of locally absorbed light leading to an expansion of the tissue and subsequent generation of ultrasonic waves. Ultrasonic transducers detect the emitted ultrasonic waves that are converted into images. Trans-cranial Doppler (TCD) is a non-invasive technique that involves the use of a low-frequency transducer probe to insonate specific areas of the cranium that are relatively thin. Cerebral blood flow velocity and vessel pulsatility may be monitored through an intact skull.

Contrast media typically includes iodine, or more rarely barium-sulphate, which absorb external x-rays resulting in decreased exposure on the x-ray detector. Iodinated contrast is typically used for angiography and CTA and is typically divided into two types: ionic and non-ionic. Examples of ionic contrast media include sodium methylglucamine diatrizoate (Renografin 76). Examples of a non-ionic media include iohexol 240, Iopromide 240, iohexol 300, iopromide 300, iohexol 350, iopromide 370, iodixanol 270, iopromide 320. Iopromide is sold under the brand name ULTRAVIST, iohexol is sold under the brand name OMNIPAQUE, and iodixanol is sold under the brand name VISIOPAQUE. Newer iodinated contrast media include low-osmolar ionic (LOCM) and iso-osmolar (IOCM). Iodinated LOCM, most of which are nonionic media, are associated with less discomfort and lower incidence of adverse effects. Magnetic resonance imaging uses gadolinium-based contrast media.

Although contrast media is considered generally safe, patients may experience allergic reactions and relatively severe adverse reactions do occur. Repeated x-ray imaging increases the overall radiation exposure to patients and medical staff. Thus, there is a need to reduce the number of attempts and time required to perform a successful stroke intervention that, in turn, results in fewer contrast media injections and lowers radiation exposure of medical staff and patients.

The various imaging techniques have improved the likelihood that an aspiration catheter system will be properly positioned near enough to the embolus that aspiration-only embolectomy is effectively performed. Even with imaging, surgeons may not know exactly where the embolus is located within the vessel. An embolus is a term that can be used to describe a thrombus (a clot of blood) that formed at a first blood vessel location (e.g., a coronary vessel), breaks loose, and travels through the circulation to a second blood vessel location (e.g., a cerebral vessel). Not every embolus originates as a thrombus (e.g., a foreign object or a gas), but once a thrombus travels from its place of origin it becomes an embolus. The embolus lodges within the second vessel location and disrupts and/or blocks blood flow distal to the embolus creating an occlusion within the second vessel location. The embolus can be relatively dense. This relatively dense embolus material that traveled through the circulation from another location to create an occlusion in a new vessel is sometimes referred to as an organized embolus.

Blood cells can accumulate at the proximal face of the embolus where there is disrupted or stagnated blood flow. The blood cells accumulate and form in situ a very soft and fluid-like thrombotic clot region in front of or proximal to the embolus. This soft thrombotic clot can become denser over time, but is generally less dense than the adjacent embolus. Thus, an occlusion site within a vessel can have zones of different consistency (e.g., dense vs. soft or organized vs. disorganized).

Contrast media interacts with these zones of different consistency in different ways. Contrast media may partly or fully infiltrate the disorganized in situ clot material, but generally does not infiltrate the dense embolus where flow is fully occluded creating different visible zones on angiogram. As mentioned above, an angiogram involves the use of x-rays to visualize the contrast media injected into the vasculature. Blood vessels normally cannot be seen in an x-ray. The contrast media injected into the vessels flows through the vessels substantially replacing the blood and absorbs the x-rays. Blood vessels containing the contrast media shows up on the x-ray as a high contrast region. These high contrast zones can look very dark on an x-ray (or very light if the x-ray image is inverted). An occlusion site in a vessel may be located on the angiogram due to the lack of contrast media infiltration. For example, contrast media may not infiltrate a dense embolus that completely occludes a vessel or may only minimally infiltrate the embolus. This creates an angiographic limit of contrast that is visible on the angiogram. A high contrast region may be located proximal (upstream) to the angiographic limit of contrast and the embolus (with or without soft clot material accumulated at the proximal face) may be located distal (downstream) to the angiographic limit of contrast. The soft clot material accumulated at the proximal face of the embolus may form another visible zone on the angiogram that is distinguishable from the high contrast region and the low contrast region. Contrast media may partially infiltrate this soft clot material and appear as a diffuse contrast region with a hazy appearance due to incomplete penetration of the contrast media that may include a combination of slow flowing blood and clot. This diffuse contrast region is distinguishable from the high contrast region and the low contrast region.

The embolus may be located immediately adjacent the distal-most limit of the contrast agent visible by angiogram or the embolus may be much deeper than the contrast limit. With no definition of anatomy and understanding of the acute event, the surgeon cannot define a target location for engagement by a catheter. Surgeons tend to err on the side of caution and advance the aspiration catheter to a location that can be confirmed by imaging as proximal of the embolus. In a patient where the embolus is deeper (i.e., further distal) than this contrast limit, placing the aspiration catheter at or near the angiographic limit of contrast may be too far away from the dense embolus to effectively remove it with aspiration-only embolectomy. The high aspiration forces at the distal end of the catheter are too far removed from the proximal face of the embolus to effectively capture it. In stent retriever embolectomy, placement of the stent retriever too far distally can also fail to effectively remove the entire embolus requiring repeated attempts.

The proximal face of the embolus, as well as the distal end of the embolus, are often not identifiable angiographically because the proximal face and the distal end are located within regions where contrast cannot penetrate. In addition, the shape of the embolus may be irregular and uneven which provides a further challenge in consistently seating or nesting a catheter distal end onto the embolus. A prior CT scan may be useful to identify the locations of the proximal and distal margins of the embolus as well as the length of the embolus. In some cases, additional information about the location of the distal end of the embolus can be seen on an angiogram due to collateral retrograde flow of contrast. The methods described herein provide techniques for the user to optimally place treatment systems with respect to the embolus in view of these embolus visualization challenges.

Disclosed herein are methods and devices that enable safe and rapid location of an embolus for optimum positioning of an aspiration catheter distal opening or other interventional device at the embolus to increase the rate of "one-pass" aspiration-only embolectomy. In addition to reducing procedure time and achieving blood flow restoration more quickly, one-pass embolectomy also lowers the overall radiation exposure of medical staff and patients and reduces the need for multiple contrast injections.

It has been found in performing the novel methods described herein that a novel structure is desirable to extend the range of applications of a conventional catheter to these novel treatment approaches. Provided herein are systems including a catheter advancement element having a tapered distal end region with a flexibility, shape, and taper length configured to be delivered to a location past the angiographic limit of contrast so as to atraumatically probe and find a true proximal face of an embolus without crossing the embolus. This is not achieved with conventional catheter systems as they may have improper flexibility, are formed of improper materials, or have improper shape and/or taper length resulting in conventional catheter systems embedding into the embolus or, if more force is applied, penetrating clear through and/or displacing the embolus distally. Unlike these conventional catheter systems, the catheter systems described herein includes a catheter advancement element capable of probing and/or slipping under the proximal face of the embolus. The catheter systems described herein help locate the embolus in the novel manner of the methods provided herein.

The catheter advancement element described herein can pass through the disorganized thrombus or diffuse contrast region proximal to an embolus to atraumatically probe the true face of the organized embolus. Surgeons can observe the flexible tapered distal tip region of the catheter advancement element and the presence of deflection and/or buckling while maintaining a natural arc of the device. The distal tip region of the catheter advancement element probes the embolus so that pressure on the embolus is small and due to the extremely flexible tip does not cross the embolus. The probing of the embolus with the catheter advancement element allows the surgeon to more safely find the true proximal face of the embolus so that the aspiration catheter can be advanced over the catheter advancement element to an optimal suctioning location relative to the embolus. After advancement of the aspiration catheter, the aspiration catheter and the catheter advancement element can be positioned tip-to-tip with both tip markers nearly aligned with one another and past the angiographic limit of contrast. Further, due to the structure of the catheter advancement element relative to the aspiration catheter, withdrawal of the aspiration catheter can create a piston effect initiating vacuum of the thrombus and embolus into the aspiration catheter without use of a separate vacuum source. The piston effect aspiration caused by withdrawal of the catheter advancement element through the aspiration catheter lumen can create distal advancement forces on the aspiration catheter as thrombotic material is aspirated into the aspiration catheter and removed from the vessel. Conventionally, surgeons would counteract these distal advancement forces by withdrawing the catheter slightly from the proximal end to avoid changing the distal tip position. The novel methods described herein allow for the aspiration catheter to ride out these distal advancement forces caused by withdrawal of the catheter advancement element so that the distal tip of the aspiration catheter passively moves further toward and against the embolus. The aspiration catheter engages the intact embolus, rather than the disorganized thrombotic material within the diffuse contrast region proximal to the embolus. Full aspiration can then be initiated to achieve a consistent first pass reperfusion and ingestion of the thrombotic material and the embolus within the aspiration catheter. The catheter advancement element is capable of allowing even aspiration catheters of conventional designs and sizing to achieve such results. These and other features will be described in detail herein.

As used herein, "embolus" or "embolus material" or "embolic material" or "embolic region" refers to material within a zone of an occlusion site that is more dense or a relatively hard consistency that is preferably placed in contact with a distal end of an aspiration catheter to successfully perform aspiration embolectomy. As described above, the embolus is a thrombus (a clot of blood) or other material that formed at a first blood vessel location (e.g., a coronary vessel), breaks loose, and travels through the circulation to a second blood vessel location. The "proximal face" of the embolus as used herein generally refers to a contour of the embolus on an upstream side of the occlusion that is available for capture by the aspiration catheter advanced towards the embolus from an upstream direction.

As used herein, "in situ thrombus" or "thrombus material" or "thrombotic material" or "thrombotic region" or "in situ clot material" or "clot material" refers to material within a zone of an occlusion site that accumulates in situ proximal the site of the embolus and is often less dense or relatively soft and fluid-like.

As used herein, "organized thrombus" refers to in situ thrombus material or clot material that accumulates proximal to the site of embolus and is more dense and less fluid-like than the in situ clot material.

As used herein, "an occlusion" or "an occlusion site" or "occlusive material" refers to the blockage that occurred as a result of an embolus lodging within a vessel and disrupting blood flow through the vessel. The occlusion or occlusive material can include both thrombus and embolus.

Reference to "angiogram" or "angiographic" is not limited to any particular form of imaging of the vessel and occlusion site and is intended to refer to any type of imaging technique used to identify an occlusion within a vessel. Similarly, reference to "contrast agent" or "contrast media" or just "contrast" is not limited to any particular agent used for imaging of the vessel and identification of an occlusion site and is intended to refer to any material for use in any type of imaging technique that aids in identifying an occlusion within a vessel. The angiogram provides the user with a roadmap through the vasculature to the treatment site.

System Components

The catheter systems described herein can be used for treating various neurovascular pathologies, such as acute ischemic stroke (AIS). The systems described herein provide quick and simple single-operator access to distal target anatomy, in particular tortuous anatomy of the cerebral vasculature at a single point of manipulation. The medical methods, devices and systems described herein allow for navigating complex, tortuous anatomy to perform rapid and safe aspiration and removal of cerebral occlusions for the treatment of acute ischemic stroke. The medical methods, devices and systems described herein can also be used to deliver intracranial medical devices, with or without aspiration for the removal of cerebral occlusions in the treatment of acute ischemic stroke. The systems described herein can be particularly useful for the treatment of AIS whether a user intends to perform aspiration alone as a frontline treatment for AIS. Further, the extreme flexibility and deliverability of the distal access catheter systems described herein allow the catheters to take the shape of the tortuous anatomy rather than exert straightening forces creating new anatomy. The distal access catheter systems described herein can pass through tortuous loops while maintaining the natural curves of the anatomy therein decreasing the risk of vessel straightening. The distal access catheter systems described herein can thereby create a safe conduit through the neurovasculature maintaining the natural tortuosity of the anatomy for other catheters to traverse (e.g. larger bore aspiration catheters).

While some implementations are described herein with specific regard to accessing a neurovascular anatomy for application of aspiration, the systems and methods described herein should not be limited to this and may also be applicable to other uses. For example, the catheter systems described herein may be used to deliver working devices to a target vessel of a coronary anatomy or other vasculature anatomy. Where the phrase "distal access catheter" or "aspiration catheter" is used herein that the catheter can be used for aspiration, the delivery of fluids to a treatment site or as a support catheter, or distal access providing a conduit that facilitates and guides the delivery or exchange of other devices such as a guidewire or interventional devices such as stent retrievers. Alternatively, the access systems described herein may also be useful for access to other parts of the body outside the vasculature.

The devices and systems described herein are related to and can be used in combination and in the alternative with the devices and systems described in U.S. Pat. No. 10,327,790, filed Aug. 3, 2012; U.S. Pat. No. 9,561,345, filed Dec. 19, 2014; U.S. Pat. No. 9,820,761, filed Feb. 4, 2016; U.S. Publication No. 2018/0193042, filed on Jan. 9, 2018; U.S Publication No. 2018/0361114, filed on Jan. 19, 2018; U.S. Publication No. 2019/0351182, filed May 16, 2019; U.S. application Ser. No. 16/684,324, filed Nov. 14, 2019; and U.S. Publication No. 2020/0289136, filed Jun. 2, 2020. The disclosures of each of these publications and applications are incorporated by reference herein in their entireties.

Figure 1C:
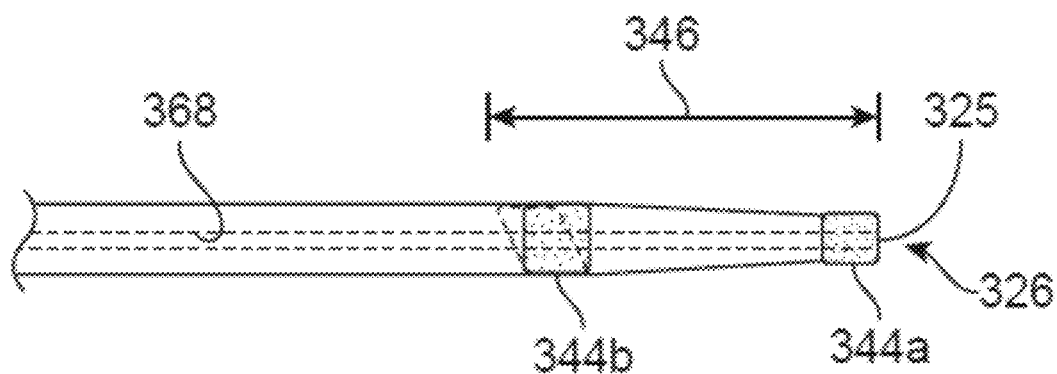
FIG. 1C is a detail view of a distal end region of a catheter advancement element.
Figure 1D:
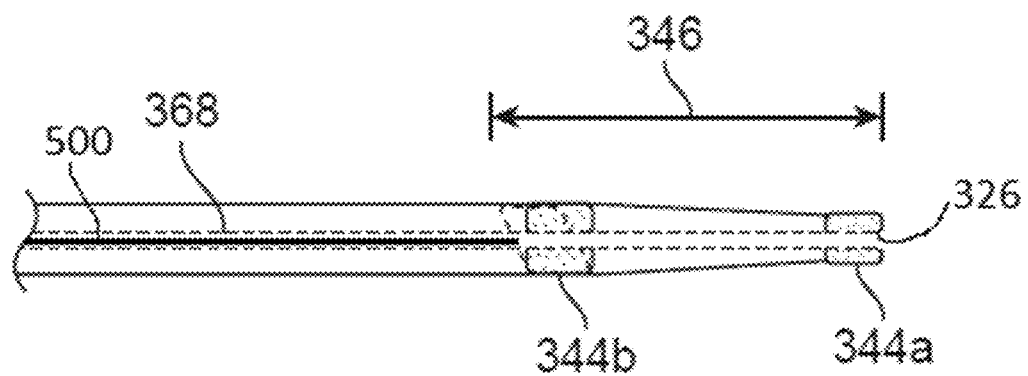
FIG. 1D is a detail view of a distal end region of a catheter advancing element having a rescue guidewire parked proximal of the distal opening.

FIGS. 1A-1B illustrate an implementation of a distal access system 100 including devices for accessing and removing a cerebral occlusion to treat acute ischemic stroke. FIG. 1A is an exploded view of an implementation of a catheter system and FIG. 1B is an assembled view of the catheter system of FIG. 1A. FIG. 1C is a detailed view of the catheter advancement element of FIG. 1A taken along circle C-C. FIG. 1D is a detailed view of a catheter advancement element having a parked guidewire 500 in the lumen 368 having a distal end of the guidewire 500 positioned proximal to the distal opening 326 of the lumen 368. The distal access system 100 is capable of providing quick and simple access to distal target anatomy, particularly the tortuous anatomy of the cerebral vasculature. The system 100 can be a single operator system such that each of the components and systems can be delivered and used together by one operator through a single point of manipulation requiring minimal hand movements. As will be described in more detail below, all wire and catheter manipulations can occur at or in close proximity to a single rotating hemostatic valve (RHV) or more than a single RHV co-located in the same device.

The system 100 can include one or more catheter systems 150, each having a catheter 200 and a catheter advancement element 300. The catheter system 150 is configured to be advanced through an access guide sheath 400. The catheter 200 is configured to be received through the guide sheath 400 and is designed to have exceptional deliverability. The catheter 200 can, but need not, be a spined, distal access catheter co-axial with a lumen of the guide sheath 400 thereby providing a step-up in inner diameter within the conduit. The catheter 200 can be delivered using a catheter advancement element 300 inserted through a lumen 223 of the catheter 200. The flexibility and deliverability of the distal access catheter 200 allow the catheter 200 to take the shape of the tortuous anatomy and avoids exerting straightening forces creating new anatomy. The distal access catheter 200 is capable of this even in the presence of the catheter advancement element 300 extending through its lumen. Thus, the flexibility and deliverability of the catheter advancement element 300 is on par or better than the flexibility and deliverability of the distal luminal portion 222 of the distal access catheter 200 in that both are configured to reach the middle cerebral artery (MCA) circulation without straightening out the curves of the anatomy along the way.

The system 100 can be a distal access system that can create a variable length from point of entry at the percutaneous arteriotomy (e.g. the femoral artery or other point of entry) to the target control point of the distal catheter. Conventional distal access systems for stroke intervention typically include a long guide sheath or guide catheter placed through a shorter "introducer" sheath (e.g. 11-30 cm in length) at the groin. The long guide sheath is typically positioned in the ICA to support neurovascular interventions including stroke embolectomy (sometimes referred to as "thrombectomy"). For added support, these can be advanced up to the bony terminal petrous and rarely into the cavernous or clinoid or supraclinoid terminal ICA when possible. To reach targets in the M1 or M2 distribution for ADAPT/MAT or Solumbra/SMAT approaches, an additional catheter may be inserted through the long guide catheter. These catheters are typically large-bore aspiration catheters that can be, for example 130 cm in length or longer. As will be described in more detail below, the distal access systems 100 described herein can be shorter, for example, only 115 cm in length when taken as a system as measured from the access point, typically the common femoral artery. Additionally, the single operator can use the systems described herein by inserting them through a single rotating hemostatic valve (RHV) 434 on the guide sheath 400 or more than one RHV co-located in the same device such as a dual-headed RHV. Thus, what was once a two-person procedure can be a one-person procedure.

Still with respect to FIGS. 1A-1B, the distal access system 100 can include an access guide sheath 400 having a body 402 through which a working lumen extends from a proximal hemostasis valve 434 coupled to a proximal end region 403 of the body 402 to a distal opening 408 of a distal end region. The working lumen is configured to receive the catheter 200 therethrough such that a distal end of the catheter 200 can extend beyond a distal end of the sheath 400 through the distal opening 408. The guide sheath 400 can be used to deliver the catheters described herein as well as any of a variety of working devices known in the art. For example, the working devices can be configured to provide thrombotic treatments and can include large-bore catheters, aspiration embolectomy (sometimes referred to as thrombectomy), advanced catheters, wires, balloons, retrievable structures such as coil-tipped retrievable stents "stent retriever".

The sheath body 402 can extend from a proximal furcation or rotating hemostatic valve (RHV) 434 at a proximal end region 403 to a distal end 408 of the body 402. The proximal RHV 434 may include one or more lumens molded into a connector body to connect to the working lumen of the body 402 of the guide sheath 400. The working lumen can receive the catheter 200 and/or any of a variety of working devices for delivery to a target anatomy. The RHV 434 can be constructed of thick-walled polymer tubing or reinforced polymer tubing. The RHV 434 allows for the introduction of devices through the guide sheath 400 into the vasculature, while preventing or minimizing blood loss and preventing air introduction into the guide sheath 400. The RHV 434 can be integral to the guide sheath 400 or the guide sheath 400 can terminate on a proximal end in a female Luer adaptor to which a separate hemostasis valve component, such as a passive seal valve, a Tuohy-Borst valve or RHV may be attached. The RHV 434 can have an adjustable opening that is open large enough to allow removal of devices that have adherent clot on the distal end 408 without causing the clot to dislodge at the RHV 434 during removal. Alternately, the RHV 434 can be removable such as when a device is being removed from the sheath 400 to prevent clot dislodgement at the RHV 434. The RHV 434 can be a dual RHV or a multi-head RHV.

The RHV 434 can form a Y-connector on the proximal end 403 of the sheath 400 such that the first port of the RHV 434 can be used for insertion of a working catheter into the working lumen of the sheath 400 and a second port into arm 412 can be used for another purpose. For example, a syringe or other device can be connected at arm 412 via a connector 432 to deliver a forward drip, a flush line for contrast agent or saline injections through the body 402 with or without a catheter toward the distal end 408 and into the target anatomy. Arm 412 can also connect to a vacuum source. The vacuum source can be an active source of aspiration such as an aspiration pump, a regular or locking syringe, a hand-held aspirator, hospital suction, or the like, configured to draw suction through the working lumen. In an embodiment, vacuum source is a locking syringe (for example a VacLok Syringe) attached to a flow controller. The user can pull the plunger on the syringe back into a locked position while the connection to the flow line is closed prior to an embolectomy step of the procedure. During the procedure when the distal-most end 215 of the catheter 200 is near or at the proximal face of the embolus 115 and the catheter advancement element 300 is removed from the lumen of the catheter 200, the user may open the connection to the aspiration syringe. This allows for a maximum communication of aspiration force being applied through the working lumen of the sheath 400 and any catheter extending through the sheath 400 that in turn is in communication with the vessel at its distal end. A single user at the single, shared source can apply the aspiration in a rapid fashion. In another implementation, the arm 412 can be connected to a vacuum source that is a pump configured to apply a constant or variable aspiration pressure through the working lumen of the guide sheath 400. The single, shared source of aspiration is sufficient to draw aspiration through the entire system 100, even when multiple aspiration catheters 200 are nested within one another through the working lumen of the guide sheath 400. The arm 412 can also allow the guide sheath 400 to be flushed with saline or radiopaque contrast agent during a procedure. The working lumen can extend from the distal end 408 to a working proximal port of the proximal end region 403 of the sheath body 402.

Contrast agent can be injected through the guide sheath 400 into the vessel to visualize the occlusion site by angiogram. For example, the guide sheath 400 can be positioned so that at least a portion is positioned within the carotid artery. The contrast agent may be injected through the sheath 400 once positioned in this location. Contrast agent can also be injected through one or more catheters inserted through the guide sheath 400. A baseline angiogram can be obtained, for example in the anterior/posterior (AP) and/or lateral views, prior to device insertion to assess occlusion location by injection of contrast media through the sheath 400 with fluoroscopic visualization. Fluoroscopic visualization may continue as the catheter system is advanced and subsequent angiograms can be captured periodically and particularly after every attempt to retrieve the embolus to assess reperfusion. The baseline angiogram image can be superimposed, such as with digital subtraction angiography, so that the vasculature and/or occlusion site are visible while the catheter system is advanced. Once the catheter system 150 is advanced into position (the positioning will be described in more detail below), the catheter advancement element 300 can be withdrawn and removed from the system. A vacuum source, such as a pump, may be connected to the sheath 400 and activated to direct aspiration to the distal end of the catheter 200. The aspiration may be applied for a period of time (e.g., between about 30 seconds up to about 3 minutes, preferably about 2 minutes) to allow for capture and engulfment of the embolus in the catheter 200. The flow rate of aspiration may vary and in one example can be between about 25 inches Hg (inHg) (12.279 psi) up to about 28 inHg (13.752 psi). In some implementations, the pump is allowed to run to build up a vacuum outside of the patient over a first period prior to applying the vacuum to the vessel, for example, by turning a flow control switch to an "on" position. In other implementations, the pump is turned on at a particular flow rate and is applied to the vessel immediately allowing for the build-up of vacuum through the system. After applying aspiration to the catheter for a period of time, the catheter 200 can be slowly withdrawn. Once free flow is achieved, observable by continuous collection of fluid within a receptacle, the aspiration source can be disconnected from the sheath 400 and a confirmatory angiogram performed. The angiogram can be performed by injecting contrast agent through the aspiration catheter 200 still positioned through the working lumen of the sheath 400. The angiogram can also be performed through the guide sheath 400 after complete removal of the aspiration catheter 200 from the guide sheath 400.

The vacuum source can increase in aspiration level when the flow rate is slow and decrease when the flow rate is increased. In this manner, the force is greatest when the catheter is clogged or partially clogged, but decreases to a minimal level when there is free flow to ensure protection from distal emboli but limit the volume of aspirated blood. In this manner, the system can optimize the embolus aspiration while limiting the amount of blood aspirated. Alternately, the vacuum source can include a vacuum gauge. When the flow in the catheter 200 is blocked or restricted, the pump can create a higher level of vacuum. In this example, the aspiration force may be configured to rise when higher vacuum is detected. Alternatively, the vacuum gauge may be incorporated into the RHV or the Luer or proximal end of the guide sheath 400.

In an implementation, the guide sheath 400 includes one or more radiopaque markers 411. The radiopaque markers 411 can be disposed near the distal end 408. For example, a pair of radiopaque bands may be provided. The radiopaque markers 411 or markers of any of the system components can be swaged, painted, embedded, or otherwise disposed in or on the body. In some implementations, the radiopaque markers include a barium polymer, tungsten polymer blend, tungsten-filled or platinum-filled marker that maintains flexibility of the devices and improves transition along the length of the component and its resistance to kinking. In some implementations, the radiopaque markers are a tungsten-loaded PEBAX or polyurethane that is heat welded to the component.

The guide sheath markers 411 are shown in the figures as rings around a circumference of one or more regions of the body 402. However, the markers 411 can have other shapes or create a variety of patterns that provide orientation to an operator regarding the position of the distal opening 408 within the vessel. Accordingly, an operator may visualize a location of the distal opening 408 under fluoroscopy to confirm that the distal opening 408 is directed toward a target anatomy where a catheter 200 is to be delivered. For example, radiopaque marker(s) 411 allow an operator to rotate the body 402 of the guide sheath 400 at an anatomical access point, e.g., a groin of a patient, such that the distal opening provides access to an ICA by subsequent working device(s), e.g., catheters and wires advanced to the ICA. In some implementations, the radiopaque marker(s) 411 include platinum, gold, tantalum, tungsten or any other substance visible under an x-ray fluoroscope. Any of the various components of the systems described herein can incorporate radiopaque markers.

Still with respect to FIGS. 1A-1B, the catheter 200 can include a relatively flexible, distal luminal portion 222 coupled to a stiffer, kink-resistant proximal extension or proximal control element 230. The term "control element" as used herein can refer to a proximal region configured for a user to cause pushing movement in a distal direction as well as pulling movement in a proximal direction. The control elements described herein may also be referred to as spines, tethers, push wires, push tubes, or other elements having any of a variety of configurations. The proximal control element 230 can be a hollow or tubular element. The proximal control element 230 can also be solid and have no inner lumen, such as a solid rod, ribbon or other solid wire type element. Generally, the proximal control elements described herein are configured to move its respective component (to which it may be attached or integral) in a bidirectional manner through a lumen.

Figure 8B:
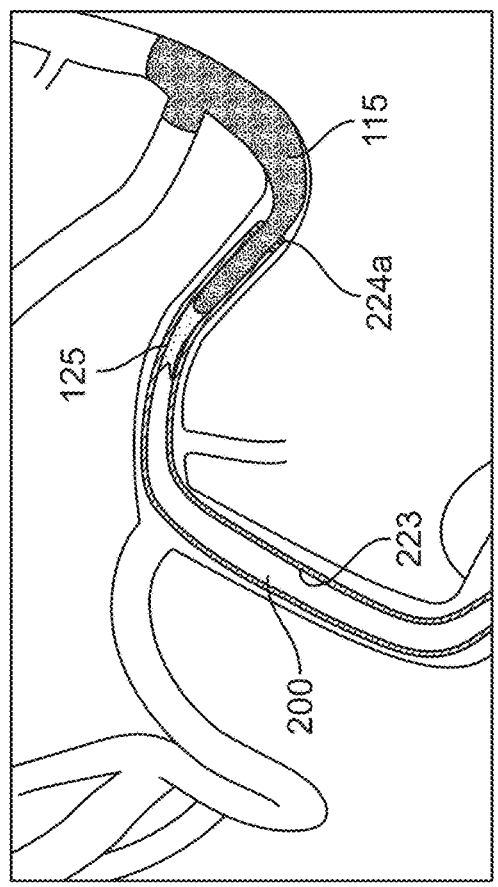
FIG. 8B shows the angiogram of FIG. 8A in schematic.
Figure 8A:
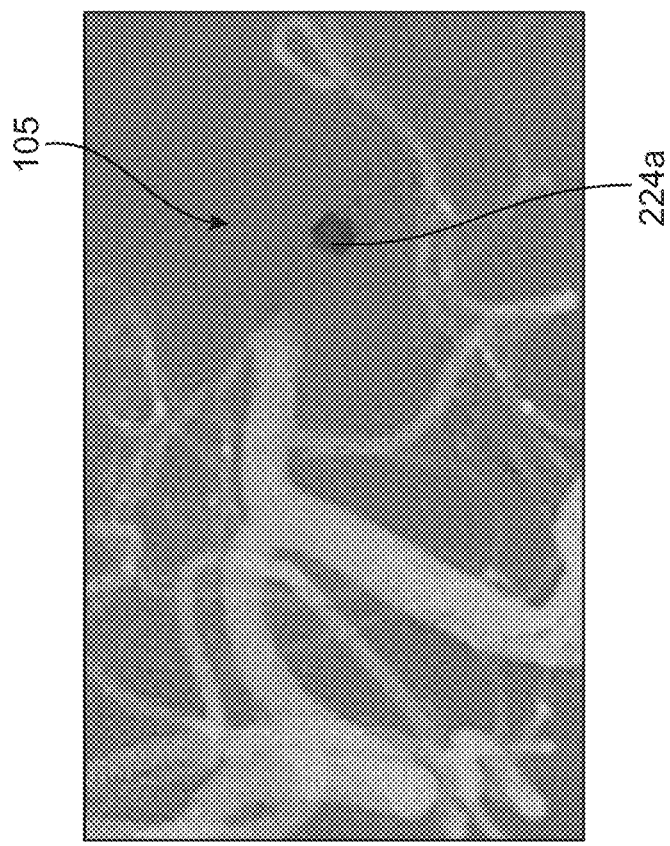
FIG. 8A shows an angiogram of the catheter system of FIG. 5A with the catheter advancement element withdrawn.

A single, inner lumen 223 extends through the luminal portion 222 between a proximal end and a distal end of the luminal portion 222 (the lumen 223 is visible in FIG. 8A). In some implementations, a proximal opening 242 into the lumen 223 can be located near where the proximal control element 230 coupled with the distal luminal portion 222. In other implementations, the proximal opening 242 into the lumen 223 is at a proximal end region of the catheter 200. A distal opening 231 from the lumen 223 can be located near or at the distal-most end 215 of the luminal portion 222. The inner lumen 223 of the catheter 200 can have a first inner diameter and the working lumen of the guide sheath 400 can have a second, larger inner diameter. Upon insertion of the catheter 200 through the working lumen of the sheath 400, the lumen 223 of the catheter 200 can be configured to be fluidly connected and contiguous with the working lumen of the sheath 400 such that fluid flow into and/or out of the system 100 is possible, such as by applying suction from a vacuum source coupled to the system 100 at a proximal end. The combination of sheath 400 and catheter 200 can be continuously in communication with the bloodstream during aspiration at the proximal end with advancement and withdrawal of catheter 200.

The distal luminal portion 222 of the catheter 200 can have a plurality of radiopaque markings 224. A first radiopaque marker 224a can be located near the distal-most end 215 to aid in navigation and proper positioning of the distal-most end 215 under fluoroscopy. Additionally, a proximal region of the catheter 200 may have one or more proximal radiopaque markers 224b so that the overlap region 348 can be visualized as the relationship between a radiopaque marker 411 on the guide sheath 400 and the radiopaque marker 224b on the catheter 200. The proximal region of the catheter 200 may also have one or more radiopaque markings providing visualization, for example, near the proximal opening 242 into the single lumen 223 of the catheter 200 as will be described in more detail below. In an implementation, the two radiopaque markers (marker 224a near the distal-most end 215 and a more proximal marker 224b) are distinct to minimize confusion of the fluoroscopic image, for example the catheter proximal marker 224b may be a single band and the marker 411 on the guide sheath 400 may be a double band and any markers on a working device delivered through the distal access system can have another type of band or mark. The radiopaque markers 224 of the distal luminal portion 222, particularly those near the distal end region navigating extremely tortuous anatomy, can be relatively flexible such that they do not affect the overall flexibility of the distal luminal portion 222 near the distal end region. The radiopaque markers 224 can be tungsten-loaded or platinum-loaded markers that are relatively flexible compared to other types of radiopaque markers used in devices where flexibility is not paramount. In some implementations, the radiopaque marker can be a band of tungsten-loaded PEBAX having a durometer of Shore 35D.

The proximal control element 230 can include one or more markers 232 to indicate the overlap between the distal luminal portion 222 of the catheter 200 and the sheath body 402 as well as the overlap between the distal luminal portion 222 of the catheter 200 and other interventional devices that may extend through the distal luminal portion 222. At least a first mark can be an RHV proximity marker positioned so that when the mark is aligned with the sheath proximal hemostasis valve 434 during insertion of the catheter 200 through the guide sheath 400, the catheter 200 is positioned at the distal-most position with the minimal overlap length needed to create the seal between the catheter 200 and the working lumen. At least a second mark 232 can be a Fluoro-saver marker that can be positioned on the control element 230 and located a distance away from the distal-most end 215 of the distal luminal portion 222. In some implementations, a mark 232 can be positioned about 100 cm away from the distal-most end 215 of the distal luminal portion 222.

Although the catheter advancement element 300 is described herein in reference to catheter 200 it can be used to advance other catheters and it is not intended to be limiting to its use. For example, the catheter advancement element 300 can be used to deliver a 5MAX Reperfusion Catheter (Penumbra, Inc. Alameda, CA), REACT aspiration catheter (Medtronic), or Sophia Plus aspiration catheter (Terumo) for clot removal in patients with acute ischemic stroke or other reperfusion catheters known in the art.

Still with respect to FIGS. 1A-1B and also FIG. 1C, the catheter advancement element 300 can include a non-expandable, flexible elongate body 360 coupled to a proximal portion 366. The catheter advancement element 300 and the catheter 200 described herein may be configured for rapid exchange or over-the-wire methods. For example, the flexible elongate body 360 can be a tubular portion extending the entire length of the catheter advancement element 300 and can have a proximal opening from the lumen 368 of the flexible elongate body 360 that is configured to extend outside the patient's body during use. Alternatively, the tubular portion can have a proximal opening positioned such that the proximal opening remains inside the patient's body during use. The proximal portion 366 can be a proximal element coupled to a distal tubular portion 360 and extending proximally therefrom. A proximal opening from the tubular portion 360 can be positioned near where the proximal element 366 couples to the tubular portion 360. Alternatively, the proximal portion 366 can be a proximal extension of the tubular portion 360 having a length that extends to a proximal opening near a proximal terminus of the catheter advancement element 300 (i.e. outside a patient's body). A luer 364 can be coupled to the proximal portion 366 at the proximal end region so that tools such as a guidewire can be advanced through the lumen 368 of the catheter advancement element 300. A syringe or other component can be coupled to the luer 364 in order to draw a vacuum and/or inject fluids through the lumen 368. The syringe coupled to the luer 364 can also be used to close off the lumen of the catheter advancement element 300 to maximize the piston effect described elsewhere herein.

The configuration of the proximal portion 366 can vary. In some implementations, the proximal portion 366 is simply a proximal extension of the flexible elongate body 360 that does not change significantly in structure but changes significantly in flexibility. For example, the proximal portion 366 transitions from the very flexible distal regions of the catheter advancement element 300 towards less flexible proximal regions of the catheter advancement element 300. The proximal portion 366 provides a relatively stiff proximal end suitable for manipulating and torqueing the more distal regions of the catheter advancement element 300. In other implementations, the proximal portion 366 is a hypotube. The hypotube may be exposed or may be coated by a polymer. In still further implementations, the proximal portion 366 may be a tubular polymer portion reinforced by a coiled ribbon or braid. The proximal portion 366 can have the same outer diameter as the flexible elongate body or can have a smaller outer diameter as the flexible elongate body.

The proximal portion 366 need not include a lumen. For example, the proximal portion 366 can be a solid rod, ribbon, or wire have no lumen extending through it that couples to the tubular elongate body 360. Where the proximal portion 366 is described herein as having a lumen, it should be appreciated that the proximal portion 366 can also be solid and have no lumen. The proximal portion 366 is generally less flexible than the elongate body 360 and can transition to be even more stiff towards the proximal-most end of the proximal portion 366. Thus, the catheter advancement element 300 can have an extremely soft and flexible distal end region 346 that transitions proximally to a stiff proximal portion 366 well suited for pushing and/or torqueing the distal elongate body 360.

The elongate body 360 can be received within and extended through the internal lumen 223 of the distal luminal portion 222 of the catheter 200 (see FIG. 1B). The elongate body 360 or tubular portion can have an outer diameter. The outer diameter of the tubular portion can have at least one snug point. A difference between the inner diameter of the catheter 200 and the outer diameter of the tubular portion at the snug point can be no more than about 0.015" (0.381 mm), or can be no more than about 0.010" (0.254 mm), for example, from about 0.003" (0.0762 mm) up to about 0.012" (0.3048 mm), preferably about 0.005" (0.127 mm) to about 0.010" (0.254 mm), and more preferably about 0.007" (0.1778 mm) to about 0.009" (0.2286 mm).

As will be described in more detail below, the catheter advancement element 300 can also include a distal end region 346 located distal to the at least one snug point of the tubular portion. The distal end region 346 can have a length and taper along at least a portion of the length. The distal end region 346 of the catheter advancement element 300 can be extended beyond the distal end of the catheter 200 as shown in FIG. 1B. The proximal portion 366 of the catheter advancement element 300 or proximal extension is coupled to a proximal end region of the elongate body 360 and extends proximally therefrom. The proximal portion 366 can be less flexible than the elongate body 360 and configured for bidirectional movement of the elongate body 360 of the catheter advancement element 300 within the luminal portion 222 of the catheter 200, as well as for movement of the catheter system 100 as a whole. The elongate body 360 can be inserted in a coaxial fashion through the internal lumen 223 of the luminal portion 222. The outer diameter of at least a region of the elongate body 360 can be sized to substantially fill at least a portion of the internal lumen 223 of the luminal portion 222.

The overall length of the catheter advancement element 300 (e.g. between the proximal end through to the distal-most tip) can vary, but generally is long enough to extend through the support catheter 200 plus at least a distance beyond the distal end of the support catheter 200 while at least a length of the proximal portion 366 remains outside the proximal end of the guide sheath 400 and outside the body of the patient. In some implementations, the overall length of the catheter advancement element 300 is about 145 to about 150 cm and has a working length of about 140 cm to about 145 cm from a proximal tab or hub to the distal-most end 325. The elongate body 360 can have a length that is at least as long as the luminal portion 222 of the catheter 200 although the elongate body 360 can be shorter than the luminal portion 222 so long as at least a minimum length remains inside the luminal portion 222 when a distal portion of the elongate body 360 is extended distal to the distal end of the luminal portion 222 to form a snug point or snug region with the catheter. In some implementations, this minimum length of the elongate body 360 that remains inside the luminal portion 222 when the distal end region 346 is positioned at its optimal advancement configuration is at least about 5 cm, at least about 6 cm, at least about 7 cm, at least about 8 cm, at least about 9 cm, at least about 10 cm, at least about 11 cm, or at least about 12 cm up to about 50 cm. In some implementations, the shaft length of the distal luminal portion 222 can be about 35 cm up to about 75 cm and shorter than a working length of the guide sheath and the insert length of the elongate body 360 can be at least about 45 cm, 46 cm, 47 cm, 48 cm, 48.5 cm, 49 cm, 49.5 cm up to about 85 cm.

The length of the elongate body 360 can allow for the distal end of the elongate body 360 to reach cerebrovascular targets or occlusions within, for example, segments of the internal carotid artery including the cervical (C1), petrous (C2), lacerum (C3), cavernous (C4), clinoid (C5), ophthalmic (C6), and communicating (C7) segments of the internal carotid artery (ICA) as well as branches off these segments including the M1 or M2 segments of the middle cerebral artery (MCA), anterior cerebral artery (ACA), anterior temporal branch (ATB), and/or posterior cerebral artery (PCA). The distal end region of the elongate body 360 can reach these distal target locations while the proximal end region of the elongate body 360 remains proximal to or below the level of severe turns along the path of insertion. For example, the entry location of the catheter system can be in the femoral artery and the target occlusion location can be distal to the right common carotid artery, such as within the M1 segment of the middle cerebral artery on the right side. The proximal end region of the elongate body 360 where it transitions to the proximal portion 366 can remain within a vessel that is proximal to severely tortuous anatomy such as the carotid siphon, the right common carotid artery, the brachiocephalic trunk, the take-off into the brachiocephalic artery from the aortic arch, the aortic arch as it transitions from the descending aorta. This avoids inserting the stiffer proximal portion 366, or the material transition between the stiffer proximal portion 366 and the elongate body 360, from taking the turn of the aortic arch or the turn of the brachiocephalic take-off from the aortic arch, which both can be very severe. The lengths described herein for the distal luminal portion 222 also can apply to the elongate body 360 of the catheter advancement element.

The proximal portion 366 can have a length that varies as well. In some implementations, the proximal portion 366 is about 90 cm up to about 95 cm. The distal portion extending distal to the distal end of the luminal portion 222 can include distal end region 346 that protrudes a length beyond the distal end of the luminal portion 222 during use of the catheter advancement element 300. The distal end region 346 of the elongate body 360 that is configured to protrude distally from the distal end of the luminal portion 222 during advancement of the catheter 200 through the tortuous anatomy of the cerebral vessels, as will be described in more detail below. The proximal portion 366 coupled to and extending proximally from the elongate body 360 can align generally side-by-side with the proximal control element 230 of the catheter 200. The arrangement between the elongate body 360 and the luminal portion 222 can be maintained during advancement of the catheter 200 through the tortuous anatomy to reach the target location for treatment in the distal vessels and aids in preventing the distal end of the catheter 200 from catching on tortuous branching vessels, as will be described in more detail below.

In some implementations, the elongate body 360 can have a region of relatively uniform outer diameter extending along at least a portion of its length and the distal end region 346 tapers down from the uniform outer diameter. The outer diameter of the elongate body 360 can include a step-down at a location along its length, for example, a step-down in outer diameter at a proximal end region where the elongate body 360 couples to the proximal portion 366. Depending upon the inner diameter of the catheter 200, the difference between the inner diameter of catheter 200 and the outer diameter of the elongate body 360 along at least a portion of its length, such as at least 10 cm of its length, preferably at least 15 cm of its length can be no more than about 0.015" (0.381 mm), such as within a range of about 0.003"-0.015" (0.0762 mm-0.381 mm) or between 0.006"-0.010" (0.1524 mm-0.254 mm). Thus, the clearance between the catheter 200 and the elongate body 360 can result in a space on opposite sides that is no more than about 0.008" (0.2032 mm), or can be no more than about 0.005" (0.127 mm), for example, from about 0.001" up to about 0.006" (0.0254 mm-0.1524 mm), preferably about 0.002" to about 0.005" (0.0508 mm-0.127 mm), and more preferably about 0.003" to about 0.005" (0.0762 mm-0.0508 mm).

The catheter advancement element 300 has a large outer diameter and a relatively small inner diameter, particularly when a guidewire extends into or through the lumen of the catheter advancement element 300. The lumen of the catheter advancement element 300 substantially filled by the guidewire and/or liquid creates a closed system with the catheter 200. The catheter advancement element 300 substantially fills or is substantially occlusive to the catheter 200 creating a piston arrangement within the catheter lumen. Withdrawing the occlusive catheter advancement element 300 through the catheter lumen creates an internal vacuum like a plunger in a syringe barrel. The internal vacuum created within the distal end region of the catheter 200 can draw embolic material towards and/or through the distal end 215 of the catheter 200 positioned at or near the face of the embolus 115. As mentioned above, a syringe or flush can be coupled to the luer 364 prior to withdrawal of the catheter advancement element 300 from the catheter lumen. The syringe coupled to the luer 364 of the catheter advancement element 300 closes the system and maximizes the piston effect upon withdrawal. The internal vacuum can begin to clear clot material proximal to the embolus or draw the embolus itself into the distal end of the catheter even before external aspiration is applied at the proximal RHV of the base sheath. Further, the catheter system as it is advanced through the tortuous neuroanatomy can store energy or forces, for example, in the compression of the catheter 200 before the catheter advancement element 300 is withdrawn. The extreme tortuosity of the intracerebral vasculature, particularly around the bony structures of the skull can require more severe force to traverse in combination with the dramatic transition in the size between vessels to reach the occlusion site, such as the large aorta and 1-3 mm sized target vessel, can cause stored forces or energy in a catheter. Withdrawal of the catheter advancement element 300 can release this stored energy causing distally-directed movement of the distal catheter portion 222. A user may exploit the distally-directed movement of the distal catheter portion 222 towards the embolus 115 to atraumatically nest, seat, and/or embed the distal end 215 of the catheter 200 with the proximal face of the embolus 115 for optimum positioning of the catheter 200 relative to the embolus. Withdrawing the catheter advancement element 300 through the catheter lumen can achieve a more successful one-pass embolectomy by creating an initial internal vacuum within the distal end region of the catheter 200 alone or in combination with the distally-directed movements of the distal catheter portion 222.

Various movements of the catheter 200 and/or the catheter advancement element 300 during use of the system, for example withdrawal of the catheter advancement element to achieve the piston effect, can be performed manually or automatically.

The elongate body 360 can have an overall shape profile from proximal end to distal end that transitions from a first outer diameter having a first length to a tapering outer diameter having a second length. The first length of this first outer diameter region (i.e. the snug-fitting region between the distal luminal portion 222 and the elongate body 360) can be at least about 5 cm, or 10 cm, up to about 50 cm. In other implementations, the snug-fitting region can extend from the proximal tab or luer 364 substantially to the tapered distal end region 346 which depending on the length of the catheter advancement element 300, can be up to about 170 cm.

In some implementations, the length of the tapering outer diameter of the distal end region 346 can be between 1 cm and 4 cm. In other implementations, the length of the tapering outer diameter can be over a length of 0.5 cm to 2 cm. In still other implementations, the length of the tapering outer diameter can be over a length of 2 cm to 5 cm. The distal end region 346 of the elongate body 360 can also be shaped with or without a taper. When the catheter advancement element 300 is inserted through the catheter 200, this distal end region 346 is configured to extend beyond and protrude out through the distal-most end 215 of the luminal portion 222 whereas the more proximal region of the body 360 (i.e. the first length described above) remains within the luminal portion 222.

As mentioned, the distal-most end 215 of the luminal portion 222 can be blunt and have no change in the dimension of the outer diameter whereas the distal end region 346 can be tapered providing an overall elongated tapered geometry of the catheter system. The outer diameter of the elongate body 360 also approaches the inner diameter of the luminal portion 222 such that the step-up from the elongate body 360 to the outer diameter of the luminal portion 222 is minimized Minimizing this step-up prevents issues with the lip formed by the distal end of the luminal portion 222 catching on the tortuous neurovasculature, such as around the carotid siphon near the ophthalmic artery branch, when the distal end region 346 in combination with the distal end region of the catheter 200 bends and curves along within the vascular anatomy. In some implementations, the inner diameter of the luminal portion 222 can be at least about 0.052" (1.321 mm), about 0.054" (1.372 mm) and the maximum outer diameter of the elongate body 360 can be about 0.048" (1.219 mm) such that the difference between them is about 0.006" (0.1524 mm). In some implementations, the inner diameter of the luminal portion 222 can be about 0.070" (1.778 mm) and the maximum outer diameter of the elongate body 360 can be about 0.062" (1.575 mm) such that the difference between them is about 0.008" (0.2032 mm). In some implementations, the inner diameter of the luminal portion 222 can be about 0.088" (2.235 mm) and the maximum outer diameter of the elongate body 360 can be about 0.080" (2.032 mm) such that the difference between them is about 0.008" (0.2032 mm). In some implementations, the inner diameter of the luminal portion 222 can be about 0.072" (1.829 mm) and the maximum outer diameter of the elongate body 360 is about 0.070" (1.778 mm) such that the difference between them is only 2 thousandths of an inch (0.002"/0.0508 mm). In other implementations, the maximum outer diameter of the elongate body 360 is about 0.062" (1.575 mm) such that the difference between them is about 0.010" (0.254 mm). Despite the outer diameter of the elongate body 360 extending through the lumen of the luminal portion 222, the luminal portion 222 and the elongate body 360 extending through it in co-axial fashion are flexible enough to navigate the tortuous anatomy leading to the level of M1 or M2 arteries without kinking and without damaging the vessel.

The dimensions provided herein are approximate and each dimensions may have an engineering tolerance or a permissible limit of variation. Use of the term "about," "approximately," or "substantially" are intended to provide such permissible tolerance to the dimension being referred to. Where "about" or "approximately" or "substantially" is not used with a particular dimension herein that that dimension need not be exact.

The length of the tapered distal end region 346 can vary. In some implementations, the length of the distal end region 346 can be in a range of between about 0.50 cm to about 4.0 cm from the distal-most end of the elongate body 360 or between about 1.0 cm to about 3.0 cm. In other implementations, the length of the distal end region 346 is between 2.0 cm to about 2.5 cm. In some implementations, the length of the distal end region 346 varies depending on the inner diameter of the catheter 200 with which the catheter advancement element 300 is to be used. For example, the length of the distal end region 346 can be as shorter (e.g. 1.2 cm) for a catheter advancement element 300 sized to be used with a catheter 200 having an inner diameter of about 0.054" (1.372 mm) and can be longer (e.g. 2.5 cm) for a catheter advancement element 300 sized to be used with a catheter 200 having an inner diameter of about 0.088" (2.235 mm). The distal end region 346 can be a constant taper from the larger outer diameter of the elongate body 360 (e.g. the distal end of the marker 344b) down to a second smaller outer diameter at the distal-most terminus (e.g. the proximal end of the marker 344a) as shown in FIG. 1C. In some implementations, the constant taper of the distal end region 346 can be from about 0.048" outer diameter down to about 0.031" (0.787 mm) outer diameter over a length of about 1 cm. In some implementations, the constant taper of the distal end region 346 can be from 0.062" (1.575 mm) outer diameter to about 0.031" (0.787 mm) outer diameter over a length of about 2 cm. In still further implementations, the constant taper of the distal end region 346 can be from 0.080" (2.032 mm) outer diameter to about 0.031" (0.787 mm) outer diameter over a length of about 2.5 cm. The length of the constant taper of the distal end region 346 can vary, for example, between 0.8 cm to about 2.5 cm, or between 1 cm and 3 cm, or between 2.0 cm and 2.5 cm. The angle of the taper can vary depending on the outer diameter of the elongate body 360. For example, the angle of the taper can be between 0.9 to 1.6 degrees relative to horizontal. The angle of the taper can be between 2-3 degrees from a center line of the elongate body 360. The length of the taper of the distal end region 346 can be between about 5 mm to 20 mm or about 20 mm to about 50 mm.

The elongate body 360 of the catheter advancement element 300 can have a lumen 368 when an inner diameter that does not change over the length of the elongate body even in the presence of the tapering of the distal end region 346. Thus, the inner diameter of the lumen 368 extending through the tubular portion of the catheter advancement element 300 can remain uniform and the wall thickness of the distal end region 346 can decrease to provide the taper. The wall thickness can thin distally along the length of the taper. Thus, the material properties in combination with wall thickness, angle, length of the taper can all contribute to the overall maximum flexibility of the distal-most end of the distal end region 346. The catheter advancement element 300 undergoes a transition in flexibility from the distal-most end towards the snug point where it achieves an outer diameter that is no more than about 0.010" (0.254 mm) different from the inner diameter of the catheter 200.

The length of the taper can also vary depending on the anatomy of the target region. The distal end region 346 can achieve its soft, atraumatic and flexible characteristic due to a material property other than due to a change in outer dimension to facilitate endovascular navigation to an embolus in tortuous anatomy. Additionally or alternatively, the distal end region 346 of the elongate body 360 can have a transition in flexibility along its length. The most flexible region of the distal end region 346 can be its distal terminus. Moving along the length of the distal end region 346 from the distal terminus towards a region proximal to the distal terminus. For example, the distal end region 346 can be formed of a material having a Shore material hardness of no more than 35D or about 62A and transitions proximally to be less flexible near where it is formed of a material having a material hardness of no more than 55D and 72D up to the proximal portion 366, which can be a stainless steel hypotube, or a combination of a material property and tapered shape. The materials used to form the regions of the elongate body 360 can include PEBAX (such as PEBAX 25D, 35D, 55D, 69D, 72D) or a blend of PEBAX (such as a mix of 25D and 35D, 25D and 55D, 25D and 72D, 35D and 55D, 35D and 72D, 55D and 72D, where the blend ratios may range from 0.1% up to 50% for each PEBAX durometer), with a lubricious additive compound, such as Mobilize (Compounding Solutions, Lewiston, Maine). In some implementations, the material used to form a region of the elongate body 360 can be Tecothane 62A. Incorporation of a lubricious additive directly into the polymer elongate body means incorporation of a separate lubricious liner, such as a Teflon liner, is unnecessary. This allows for a more flexible element that can navigate the distal cerebral anatomy and is less likely to kink Similar materials can be used for forming the distal luminal portion 222 of the catheter 200 providing similar advantages. The flexibility of the distal end region 346 can be achieved by a combination of flexible lubricious materials and tapered shapes. For example, the length of the distal end region 346 can be kept shorter than 2 cm-3 cm, but maintain optimum deliverability due to a change in flexible material from distal-most end 325 towards a more proximal region a distance away from the distal-most end 325. In an implementation, the elongate body 360 is formed of PEBAX (polyether block amide) embedded silicone designed to maintain the highest degree of flexibility. The wall thickness of the distal end of the luminal portion 222 can also be made thin enough such that the lip formed by the distal end of the luminal portion 222 relative to the elongate body 360 is minimized.

The elongate body 360 has a benefit over a microcatheter in that it can have a relatively large outer diameter that is just 0.003"-0.010" (0.0762 mm-0.254 mm) smaller than the inner diameter of the distal luminal portion 222 of the catheter 200 and still maintaining a high degree of flexibility for navigating tortuous anatomy. When the gap between the two components is too tight (e.g. less than about 0.003"

(0.0762 mm), the force needed to slide the catheter advancement element 300 relative to the catheter 200 can result in damage to one or both of the components and increases risk to the patient during the procedure. The gap results in too tight of a fit to provide optimum relative sliding. When the gap between the two components is too loose (e.g. greater than about 0.010"/0.254 mm), the distal end of the catheter 200 forms a lip that is prone to catch on branching vessels during advancement through tortuous neurovasculature, such as around the carotid siphon where the ophthalmic artery branches off and the piston effect of withdrawal of the elongate body 360 can be decreased or lost.

The gap in ID/OD between the elongate body 360 and the distal luminal portion 222 can be in this size range (e.g. 0.003"-0.015" (0.0762 mm-0.381 mm) or between 0.006"-0.010" (0.152 mm-0.254 mm)) along a majority of their lengths. For example, the elongate body 360 can have a relatively uniform outer diameter that is between about 0.048" (1.219 mm) to about 0.080" (2.032 mm) from a proximal end region to a distal end region up to a point where the taper of the distal end region 346 begins. Similarly, the distal luminal portion 222 of the catheter 200 can have a relatively uniform inner diameter that is between about 0.054" (1.372 mm) to about 0.088" (2.235 mm) from a proximal end region to a distal end region. As such, the difference between their respective inner and outer diameters along a majority of their lengths can be within this gap size range of 0.003" to 0.015" (0.0762 mm-0.381 mm). The distal end region 346 of the elongate body 360 that is tapered will have a larger gap size relative to the inner diameter of the distal luminal portion 222. During use, however, this tapered distal end region 346 is configured to extend distal to the distal end of the catheter 200 such that the region of the elongate body 360 having an outer diameter sized to match the inner diameter of the distal luminal portion 222 is positioned within the lumen of the catheter 200 such that it can minimize the lip at the distal end of the catheter 200.

The elongate body 360 can be formed of various materials that provide a suitable flexibility and lubricity. Example materials include high density polyethylene, 77A PEBAX, 33D PEBAX, 42D PEBAX, 46D PEBAX, 54D PEBAX, 69D PEBAX, 72D PEBAX, 90D PEBAX, and mixtures thereof or equivalent stiffness and lubricity material. In some implementations, the elongate body 360 is an unreinforced, non-torqueing catheter having a relatively large outer diameter designed to fill the lumen it is inserted through and a relatively small inner diameter to minimize any gaps at a distal-facing end of the device. In other implementations, at least a portion of the elongate body 360 can be reinforced to improve navigation and torqueing (e.g. braided reinforcement layer). The flexibility of the elongate body 360 can increase towards the distal end region 346 such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking. If the elongate body 360 has a braid reinforcement layer along at least a portion of its length, the braid reinforcement layer can terminate a distance proximal to the distal end region 346. For example, the distance from the end of the braid to the distal-most end 325 can be about 10 cm to about 15 cm or from about 4 cm to about 10 cm or from about 4 cm up to about 15 cm.

In some implementations, the elongate body 360 can be generally tubular along at least a portion of its length such that it has a single lumen 368 extending parallel to a longitudinal axis of the catheter advancement element 300 (see FIG. 1A-1D). In an implementation, the single lumen 368 of the elongate body 360 is sized to accommodate a guidewire, however use of the catheter advancement element 300 generally eliminates the need for a guidewire lead. Preferably, the assembled system includes no guidewire. Guidewires are designed to be exceptionally flexible so that they deflect to navigate the severe turns of the anatomy. However, many workhorse guidewires have a stiffness along their longitudinal axis and/or are small enough in outer diameter that they find their own paths through an embolus rather than slipping around the embolus. In some cases, these guidewires can cause perforations and/or dissections of the vessel itself. Thus, even though the guidewire may have an outer diameter at its distal tip region that is small and very flexible at the distal tip, guidewires typically are incapable of atraumatically probing an embolus. Guidewires do not deflect upon encountering the dense proximal face of the embolus. Instead, guidewires embed and penetrate an embolus. The catheter advancement element 300 has a softness, taper, and sizing that finds and/or creates space to slide between a portion of the embolus and the vessel wall rather than penetrating through it like a guidewire does. Methods of using the catheter advancement element 300 without a guidewire or with a rescue guidewire 500 parked within the lumen 368 (see FIG. 1D) to deliver a catheter to distal regions of the brain, such as at a true proximal face of an embolus, are described in more detail below.

A guidewire can extend through the single lumen 368 generally concentrically from a proximal opening to a distal opening 326 at the distal end 325 of the catheter advancement element 300 through which the guidewire can extend. In some implementations, the proximal opening is at the proximal end of the catheter advancement element 300 such that the catheter advancement element 300 is configured for over-the-wire (OTW) methodologies. In other implementations, the proximal opening is a rapid exchange opening through a wall of the catheter advancement element 300 such that the catheter advancement element 300 is configured for rapid exchange rather than or in addition to OTW. In this implementation, the proximal opening extends through the sidewall of the elongate body 360 and is located a distance away from a proximal tab 364 and distal to the proximal portion 366. The proximal opening can be located a distance of about 10 cm from the distal end region 346 up to about 20 cm from the distal end region 346. In some implementations, the proximal opening can be located near a region where the elongate body 360 is joined to the proximal portion 366, for example, just distal to an end of the hypotube. In other implementations, the proximal opening is located more distally such as about 10 cm to about 18 cm from the distal-most end of the elongate body 360. A proximal opening that is located closer to the distal end region 346 allows for easier removal of the catheter advancement element 300 from the catheter 200 leaving the guidewire in place for a "rapid exchange" type of procedure. Rapid exchanges can rely on only a single person to perform the exchange. The catheter advancement element 300 can be readily substituted for another device using the same guidewire that remains in position. The single lumen 368 of the elongate body 360 can be configured to receive a guidewire in the range of 0.014" (0.356 mm) and 0.018" (0.457 mm) diameter, or in the range of between 0.014" and 0.022" (0.356 mm-0.559 mm). In this implementation, the inner luminal diameter of the elongate body 360 can be between 0.020" and 0.024" (0.508 mm-0.610 mm). The guidewire, the catheter advancement element 300, and the catheter 200 can all be assembled co-axially for insertion through the working lumen of the guide sheath 400. The inner diameter of the lumen 368 of the elongate body 360 can be 0.019" to about 0.021" (0.483 mm-0.533 mm). The distal opening from the lumen 368 can have an inner diameter that is between about 0.018" to about 0.024" (0.457 mm-0.610 mm).

The region near the distal end region 346 can be tapered such that the outer diameter tapers over a length of about 1 cm to about 4 cm. In some implementations, the distal taper length is about 2.5 cm. In other implementations, the distal taper is over a length of about 2 cm to about 5 cm, or about 0.5 cm to 2 cm, or about 1 cm to about 3 cm. The larger outer diameter can be at least about 1.5 times, 2 times, 2.5 times, or about 3 times larger than the smaller outer diameter. The distal end region 346 can taper along a distance from a first outer diameter to a second outer diameter, the first outer diameter being at least 1.5 times the second outer diameter. In some implementations, the distal end region 346 tapers from about 0.080" (2.032 mm) to about 0.031" (0.787 mm). In some implementations, the smaller outer diameter at a distal end of the taper can be about 0.026" (0.66 mm) up to about 0.040" (1.016 mm) and the larger outer diameter proximal to the taper is about 0.062" (1.575 mm) up to about 0.080" (2.032 mm). Also, the distal end region 346 can be formed of a material having a material hardness (e.g. 62A and 35D) that transitions proximally towards increasingly harder materials having (e.g. 55D and 72D) up to the proximal portion 366. A first segment of the elongate body 360 including the distal end region 346 can be formed of a material having a material hardness of 35D and a length of about 10 cm to about 12.5 cm. The first segment of the elongate body 360 including the distal end region 346 can be formed of a material having a material hardness of 62A and a length of about 10 cm to about 12.5 cm. A second segment of the elongate body 360 can be formed of a material having a material hardness of 55D and have a length of about 5 cm to about 8 cm. A third segment of the elongate body 360 can be formed of a material having a material hardness of 72D can be about 25 cm to about 35 cm in length. The three segments combined can form an insert length of the elongate body 360 from where the proximal portion 366 couples to the elongate body 360 to the terminus of the distal end region 346 that can be about 49 cm in length.

In preferred embodiments it has been found that having a flexible distal tapered embolus-probing tip section having a length in the range of 1 cm to 5 cm and that tapers from a proximal outer diameter in the range of 1.58 mm-2.03 mm to a distal outer diameter in the range of 0.66 mm-0.79 mm, the atraumatic tip preferably being radiopaque, that the tapered tip region has a flexibility allowing it to deflect generally away from a dense embolus towards the vessel wall. The deflection occurs upon advancement of the catheter advancement element through the vessel on encountering a resistance to further axial motion from a generally organized or dense embolus within a flexible vessel having an inner diameter about 2-5 mm for an embolus located in the MCA or larger inner diameter up to about 8 mm for an embolus located proximal to the MCA such as within the ICA. The tip region is arranged to deflect away from the proximal face of the embolus towards the vessel wall and, in some instances, to move at least partially under the proximal face of the embolus so that between about 0 mm to about 3 cm of the embolus-probing tip section extends between the obstacle and the vessel wall upon application of an additional force to urge the embolus-probing tip section against the embolus.

Conventional catheters and guidewires have a tip structure that tend to embed into the embolus as opposed to probe the front face of the embolus to find a space or deflect away from the proximal face. Guidewires have small outer diameters and flexible distal tips. Despite the small outer diameter and the flexibility, a guidewire tip is incapable of probing the embolus according to the methods provided herein. Rather, a guidewire tip construction, particularly when used with a microcatheter that provides a centering effect on the guidewire, results in the guidewire penetrating and embedding into or passing through the embolus. FIG. 16A illustrates a conventional guidewire GW extending through and centered by a microcatheter M. The guidewire GW has a tip region embedded within and penetrating an embolus 115. FIG. 16B (and also FIG. 15B) illustrates the tapered distal tip region 346 of a catheter advancement element probing the embolus 115 so that the tip deflects and slips between the proximal face of the embolus 115 and the vessel wall.

The distal end region of the guidewire has a profile that is much smaller compared to the profile of the distal tip region 346 of the catheter advancement element. The outer diameter of the guidewire also stays small moving proximally along its length compared to the catheter advancement element that enlarges to an even larger outer diameter moving proximally just a few centimeters. In turn, the force per unit area for the guidewire is much higher compared to the catheter advancement element. A guidewire used in the neurovasculature, particularly at the level of the MCA, may have an outer diameter at the distal end that is 0.014" (0.36 mm) and have a distal-facing contact area that is about $1.50 \times 10^{-4}$ square inch (0.100 mm$^2$). The outer diameter of the distal end of the catheter advancement element can be about 0.031" (0.79 mm) and the inner diameter of the distal end of the catheter advancement element can be about 0.021" (0.53 mm). The distal-facing contact area for the catheter advancement element can be about $8.00 \times 10^4$ square inch (0.5 mm$^2$) if the lumen is filled with a column of fluid and/or a guidewire. The distal-facing contact area for the catheter advancement element can be about $4.20 \times 10^{-4}$ square inch (0.27 mm$^2$) for just the annular distal-facing surface without a column of fluid or guidewire within the lumen. Regardless, the force per unit area of the guidewire is significantly greater (i.e., about 2 to 5 times greater) than the force per unit area of the catheter advancement element. The force per unit area of a 0.014" guidewire for 1 N force is about 6,700 N/square inch (10 N/mm$^2$) whereas the force per unit area of the catheter advancement element is about 1,300 N/square inch (2 N/mm$^2$) to about 2,400 N/square inch (4 N/mm$^2$). The profile of the guidewire, in combination with the force per unit area for the guidewire (and centering effect provided by the microcatheter), creates a higher risk of penetration of the embolus rather than deflection upon encountering the proximal face of the embolus. The profile of the catheter advancement element including the greater outer diameter as the distal end, the relatively short taper to an even larger outer diameter, and its high flexibility results in the catheter advancement element being incapable of penetrating the embolus and instead deflecting away from the proximal face of the embolus upon encountering one within a vessel. Guidewires penetrate an embolus or vessel wall. The catheter advancement element, in contrast, probes and deflects away from the embolus, finds any space and wedges into a final resting spot without penetrating the embolus or the vessel wall.

It is desirable to have a specially constructed tip region to ensure the tip region will deflect relative to an embolus, not penetrate the embolus, when encountering it within the vessel. The tip region will deflect until it finds a path or space. This is achieved by having a sufficient degree of flexibility of the fully polymeric distal tip region that includes a taper over a length so that the tip region deflects readily upon coming into contact with the proximal face of an embolus. The flexibility and shape of the tapered tip region results in the tip region, which is protruding from the aspiration catheter during advancement through the vessel, passing through less organized or less dense thrombotic material until the tip region encounters the true proximal face of the embolus. The tip region then deflects away from the organized or dense portion of the embolus so that, for example, it wedges between the embolus and the vessel wall. The tip region is constructed to find the path of least resistance in an atraumatic manner without being so flexible or prone to bending that it folds over onto itself and cannot be advanced.

The distal-most tip of the tip region can have a smooth, relatively rounded shape having a low friction outer surface that tends to encourage deflection of the tip region relative to the proximal face of the embolus. The distal tip can also be radiopaque due to embedding a material within the polymer as described in more detail below.

One of skill in the art can "tune" the distal tip region to have one or more properties to achieve the novel requirements set out herein. However, because the requirements are so unusual, it may be useful to measure the properties of the distal tip region using a test rig 1705. For example, FIG. 17A illustrates an implementation of a test rig 1705 and FIG. 17B is a schematic of the test rig 1705 in FIG. 17A. The test rig 1705 can include a 3D printed model of clear silicone material based on a CT/MRI scan data of an actual human patient that is configured to be connected to a pump 1710 for delivering a liquid from a source 1715 to simulate the endovascular environment. The vessels modeled by the test rig 1705 can vary, including, but not limited to femoral artery, abdominal aortic artery, renal artery, aortic artery, subclavian artery, carotid artery, and intracranial arteries. The intracranial arteries of the test rig 1705 can include various sized vessels including the internal carotid artery ICA, the carotid siphon CS, the terminal bifurcation TB of the ICA, and the middle cerebral artery MCA. A dummy embolus DE formed of a suitable material can be positioned within the vessel model, for example, within the MCA as shown in FIG. 17B, to simulate an actual embolus. The material can include a moldable, compressible polymeric material that can be compressed into a small plug shape suitable for insertion into a vessel of interest on the test rig 1705. FIGS. 17A-17B illustrate the dummy embolus DE positioned within the MCA of the test rig 1705 distal to the terminal bifurcation TB of the ICA. The larger vessels of the test rig 1705 can have an internal diameter of about 10 mm that decreases down to about 5 mm ID and towards the most narrow vessels about 2 mm inner diameter. The model vessel containing the dummy embolus DE can have an inner diameter of about 2 mm up to about 3 mm and can taper along its length although smaller or larger vessels can also be used. The dummy embolus DE can be compressed into a plug that has a maximum outer diameter that substantially matches the inner diameter of the vessel being obstructed by the dummy embolus DE. The material of the dummy embolus DE can have an outer diameter prior to being compressed that is about 6 mm to about 8 mm and a length of about 5 mm. The length of the dummy embolus DE can increase upon being compressed into the smaller diameter plug or can be trimmed after compressing to have a particular length. The dummy embolus DE once compressed can be positioned within the target vessel. The dummy embolus DE once positioned in the target vessel can fully or partially block fluid flow through the model and past the dummy embolus DE. The dummy embolus DE can have a density at its proximal face that is comparable to a typical embolus treated in this part of the cerebral vasculature and used to observe the degree of deflection a distal tip region 346 of a catheter advancement element positioned distal to the aspiration catheter 200 being advanced. The material of the dummy embolus DE can be selected so as to have different consistencies to emulate the different types of emboli that might be encountered. The test rig 1705 provides a way to assess whether the distal tip region 346 of the catheter advancement element will deflect or embed within the dummy embolus DE. The test rig 1705 can also assess the impact of a guidewire positioned within the lumen of the catheter advancement element, for example so the distal end of the guidewire is positioned proximal to the distal opening from the lumen, on the deflection of the distal tip region 346 upon encountering the different dummy emboli DE. Those of skill in the art may have alternative test rigs incorporating alternative real or synthetic embolus test subjects including other materials shaped to form an obstruction in the vessel.

The catheter advancement element 300 can incorporate a reinforcement layer. The reinforcement layer can be a braid or other type of reinforcement to improve the torquability of the catheter advancement element 300 and help to bridge the components of the catheter advancement element 300 having such differences in flexibility. The reinforcement layer can bridge the transition from the rigid, proximal portion 366 to the flexible elongate body 360. In some implementations, the reinforcement layer can be a braid positioned between inner and outer layers of PEBAX. The reinforcement layer can terminate a distance proximal to the distal end region 346. The distal end region 346 can be formed of a material having a material hardness of at most about 35D. The first segment can be unreinforced polymer having a length of about 4 cm up to about 12.5 cm without metal reinforcement. The third segment of the elongate body 360 located proximal to the first segment can include the reinforcement layer and can extend a total of about 37 cm up to the unreinforced distal segment. A proximal end region of the reinforcement layer can overlap with a distal end region of the proximal portion 366 such that a small overlap of hypotube and reinforcement exists near the transition between the proximal portion 366 and the elongate body 360.

An entry port for a procedural guidewire can be positioned a distance away from the distal-most end of the elongate body 360. In some implementations, the entry/exit port can be about 18 cm from the distal-most end creating a rapid exchange wire entry/exit segment. The outer diameter of the elongate body 360 within the first two segments can be about 0.080"-0.082" (2.032 mm-2.083 mm) whereas the third segment proximal to this rapid exchange wire entry/exit segment can have a step-down in outer diameter such as about 0.062"-0.064" (1.575 mm-1.626 mm).

The tubular portion of the catheter advancement element 300 can have an outer diameter that has at least one snug point. A difference between the outer diameter at the snug point and the inner diameter of the lumen at the distal end of the distal, catheter portion can be no more than about 0.015" (0.381 mm), or can be no more than about 0.010" (0.254 mm). The at least one snug point of this tubular portion can be a point along the length of the tubular portion. The at least one snug point of this tubular portion can have a length that is at least about 5 cm up to about 50 cm, including for example, at least about 6 cm, at least about 7 cm, at least about 8 cm, at least about 9 cm, at least about 10 cm, at least about 11 cm, or at least about 12 cm up to about 50 cm. This length need not be uniform such that the length need not be snug along its entire length. For example, the snug point region can include ridges, grooves, slits, or other surface features.

In other implementations, the entire catheter advancement element 300 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 1C). In some implementations, the proximal portion 366 can be a skived hypotube of stainless steel coated with PTFE having an outer diameter of 0.026" (0.660 mm). In other implementations, the outer diameter can be between 0.024" (0.610 mm) and 0.030" (0.762 mm). In some implementations, such as an over-the-wire version, the proximal portion 366 can be a skived hypotube coupled to a proximal hub or luer 364. The proximal portion 366 can extend eccentric or concentric to the distal luminal portion 222. The proximal portion 366 can be a stainless steel hypotube. The proximal portion 366 can be a solid metal wire that is round or oval cross-sectional shape. The proximal portion 366 can be a flattened ribbon of wire having a rectangular cross-sectional shape. The ribbon of wire can be curved into a circular, oval, c-shape, or quarter circle, or other cross-sectional shape along an arc. The proximal portion 366 can have any of variety of cross-sectional shapes whether or not a lumen extends therethrough, including a circular, oval, C-shaped, D-shape, or other shape. In some implementations, the proximal portion 366 is a hypotube having a D-shape such that an inner-facing side is flat and an outer-facing side is rounded. The rounded side of the proximal portion 366 can be shaped to engage with a correspondingly rounded inner surface of the sheath 400. The hypotube can have a lubricious coating such as PTFE. The hypotube can have an inner diameter of about 0.021" (0.533 mm), an outer diameter of about 0.0275" (0.699 mm), and an overall length of about 94 cm providing a working length for the catheter advancement element 300 that is about 143 cm. Including the proximal luer 364, the catheter advancement element 300 can have an overall length of about 149 cm. In some implementations, the hypotube can be a tapered part with a length of about 100 mm, starting proximal with a thickness of 0.3 mm and ending with a thickness of 0.10 mm to 0.15 mm. In still further implementations, the elongate body 360 can be a solid element coupled to the proximal portion 366 having no guidewire lumen.

The proximal portion 366 is shown in FIG. 1A as having a smaller outer diameter compared to the outer diameter of the elongate body 360. The proximal portion 366 need not step down in outer diameter and can also have the same outer diameter as the outer diameter as the elongate body 360. For example, the proximal portion 366 can incorporate a hypotube or other stiffening element that is coated by one or more layers of polymer resulting in a proximal portion 366 having substantially the same outer diameter as the elongate body 360.

At least a portion of the solid elongate body 360, such as the elongate distal end region 346, can be formed of or embedded with or attached to a malleable material that skives down to a smaller dimension at a distal end. The distal end region 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. In some implementations, the catheter advancement element 300 can have a working length of about 140 cm to about 143 cm and the elongate body 360 can have an insert length of about 49 cm. The insert length can be the PEBAX portion of the elongate body 360 that is about 49.5 cm. As such, the malleable length of the elongate body 360 can be between about 0.5 cm to about 25 cm or more. The shape change can be a function of a user manually shaping the malleable length prior to insertion or the distal end region 346 can be pre-shaped at the time of manufacturing into a particular angle or curve. Alternatively, the shape change can be a reversible and actuatable shape change such that the distal end region 346 forms the shape upon activation by a user such that the distal end region 346 can be used in a straight format until a shape change is desired by the user. The catheter advancement element 300 can also include a forming mandrel extending through the lumen of the elongate body 360 such that a physician at the time of use can mold the distal end region 346 into a desired shape. As such, the moldable distal end region 346 can be incorporated onto an elongate body 360 that has a guidewire lumen.

The elongate body 360 can extend along the entire length of the catheter 200, including the distal luminal portion 222 and the proximal extension 230 or the elongate body 360 can incorporate the proximal portion 366 that aligns generally side-by-side with the proximal extension 230 of the catheter 200. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Again with respect to FIGS. 1A-1D, like the distal luminal portion 222 of the catheter 200, the elongate body 360 can have one or more radiopaque markers 344 along its length. The one or more markers 344 can vary in size, shape, and location. One or more markers 344 can be incorporated along one or more parts of the catheter advancement element 300, such as a tip-to-tip marker, a tip-to-taper marker, an RHV proximity marker, a Fluoro-saver marker, or other markers providing various information regarding the relative position of the catheter advancement element 300 and its components. In some implementations and as best shown in FIGS. 1C-1D, a distal end region can have a first radiopaque marker 344a and a second radiopaque marker 344b can be located to indicate the border between the tapering of the distal end region 346 and the more proximal region of the elongate body 360 having a uniform or maximum outer diameter. This provides a user with information regarding an optimal extension of the distal end region 346 relative to the distal end of the luminal portion 222 to minimize the lip at this distal end of the luminal portion 222 for advancement through tortuous anatomy. In other implementations, for example where the distal end region 346 is not necessarily tapered, but instead has a change in overall flexibility along its length, the second radiopaque marker 344b can be located to indicate the region where the relative flexibilities of the elongate body 360 (or the distal end region 346 of the elongate body 360) and the distal end of the luminal portion 222 are substantially the same. The marker material may be a platinum/iridium band, a tungsten, platinum, or tantalum-impregnated polymer, or other radiopaque marker that does not impact the flexibility of the distal end region 346 and elongate body 360. In some implementations, the radiopaque markers are extruded PEBAX loaded with tungsten for radiopacity. In some implementations, the proximal marker band can be about 2.0 mm wide and the distal marker band can be about 2.5 mm wide to provide discernable information about the distal end region 346.

The catheter 200 and catheter advancement element 300 (with or without a guidewire) can be advanced as a single unit through the both turns of the carotid siphon. Both turns can be traversed in a single smooth pass or throw to a target in a cerebral vessel without the step-wise adjustment of their relative extensions and without relying on the conventional step-wise advancement technique with conventional microcatheters. The catheter 200 having the catheter advancement element 300 extending through it allows a user to advance them in unison in the same relative position from the first bend of the siphon through the second bend beyond the terminal cavernous carotid artery into the ACA and MCA. Importantly, the advancement of the two components can be performed in a single smooth movement through both bends without any change of hand position.

The catheter advancement element 300 can be in a juxtapositioned relative to the catheter 200 that provides an optimum relative extension between the two components for single smooth advancement. The catheter advancement element 300 can be positioned through the lumen of the catheter 200 such that its distal end region 346 extends just beyond a distal-most end 215 of the catheter 200. The distal end region 346 of the catheter advancement element 300 eliminates the stepped transition between the inner member and the outer catheter 200 thereby avoiding issues with catching on branching vessels within the region of the vasculature such that the catheter 200 may easily traverse the multiple angulated turns of the carotid siphon. The optimum relative extension, for example, can be the distal end region 346 of the elongate body 360 extending just distal to a distal-most end 215 of the catheter 200. A length of the distal end region 346 extending distal to the distal-most end 215 of the catheter 200 during advancement can be between 0.5 cm and about 4 cm. This juxtaposition can be a locked engagement with a mechanical element or simply by a user holding the two components together. The mechanical locking element can be a fixed or removable mechanical element configured to connect to one or more of the catheter 200, the catheter advancement element 300, and the guidewire 500. The mechanical locking element can be slidable along at least a length of the system components when coupled so that the mechanical attachment is adjustable. The mechanical locking element can be a disposable feature or reusable for connecting to at least a portion of the shaft or a more proximal portion of the component such as the luer or hub at a proximal end of the component. In some implementations, the mechanical locking element can be clamped onto the catheter and the catheter advancement element in a desired relative position so that the two can be advanced together without the relative position being inadvertently changed. The relative position can be changed, if desired, while the mechanical locking element is clamped onto the catheter and the catheter advancement element. The mechanical locking element can be additionally clamped onto a region of the guidewire extending through the catheter advancement element such that the relative position of all three components can be maintained during advancement until a relative sliding motion is desired. In still further implementations, the clamping position of the mechanical locking element can be changed from engaging with a first combination of components (e.g., the catheter, catheter advancement element, and the guidewire) to a different combination of components (e.g., the catheter advancement element and the guidewire) depending on what phase of the method is being performed. In still further implementations, the guidewire is held fixed relative to the catheter advancement element via a rotating hemostatic valve coupled to the proximal hub and the catheter advancement element is held fixed to the catheter by a separate mechanical locking element. Whether the relative position of the components is fixed by a mechanical element, a combination of mechanical elements, or by a user, the proximal portions of each of the catheter 200 and the catheter advancement element 300 (and the guidewire, if present) are configured to be held at a single point by a user. For example, where the catheter and catheter advancement element are advanced and/or withdrawn manually, the single point can be between just a forefinger and thumb of the user.

The components can be advanced together with a guidewire, over a guidewire pre-positioned, or without any guidewire at all. In some implementations, the guidewire can be pre-assembled with the catheter advancement element 300 and catheter 200 such that the guidewire extends through a lumen of the catheter advancement element 300, which is loaded through a lumen of the catheter 200, all prior to insertion into the patient. The pre-assembled components can be simultaneously inserted into the sheath 400 and advanced together up through and past the turns of the carotid siphon. A guidewire may be located within the lumen 368 of the catheter advancement element 300 and parked proximal of the tapered distal end region 346 or proximal of the distal tip for potential use in the event the catheter advancement element without a guidewire does not reach the target location. For example, a distal tip of the guidewire can be positioned about 5 cm to about 40 cm, or about 20 cm to about 30 cm proximal of the distal end region 346 of the catheter advancement element 300. At this location the guidewire does not interfere with the performance or function of the catheter advancement element. The guidewire can be positioned within the lumen of the catheter advancement element such that the distal end of the guidewire is within the catheter advancement element during the step of advancing the assembled system of devices together and is extendable from the catheter advancement element out the distal opening 326 when needed for navigation. In one example, a rescue guidewire is parked within the lumen of the catheter advancement element with a distal end of the guidewire about 0 cm to about 40 cm proximal or about 5 cm to about 35 cm proximal or about 7 cm to about 30 cm of the distal end of the catheter advancement element, preferably about 10 cm proximal of the distal end of the catheter advancement element. The guidewire at this parked position can provide additional support for the proximal portion of the system without affecting the flexibility and performance of the distal portion of the system.

FIG. 1D illustrates a rescue guidewire 500 parked within the lumen 368 of the catheter advancement element 300. In some implementations, the distal end of the guidewire 500 can be positioned inside the lumen 368 approximately flush with (0 cm) the distal opening 326 of the catheter advancement element during advancement through the vasculature. In some implementations, the distal end of the guidewire 500 can be positioned inside the lumen 368 a distance proximal from the distal opening 326 of the catheter advancement element during advancement through the vasculatures. The distance between the distal end of the parked guidewire 500 and the distal opening 326 can be at least about 1.5 cm, at least about 3 cm, at least about 5 cm, at least about 10 cm, at least about 15 cm, at least about 20 cm, at least about 25 cm, at least about 30 cm, up to about 40 cm proximal to the distal opening 326. Positioning the distal end of the parked guidewire 500 closer to the distal opening 326 of the catheter advancement element (e.g., 1.5 cm to about 3 cm proximal to the distal opening 326) such that it extends within the lumen 368 of the distal tip region 346 can support or stiffen the distal tip region 346 and also support the more proximal regions of the catheter advancement element 300. For example, a surgeon may desire to position the distal end of the guidewire closer to the distal opening 326 to increase stiffness of the distal end region of the catheter advancement element 300. Positioning the distal end of the parked guidewire 500 further away from the distal opening 326 of the catheter advancement element (e.g., greater than 5 cm up to about 40 cm proximal to the distal opening 326, preferably about 10 cm) avoids changing the flexibility characteristics of the distal tip region 346 while still supporting the more proximal regions of the catheter advancement element 300.

The tubular portion 360 of the catheter advancement element 300 can have a radiopaque marker band embedded within or positioned over a wall of the tubular portion 360 near the distal end region 346. A first radiopaque marker band 344a can be found at the distal end of the tapered distal end region 346 and a second radiopaque marker band 344b can be found at the proximal end of the tapered distal end region 346. The proximal radiopaque marker band 344b can have a proximal edge, a distal edge, and a width between the proximal and distal edges. When in the advancement configuration, the proximal edge of the radiopaque marker band 344b can align substantially with the distal end of the distal, catheter portion 222 such that the radiopaque marker band 344b remains external to the lumen 223 of the distal, catheter portion 222. At least a portion of the radiopaque marker band 344b can be positioned at the snug point, or the point of the catheter advancement element 300 where the outer diameter is no more than about 0.010" (0.254 mm), preferably between about 0.006" and 0.008" (0.152 mm-0.203 mm) smaller than the inner diameter of the catheter 200 it is positioned within. The at least one snug point of the tubular portion 360 can be located proximal to the distal end region 346 and can be where the taper of the distal end region 346 substantially ends. This allows for full extension of the tapered distal end region 346 outside the distal end of the catheter 200 and the snug point aligned substantially within the distal opening 231 from the lumen 223 of the distal, catheter portion 222 thereby minimizing any distal-facing lip that might be created by the catheter 200. The snug point can be located along at least a portion of a length of the outer diameter of the tubular portion 360 that has a length of at least about 5 cm up to about 10 cm, the outer diameter being substantially uniform or non-uniform.

The use of the catheter advancement element 300 with the tapered distal end region 346 allows for delivery of large bore aspiration catheters, even full-length "over-the-wire" catheters or catheters such as those described herein having a proximal extension. The catheter advancement element 300 can include a pair of radiopaque markers 344a, 344b configured to aid the operator in delivery of the system. The distal marker 344a near the distal-most end 325 of the catheter advancement element 300 can be differentiated from the distal marker 224a on the catheter 200 by its characteristic appearance under fluoroscopy as well as by simply jogging back and forth the atraumatic catheter advancement element 300 to understand the relationship and positioning of the catheter advancement element 300 relative to the catheter 200. The second marker 344b on the catheter advancement element 300 that is proximal to the distal-most tip marker 344a can delineate the taper of the distal end region 346, i.e. where the outer diameter of the catheter advancement element 300 has a sufficient size to reduce the "lip" of the transition between the catheter advancement element 300 and the catheter 200 through which it is inserted and configured to deliver. The markers aid in positioning the catheter advancement element 300 relative to the distal end 215 of the aspiration catheter 200 such that the tip 215 of the catheter 200 is aligned with the taper of the catheter advancement element 300 and the best alignment is facilitated.

The relationship between the distal tip marker 224 of the aspiration catheter 200 is at or ideally just proximal to the taper marker 344b of the catheter advancement element 300 (i.e. the proximal marker identifying the start of the taper) is identifiable with the tandem marker system. The paired elements 224, 344b are in a "tip-to-taper" position. The relative extension between the catheter advancement element 300 and the catheter 200 can be adjusted at the insertion of the system into the RHV. However, the relative extension can become altered with advancement through the sheath or guide catheter. As the system exits the guide catheter, the aspiration catheter 200 and the catheter advancement element 300 can be adjusted to that the tip-to-taper position is assumed as the system traverses the often tortuous proximal vessel (e.g. the cervical internal carotid artery) towards more distal targets. The system of the aspiration catheter 200 and the catheter advancement element 300 can be locked into their relative extension so that the juxtaposition of the catheter advancement element 300 and the aspiration catheter 200 is maintained. As the aspiration catheter 200 is visualized within the sheath distal end or even slightly beyond the distal end of the sheath, the catheter advancement element 300 can be adjusted to assume the proper position relative to the catheter before advancement resumes. The optimum relative extension between the distal marker 224 of the catheter 200 to the taper marker 344b on the catheter advancement element 300 can be maintained through as much of the anatomy as possible to maximize the delivery capability of the catheter advancement element 300 to navigate both tortuosity and to avoid side branches such as the ophthalmic artery. Once a desired site (e.g., proximal to, at, or distal to the radiographic limit of contrast 120) is reached, the catheter advancement element 300 can be held fixed and the aspiration catheter 200 advanced over the catheter advancement element 300 towards the embolus 115, but without crossing the embolus 115 with the catheter 200. Alternatively, the catheter advancement element 300 can be withdrawn proximally and the catheter 200 allowed to ride momentum of stored forces distally towards the embolus 115 as described elsewhere herein. The withdrawal step of the catheter advancement element 300 can be performed manually or automatically.

The catheter advancement element 300 is designed specifically such that the catheter 200 can be delivered without a need for a guidewire. This ability to deliver the catheter 200 without a guidewire (or with a guidewire located within the lumen 368 of the catheter advancement element 300 and parked proximal of the tapered distal end region 346 and/or proximal of the distal opening 326 for potential use) and without crossing the embolus is based, in part, upon the smooth transitions between the outer diameter of the catheter advancement element 300 and the catheter 200 as well as the smooth transition in flexibility between the two. When the catheter advancement element 300 is bent into an arc of greater than 180 degrees, the softness and flexibility creates a smooth arc without severe bends or kinks in the geometry of the catheter. Thus, the catheter advancement element 300 seeks the larger lumens and goes where the majority of blood flow goes as opposed to into the smaller branch arteries. The distal end region 346 of the catheter advancement element 300 can facilitate a strong preference to seek out the larger vessels during advancement into the distal vessels. This propensity to stay within the main channel allows for the advancement of large bore catheters without the aid of a guidewire. The propensity to follow the main channels of blood flow aligns with acute ischemic stroke pathophysiology where major emboli tend to follow these same routes to a point where the embolus lodges and interrupts antegrade blood flow. As well, these major channels are often ideal for placement of access catheters as these conduit arteries allow for smaller catheters to pass into specific target arteries for therapeutic intervention.

Standard neurovascular intervention, and nearly all endovascular intervention, is predicated on the concept that a guidewire leads a catheter to a target location. The guidewires are typically pre-shaped and often find side-branches of off-target locations where the guidewire will bunch or prolapse causing time-consuming nuisances during interventions that often require repeated redirection of the guidewire by the operator to overcome. In addition, this propensity of a guidewire to enter side-branches can be dangerous. Guidewires are typically 0.014" to 0.018" (0.356 mm-0.457 mm) in the neuroanatomy and will find and often traumatize small branches that accommodate this size, which can lead to small bleeds or dissections and occlusion. In a sensitive area like the brain these events can be catastrophic. The tendency of a guidewire to bunch and prolapse can also cause a leading edge to the guidewire that can be advanced on its own or as part of a triaxial system to create dissection planes and traumatize small vessels. Guidewires are also designed to cross the embolus, primarily for the purpose of securing the guidewire to provide support for delivery of a catheter over the guidewire. However, crossing the embolus with the guidewire can increase a risk of dislodging embolic debris, which travels distal to the occlusion site.

In contrast, the catheter advancement element 300 described herein preferentially stays in the larger lumen of a conduit vessel. In the setting of stroke treatment, an embolus is driven to certain anatomies because of the blood flow that the arterial system draws in the cerebral anatomy. The catheter advancement element 300 tends to traverse a path identical to the path an embolus will take, particularly an embolus driven from a location such as cardiac or carotid etiology. The catheter advancement element 300 delivers to the largest lumen within the anatomy even in light of the highly tortuous anatomy and curves being navigated. The catheter advancement element 300 can preferentially take the larger lumen at a bifurcation while also following the current of the greatest blood flow thereby maintaining the general direction and angulations of the parent vessel. In viewing the standard anatomy found in the cerebral vasculature, the Circle of Willis is fed by two vertebral and two carotid conduit arteries. As these four arteries are the access points to the cerebral anatomy—the course of the catheter advancement element 300 can be identified and has been validated in standard cerebral anatomy models.

Figure 2:
FIG. 2 shows an angiogram of a native artery with antegrade bloodflow.

FIG. 2 shows an angiogram of native arteries with antegrade blood flow. The contrast media has replaced the blood and absorbs the x-rays to provide a visible image of the arteries. In the anterior circulation where the conduit artery point of entry for cerebral endovascular procedures is the internal carotid artery (ICA), the catheter advancement element can guide the large-bore catheter to the M1 segment of the middle cerebral artery (MCA) bypassing the anterior communicating artery (ACA) and anterior temporal branch (ATB). The very flexible nature of the catheter advancement element 300 combined with the distal flexible nature of most cerebral catheters combine to allow delivery through severe tortuosity. Independent of the tortuous nature of the course of the arteries, the catheter advancement element 300 tends to navigate the turns and deliver to the largest offspring from a parent artery, for example, ICA to M1 segment of the MCA. The M2 level branching of the M1 can be variable, but is often seen to have two major M2 branches (superior and inferior) and, depending on the anatomy, which can vary significantly between patients, may be seen to bifurcate "equally" or "unequally." If the caliber of the M2 branching is of similar size and angulation, the catheter advancement element 300 may take one of the two branches. If the target for catheter placement is not in a favorable angulation or size of artery, the catheter advancement element 300 may be curved (e.g. via shaping of a malleable distal tip) and directed or a guidewire may be used.

In some anatomies where the M2 bifurcation is "even" in size, a back-and-forth motion may aid in selecting one branch then the other while still avoid the need or use of a guidewire or a curved distal tip of the catheter advancement element. The back-and-forth motion can allow for the catheter advancement element to be directed into either branch of the M2. The catheter advancement element, even when initially straight, achieves some curvature that aids in directing it into a branch vessel. Thus, when an operator encounters an M2 bifurcation and there is a desire to cannulate either branch of an evenly divided bifurcation, selection of either branch is possible using the catheter advancement element without a guidewire.

Thus, main channels such as the ICA, the middle cerebral artery and its tributaries in the anterior circulation will naturally be the pathway of preference for the described catheter advancement element and subsequence large-bore catheter delivery (via access from the ICA). A similar phenomenon can occur in the posterior circulation, which is accessed via the vertebral arteries arising from the subclavian arteries on the right and the left. The catheter advancement element will take the main channels in this circulation as well by traversing the vertebral arteries to the basilar artery and to the major tributaries of the basilar: the posterior cerebral artery and superior cerebellar arteries in the posterior circulation.

Navigation using the catheter advancement element can provide maximal deliverability with minimal vascular trauma. Catheters can cause "razoring" effects in a curved vessel because the blunt end of a large bore catheter can tend to take the greater curve in rounding a vessel when pushed by the operator. This blunt end can gouge or "razor" the greater curve with its sharp edge increasing the risk for dissection along an anatomic plane within the multilayered mid- or large-sized artery or vein (see, e.g. Catheter Cardiovasc. Interv. 2014 February; 83(2):211-20). The catheter advancement element can serve to minimize the edge of these catheters. Positioning the catheter advancement element within the lumen of the large-bore catheter such that the taper marker of the catheter advancement element is aligned optimally with the distal tip marker of the catheter minimizes the edge and thereby eliminates "razoring" as the large-bore catheter is advanced through turns of the vessel. This is particularly useful for the cerebral anatomy. Stroke treatments are typically needed in regions distal to the carotid siphon, particularly distal to the ophthalmic artery takeoff from the greater curve of the severe tortuosity of the final turn of the carotid siphon "S-turn", the "anterior genu" of the carotid siphon typically seen as part of the terminal internal carotid artery (ICA). The specifics of the catheter advancement element in proper alignment within the large bore catheter (the "tip-to-taper" position noted by the distal tip marker) relative to the taper marker of the catheter advancement element maximize the likelihood that razoring and hang-up on the ophthalmic artery are avoided during manual advancement of the catheter system. The taper marker of the catheter advancement element can be positioned at or past the take-off of the ophthalmic artery to minimize these deleterious effects and allows the large-bore catheter to pass the ophthalmic artery without incident. In a relatively straight segment, which is common after passing the siphon, the large-bore catheter can be advanced over the catheter advancement element, which serves still as a guiding element to the target. The transition between the catheter advancement element and the distal edge of the large-bore catheter is insignificant, especially compared to the step changes present with a typical microcatheter or guidewire, which do not prevent hang-ups on branches such as the ophthalmic artery. The catheter advancement element allows for maneuvering of the large-bore catheter clear to the face of the embolus without use of a microcatheter or guidewire and without crossing and/or fragmenting the embolus in any way.

Conventional techniques to treat AIS whether with a stent retriever, aspiration techniques, or a combination of the two, require crossing the target embolus with a guidewire and a microcatheter. Crossing of the embolus with a guidewire and then microcatheter can create fragmentation of the occlusion, which can be friable and thrombotic in nature creating particulate that can be released downstream. The aspiration techniques described herein allow for the embolus to be removed en toto without any crossing of the embolus with any device. The systems described herein need not incorporate a guidewire or microcatheter. And, if a guidewire and microcatheter are used, they need not be advanced to cross the target embolus. Thus, the systems described herein can incorporate relatively large bore catheters that are delivered without disturbing the target embolus, reducing the risk for stroke and downstream effects from fragmentation of the embolus, and having improved efficiency. Additionally, the systems described herein are single-operator systems allowing the operator to work at a single RHV and, in the case of spined components, can manipulate all the elements being used to navigate the anatomy with single-handed "pinches." This can be referred to as "monopoint."

As mentioned above, angiography is the industry standard for imaging cardiovascular anatomy within the body prior to and during a catheterization procedure. Generally, angiography involves injection of contrast media and use of x-ray fluoroscopic image guidance to visualize the occlusion and/or advancement of the catheter systems toward the occlusion site. FIG. 2 shows an angiogram of native arteries with antegrade blood flow. The contrast media has replaced the blood and absorbs the x-rays to provide a visible image of the arteries as described above. This angiogram can provide a "roadmap" for navigating the vasculature with a catheter system. FIG. 3A shows an angiogram including an artery having an occlusion site 105. The angiogram of FIG. 3A as well as the angiograms of FIGS. 2, 3C, 9A, and 9C are all positive fluoroscopy images. The presence of contrast media appears darker and the absence of contrast media appears lighter. The darker regions where the contrast media is present and has absorbed the x-rays are referred to herein as high contrast regions 101. The lighter regions where there is minimal contrast media infiltration are referred to herein as diffuse contrast regions 110. Even lighter regions where there is no contrast media infiltration are referred to herein as low contrast regions 130. FIGS. 5A, 6A, 7A, and 8A are negative fluoroscopy images of angiograms. In these angiograms, lighter regions represent the presence of contrast media and darker regions represent minimal or no contrast media infiltration. The angiogram of FIG. 3A showing the roadmap may be overlaid over the fluoroscopic images throughout the procedure to identify the contrast regions when contrast is no longer present.

Figure 3B:
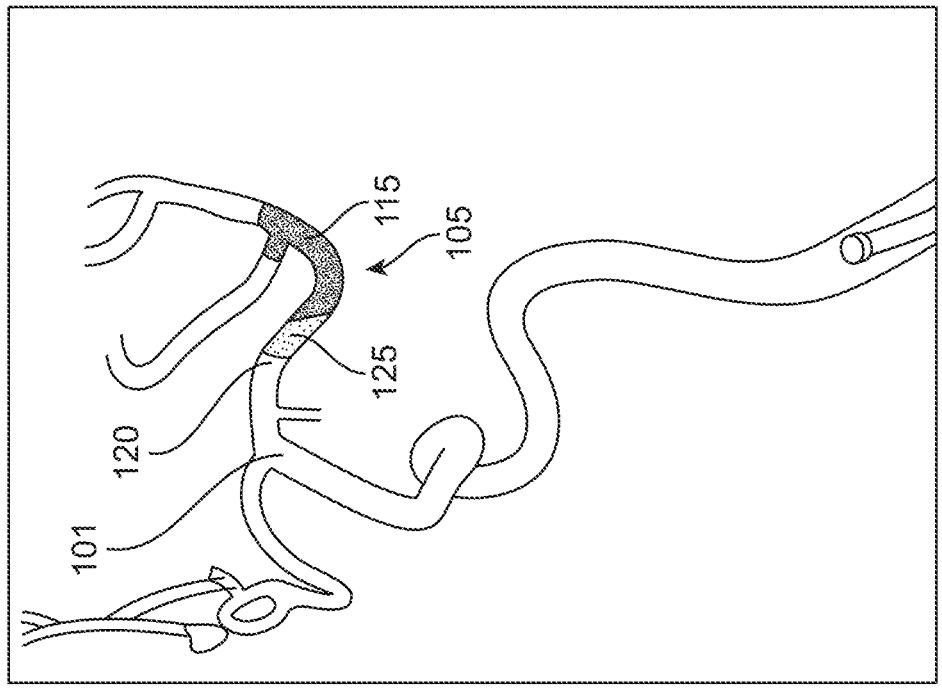
FIG. 3B shows a schematic of the angiogram of FIG. 3A showing an embolus and soft clot material proximal to the embolus.
Figure 3A:
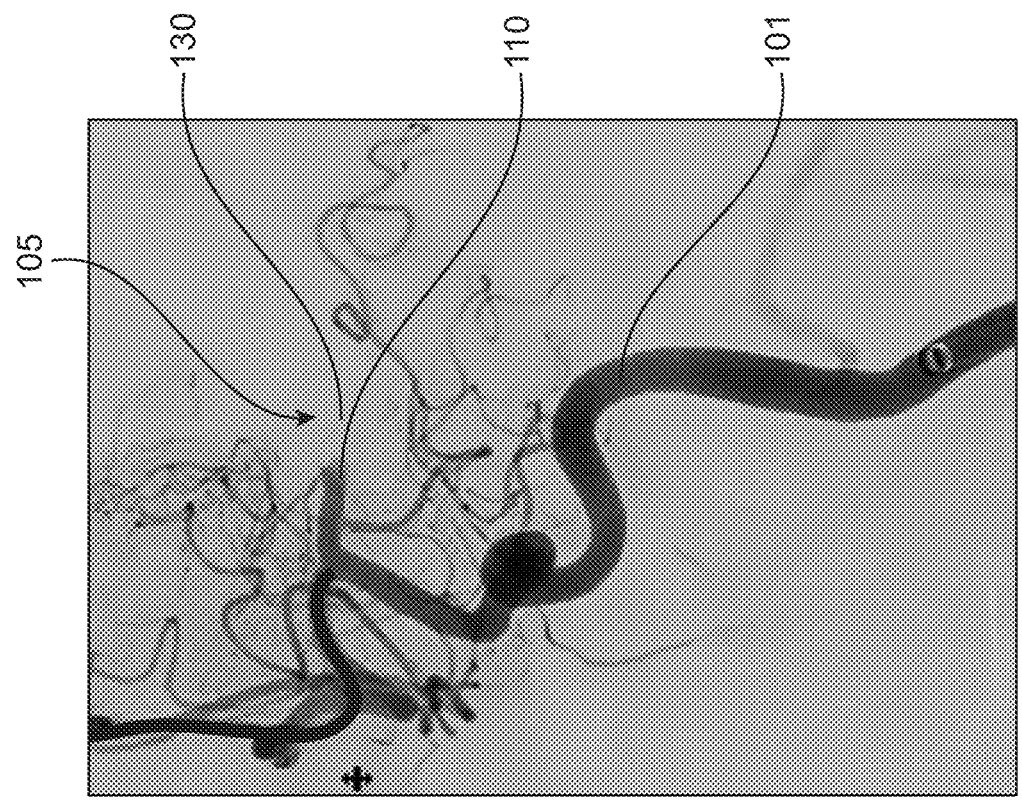
FIG. 3A shows an angiogram of an occlusion site in a cerebral vessel.
Figure 3C:
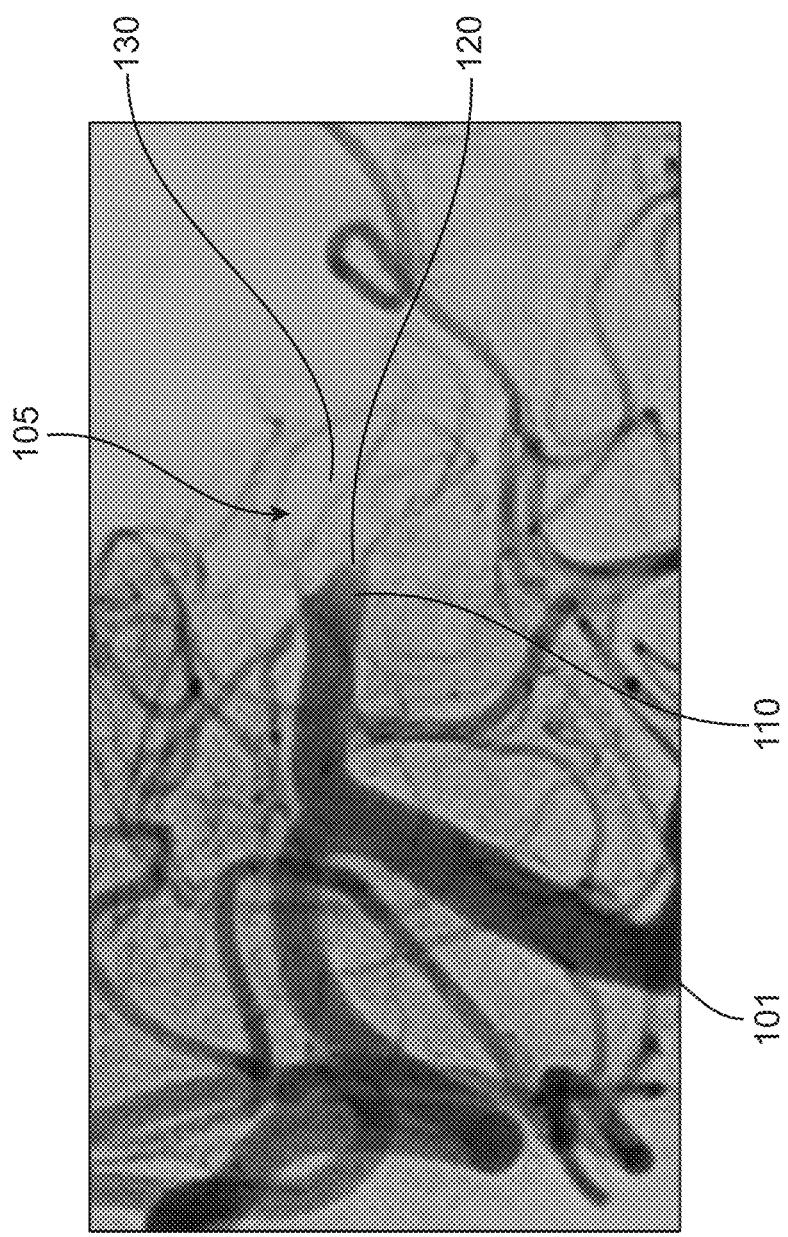
FIG. 3C is a detailed view of the angiogram of FIG. 3A.

FIG. 3B is a schematic representation of the angiogram of FIG. 3A. FIG. 3C is a detailed view of the occlusion site 105 shown in the angiogram of FIG. 3A. The angiogram of FIG. 3C shows a high contrast region 101 in a vessel upstream of an occlusion site 105, a diffuse contrast region 110, an angiographic limit of contrast 120, and a low contrast region 130. As discussed above, the occlusion site 105 can have zones differing in cellular organization, make-up, and/or density that are infiltrated or penetrated by the contrast media to different degrees. As shown in the schematic of FIG. 3B, the contrast media may not infiltrate the denser embolus 115 of the occlusion site 105 and to a lesser degree may not infiltrate the soft clot material 125 creating the angiographic limit of contrast 120 that is visible on angiogram. The embolus 115 may be located within the low contrast region 130 distal (or downstream) to the angiographic limit of contrast 120.

Figure 4A:
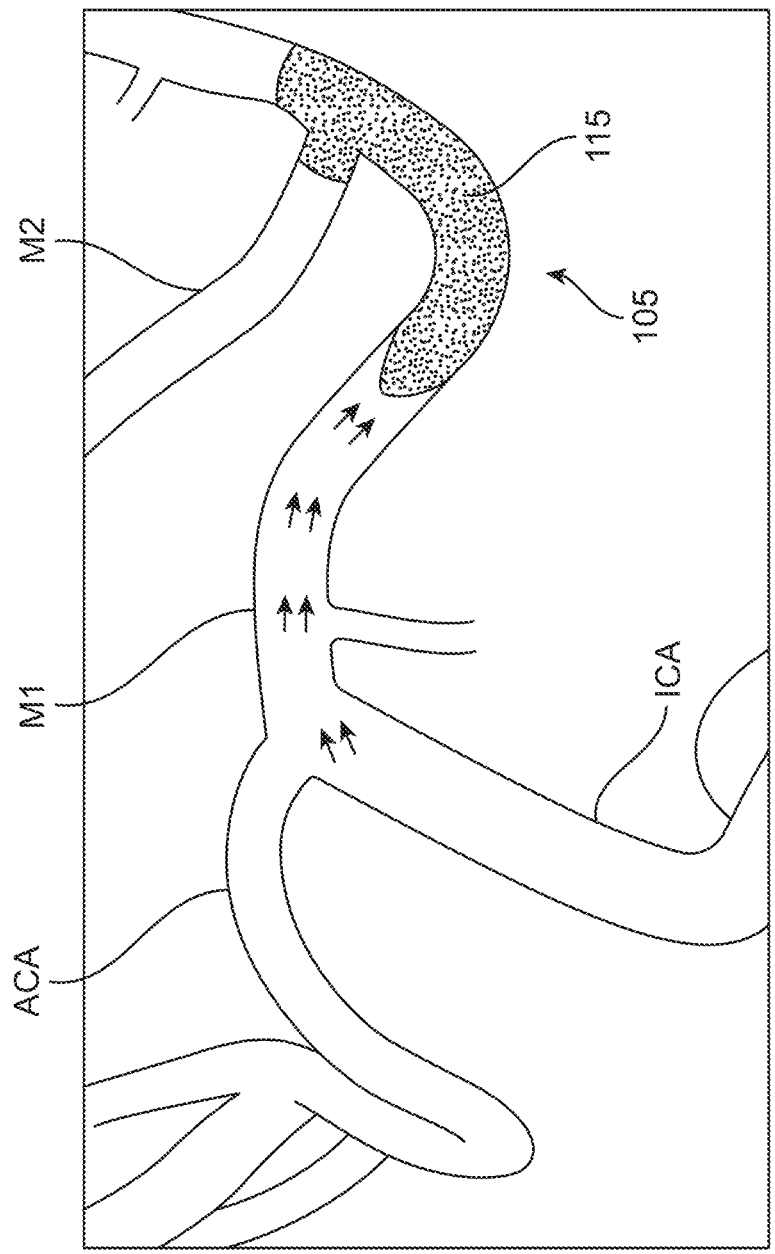
FIG. 4A-4D show schematics illustrating the development of an occlusion site of a cerebral vessel.
Figure 4B:
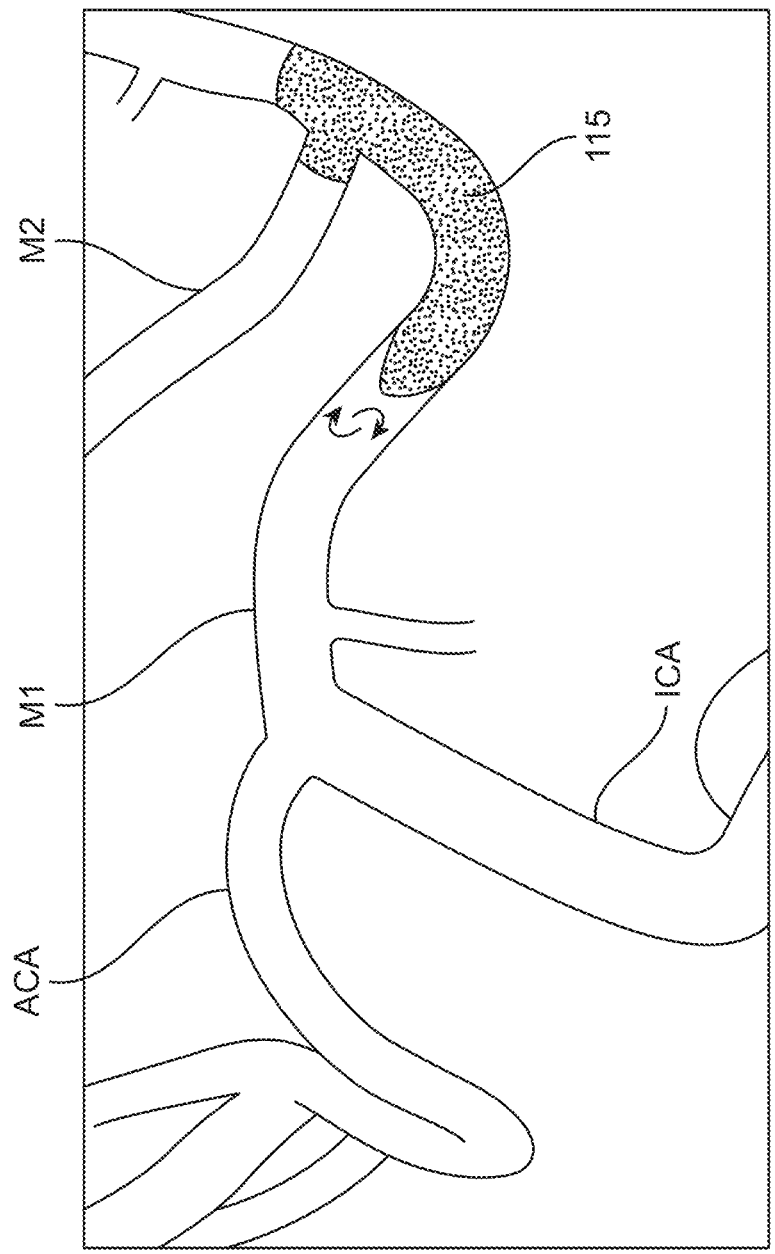
Figure 4C:
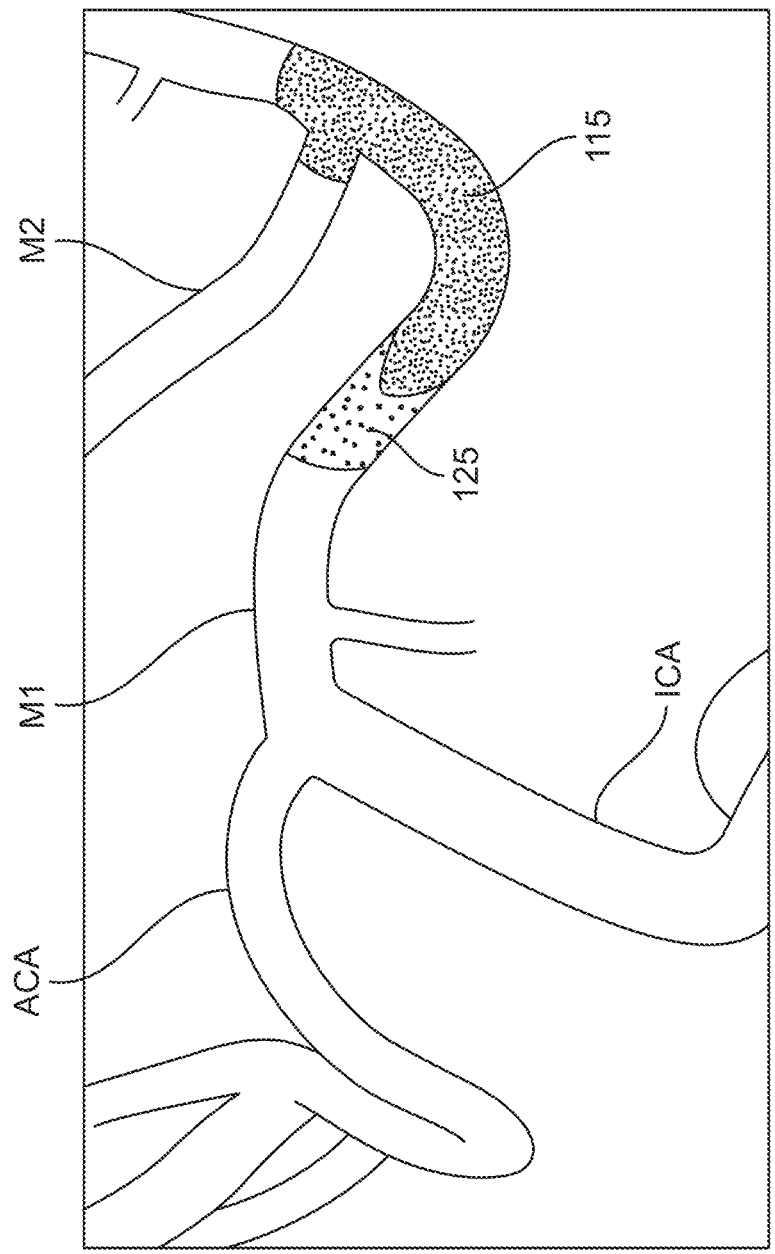
Figure 4D:
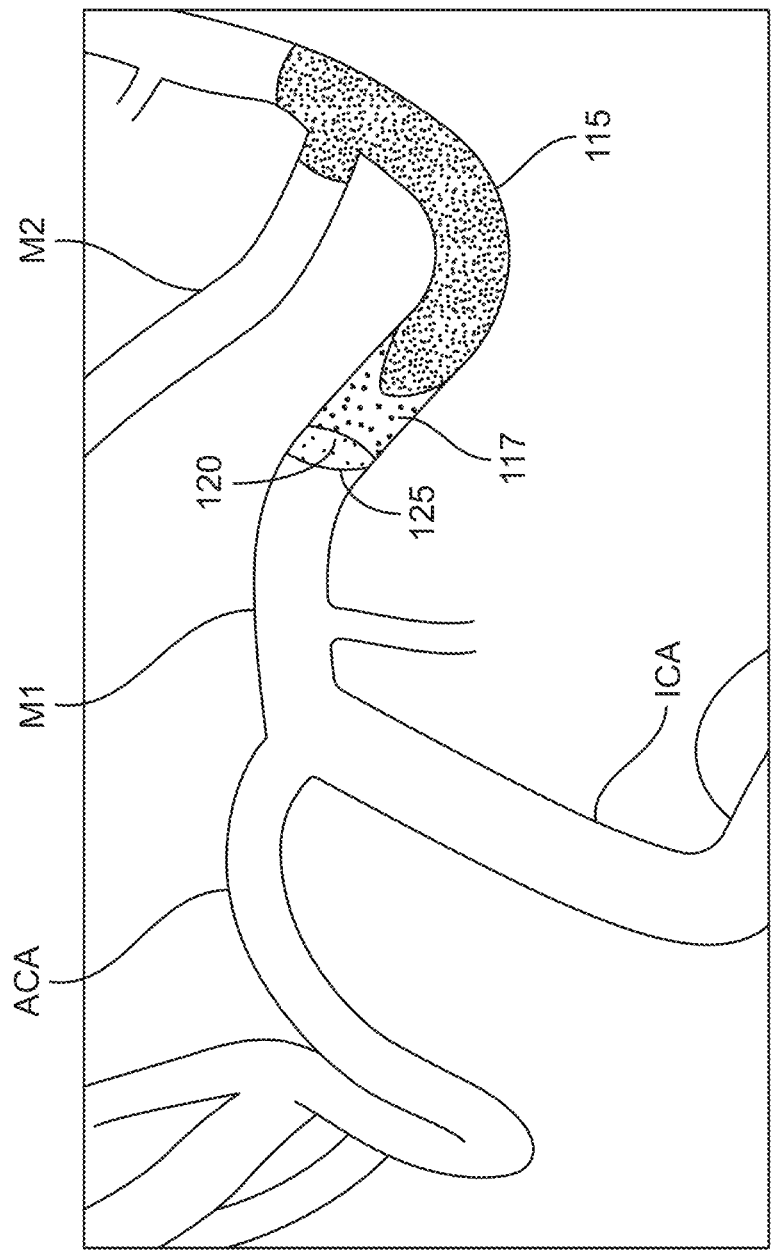

FIGS. 4A-4D are schematics illustrating the development of the occlusion site 105 within the cerebral vessel upon lodgement of the embolus 115 near the bifurcation between the M1 and M2 segments of the middle cerebral arteries (see FIG. 4A). FIG. 4A shows the direction of blood flow from the ICA to the M1 towards the occlusion site 105. Blood flow becomes static in the area proximal to the embolus 115 (see FIG. 4B). Soft clot material 125 can accumulate in situ upstream or proximal of the embolus 115 (see FIG. 4C) due to the static blood flow. In some patients, the contrast agent does not infiltrate the soft clot material 125 that accumulates in situ at the upstream margins of the embolus 115 where flow slows or stagnates. The soft clot material 125 is indistinguishable in the angiogram from the denser embolus 115 and no diffuse contrast region 110 is present. Rather, both the soft clot material 125 and the embolus 115 are part of the low contrast region 130 of the angiogram. In other patients, this soft clot material 125 may be slowly or minimally infiltrated by the contrast media at the margins of the embolus 115 creating a diffuse contrast region 110 on the angiogram proximal to the angiographic limit of contrast 120. In some patients, the soft clot material 125 may develop over time into more organized thrombus 117 (see FIG. 4D). The contrast media may infiltrate the newer soft clot material 125, but not infiltrate the older, denser, organized thrombus 117. In these patients, the angiographic limit of contrast 120 may be distal to a soft clot material 125 and proximal to the organized thrombus 117 such that both the organized thrombus 117 and the embolus 115 are part of the low contrast region 130.

The visualization of the angiographic limit of contrast 120, whether or not a diffuse contrast region 110 is distinguishable from the low contrast region 130 on the angiogram, can be a reference point for optimal positioning of an aspiration catheter to enable one-pass embolectomy. Locating a distal opening of an aspiration catheter at or within the material of the embolus 115 instead of at or within the soft clot material 125 that accumulates proximal or upstream to the embolus 115 can improve the rate of one-pass embolectomy by allowing the aspiration catheter to aspirate or grasp and remove the embolus 115.

Figure 5B:
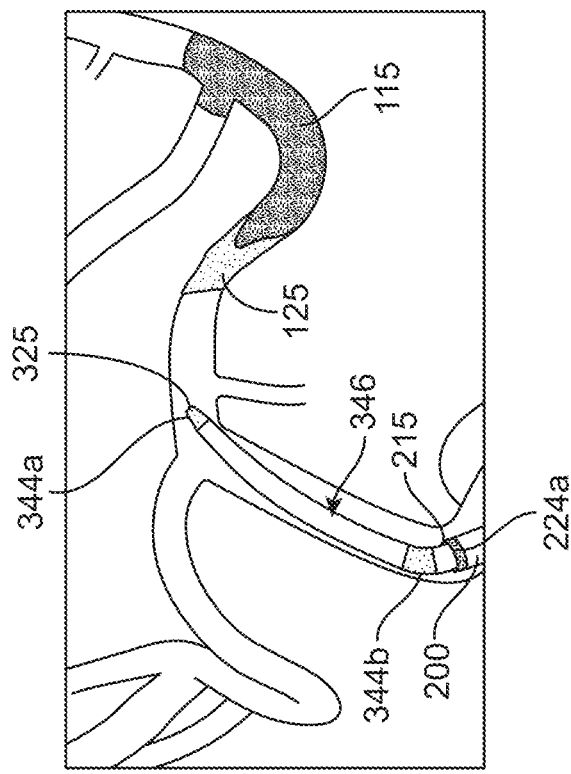
FIG. 5B shows the angiogram of FIG. 5A in schematic.
Figure 5A:
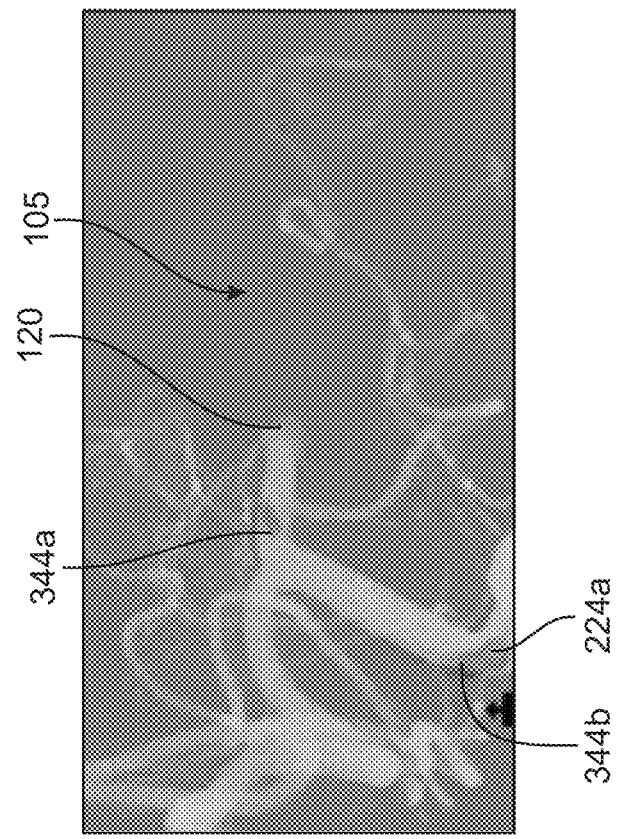
FIG. 5A shows an angiogram of a catheter system advanced towards an occlusion site in a cerebral vessel.

FIG. 5A is an angiogram (negative image) showing an occlusion site 105 in a cerebral vessel of a patient and a system of devices 100 for distal access that are positioned in proximity to the occlusion site 105. FIG. 5B is a schematic illustration of the angiogram of FIG. 5A. FIG. 5B shows the system of devices 100 can include a catheter 200 having a distal-most end 215 having a distal marker 224a. The system of devices 100 can include a catheter advancement element 300 configured to extend through the catheter so that a distal-most end 325 of the catheter advancement element 300 extends out the distal opening 231 and distal to the distal-most end 215 of the catheter 200. The distal-most end 325 of the catheter advancement element 300 can be identified under fluoroscopy by the distal marker 344a and a proximal edge of the tapered distal end region 346 identified by the proximal marker 344b. The system of devices 100 can be advanced as an assembled system with the catheter advancement element 300 extending through the catheter lumen 223, out the distal opening 231, and a distal end region 346 projecting beyond the distal-most end 215 of the catheter 200 and the trio of markers 344a, 344b, 224a visible on the angiogram roadmap. FIGS. 5A and 5B show the distal end region 346 of the catheter advancement element 300 traversing from the ICA into the M1 while the catheter 200 is advanced together with the catheter advancement element 300.

Figure 6B:
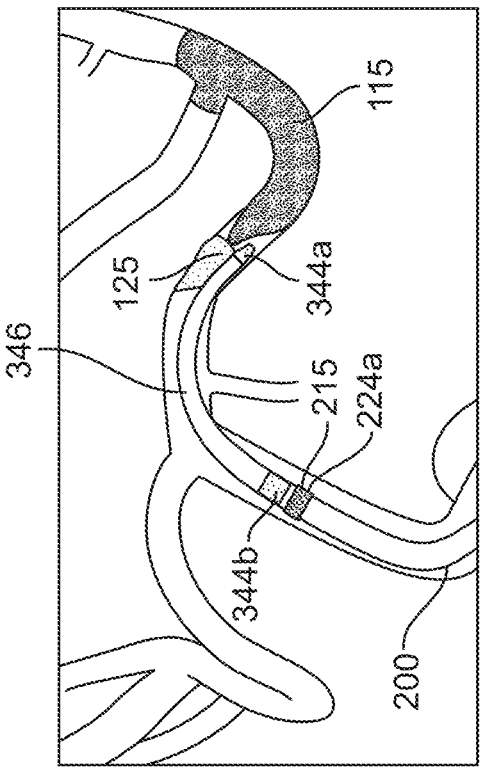
FIG. 6B shows the angiogram of FIG. 6A in schematic.
Figure 6A:
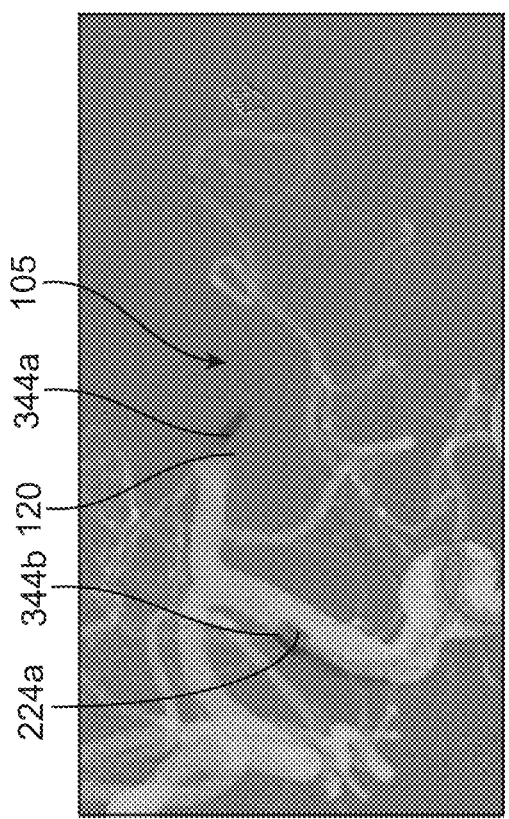
FIG. 6A shows an angiogram of the catheter system of FIG. 5A advanced further into the cerebral vessel.

The distal end region 346 of the catheter advancement element 300 can be tapered, soft and flexible so that it can be used to locate a desired location past the angiographic limit of contrast 120 for application of aspiration by the aspiration catheter 200. As shown in FIGS. 6A and 6B, the softness, tapering, and sizing of the catheter advancement element 300 distal end region 346 allows for the distal most end of the distal end region 346 to pass through the soft clot material 125 and probe the embolus 115 without crossing the embolus. In some implementations, the distal end region 346 can find and/or create space in or beside the embolus 115 or slide between at least a portion of the embolus 115 and the vessel wall (see FIGS. 6A-6B). The catheter advancement element 300 can be advanced to position the distal-most end 325 of the catheter advancement element 300 without crossing the embolus 115. Unlike a guidewire, the catheter advancement element 300 is unlikely to cross the embolus 115 due to the extremely flexible distal tip region and the tapered walls of the distal tapered region 346. Instead the tapered distal region 346 finds a natural resting point or stopping point where further advancement is prevented or difficult. If the tapered distal end region 346 of the catheter advancement element is advanced beyond this natural stopping point and further advancing pressure is applied, the catheter advancement element can begin to buckle and/or prolapse giving the feedback that the desired advancement has been achieved. If this buckling is between the markers 344a and 344b the buckling can be seen angiographically as the marker 344b moving distally without corresponding motion of the marker 344a. Alternatively, the contact between the tapered distal end region 346 and the embolus or dense clot material can provide feedback, for example, tactile feedback to a user handling the tools manually, that the natural resting place has been reached. If the user attempts to advance the tapered distal end region 346 of the catheter advancement element 300 beyond the natural stopping point this can result in traumatizing or fragmenting of the embolus.

"Crossing the embolus" as used herein is means that at least some portion of the device crosses to a downstream or distal side of the embolus relative to the site of insertion. Crossing the embolus increases the risk of embolic material being knocked loose from the embolus and traveling downstream to create new occlusion sites. The catheter advancement element 300 can be advanced as far as possible without buckling of the catheter advancement element 300. Instead of crossing the embolus, the catheter advancement element can interrogate the treatment site to locate a proximal face of the embolus 115 while maintaining structural integrity of both the catheter advancement element 300 and the embolus 115. In some instances, the tapered distal end region 346 of the catheter advancement element 300 can be used to dissect past or separate the soft clot material 125 accumulated at the proximal face of the embolus 115 and to probe the denser material of the embolus 115. FIG. 6A is an angiogram that shows an occlusion site 105 that forms a low contrast region. The distal marker 344a of the catheter advancement element 300 is visible and positioned beyond the angiographic limit of contrast 120 within the low contrast region. FIG. 6B illustrates that the distal-most end 325 of the catheter advancement element 300 has advanced past the soft clot material 125 proximal to the embolus 115 and abuts against a proximal face of the embolus 115. The distal end region 346 of the catheter advancement element 300 has found the proximal face without crossing the embolus 115. The position of the proximal marker 344b and the marker 224 of the catheter 200 confirm that no buckling of the catheter advancement element 300 has occurred and the pressure applied by the system on the embolus 115 is relatively small. In the embodiment of FIG. 6B, the distal-most end 325 has passed between the soft clot material and the vessel wall.

In some implementations, the catheter advancement element 300 can be fixed by a user to remain in this position shown in FIG. 6B and the catheter 200 advanced over it to the treatment site, past the angiographic limit of contrast, and/or until the two components are tip-to-tip and distal markers 344a, 224a aligned. FIGS. 7A-7B show the catheter 200 advanced over the catheter advancement element 300 and both components advanced past the angiographic limit of contrast 120. The distal end 215 of the catheter 200 guided by the catheter advancement element 300 finds a resting point at a treatment site that is located past the angiographic limit of contrast 120. The catheter 200 can be advanced through the soft clot material 125 to position the distal end 215 of the catheter near or at a proximal face of the embolus 115 (FIG. 7B). In some implementations, the catheter 200 can be advanced until resistance is felt by a user indicating the distal end 215 is positioned at the proximal face of the embolus 115. The catheter 200 can be advanced so that the distal end 215 of the catheter 200 is urged against the proximal face of the embolus 115 slightly compressing the embolus 115. The catheter 200 can be positioned so that the distal end 215 of the catheter 200 is located past the proximal face of the embolus 115, but without crossing the embolus 115. Once the catheter 200 is positioned at the treatment site at one of the locations described above, the catheter advancement element 300 can be withdrawn and aspiration pressure applied to capture occlusive material at, within, or through the distal end 215 of the catheter 200 (FIGS. 8A-8B).

In other implementations, the catheter 200 can be advanced to seat with the embolus 115 as the catheter advancement element 300 is withdrawn. In this method, the catheter 200 can be advanced using the catheter advancement element 300 for navigation to a location that is a distance away from the proximal face of the embolus 115 (e.g., near the angiographic limit of contrast 120). The distal catheter portion 222 can become compressed during advancement through the tortuous anatomy. As the catheter advancement element 300 is withdrawn a distance relative to the distal end of the catheter 200, stored energy or compressive forces within the catheter system get released causing the distal catheter portion 222 to move distally. The catheter 200 can be allowed to ride the forward momentum as the forces are released moving the distal end of the catheter towards the embolus 115. In the implementation of FIGS. 8A and 8B, the user advances the distal end marker 344a of the catheter 200 under angiography past the angiographic limit of contrast as shown in FIGS. 7A and 7B and then additional forward movement can occur passively during removal of the catheter advancement element 300 to achieve the position shown in FIG. 8B. A user may advance the distal end of the catheter 200 only as far as where the contrast ends or can advance the distal end right up to a location that appears to be the proximal face of the embolus. If the distal end of the catheter is advanced to a more proximal site (e.g., proximal to or at the angiographic contrast limit) and allowed to ride the momentum, the catheter may gently seat itself near or against the proximal face of the embolus. If the distal end of the catheter is advanced to a more distal site (e.g., against the proximal face of the embolus) and allowed to ride the momentum, the catheter may embed itself into the embolus and/or compress the embolus slightly. This creates a better seal between the embolus and the distal end of the catheter to more effectively aspirate and engulf the embolus.

The forward catheter movement during removal of the catheter advancement element 300 can be supplemented by user applied force (manually or automatically) and facilitated by the internal vacuum generated by the withdrawal of the occlusive catheter advancement element 300 and the piston arrangement or "plunger" effect described elsewhere herein. Engulfment of the embolus 115 can create additional space for the catheter to advance into as more embolic material is engulfed by the distal end of the catheter. Thus, the withdrawal of the catheter advancement element 300 creates a feed-forward mechanism of embolus engulfment involving distal motion of the catheter and internal vacuum within the catheter that can occur prior to applying external vacuum at the proximal RHV of the base sheath. Withdrawal of the catheter advancement element can simultaneously create distal motion of the catheter due to release of stored forces and internal vacuum within the catheter. The internal vacuum can, in turn, cause more distal motion of the catheter. Thus, the distal motion of the catheter can be due to both the catheter passively riding the momentum of the stored forces, and also an active drawing of the catheter towards the embolus due to the internal vacuum. The catheter advancement element can be used to deliver the catheter to a position relative to the angiographic limit of contrast and the catheter allowed to nest with the target embolus located beyond this position and without the presence of the catheter advancement element (or guidewire) by virtue of the distal motion and internal vacuum created upon removal of the catheter advancement element. Thus, the catheter advancement element functions not only to deliver the catheter to a distal location near the embolus more safely than a guidewire, but also to automatically trigger or actuate forward motion of and suction through the catheter when it is withdrawn to more optimally seat the catheter with the embolus and successfully capture the embolus to achieve one-pass aspiration embolectomy.

Figure 9B:
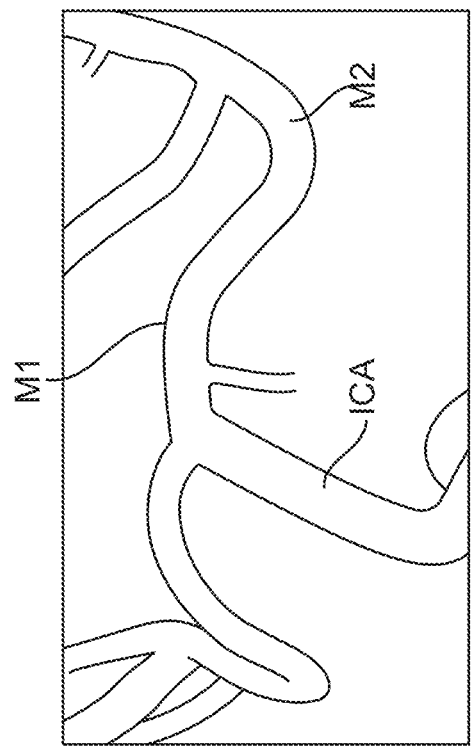
FIG. 9B is the angiogram of FIG. 9A in schematic.
Figure 9A:
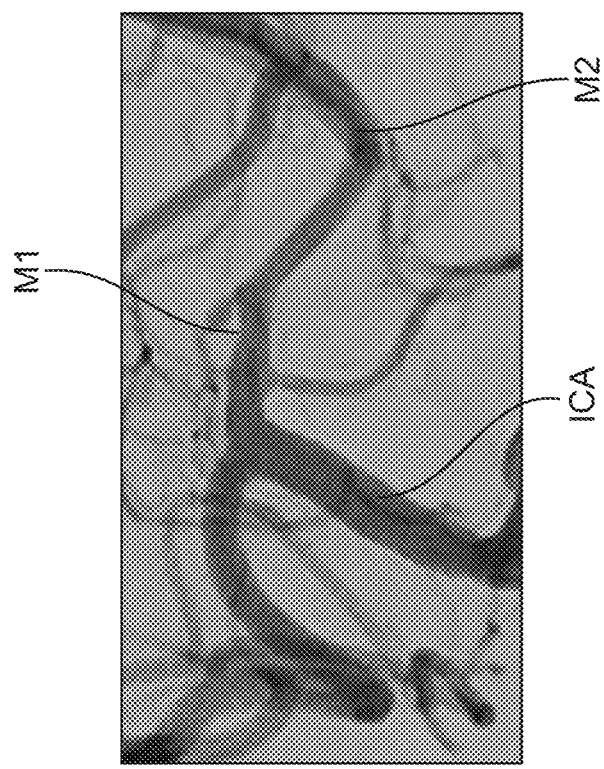
FIG. 9A shows an angiogram of the previously occlusive site of the cerebral vessel of FIG. 5A after removal of the embolus.
Figure 9C:
FIG. 9C shows an angiogram of the previously occlusive site after removal of the embolus.

FIGS. 9A-9C illustrate complete removal of the embolus and resolution of the occlusion site.

Various methods of using the catheter systems described herein, including leveraging this plunger effect and distal movement of the catheter to seat with the embolus, will be described in more detail below.

Figure 10:
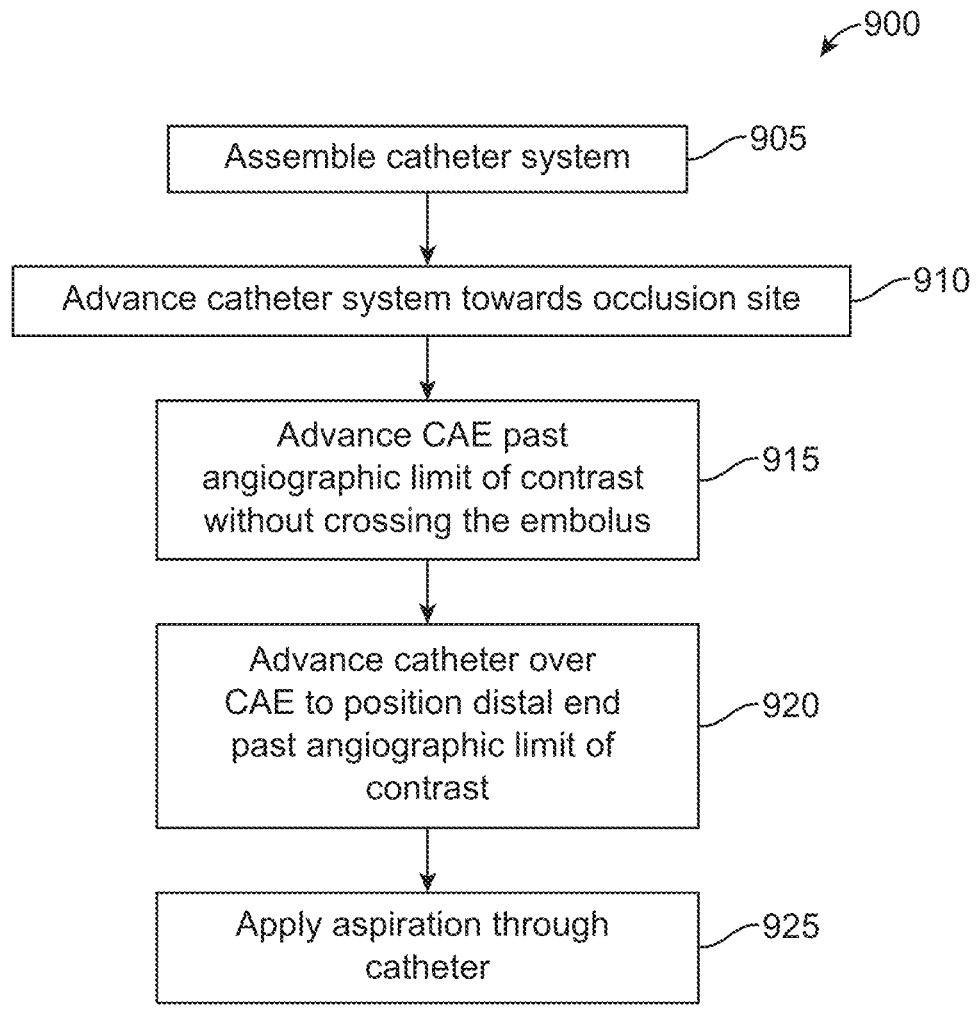
FIG. 10 is a flow diagram of a method of aspiration embolectomy in a cerebral vessel.

FIG. 10 is a flow diagram showing an implementation of a method 900 of using the catheter systems described herein to remove an embolus in a cerebral vessel of a patient. The catheter system 150 can be assembled so the tapered distal end region 346 of the catheter advancement element 300 extends distal to the distal end 215 of the aspiration catheter 200 (box 905). The assembled catheter system 150 can be advanced together, for example, through the internal carotid artery, towards an occlusion site 105 in a cerebral vessel of a patient that is visible on angiogram (box 910). Advancing the assembled system together can include advancing the aspiration catheter 200 and the catheter advancement element 300 simultaneously in a fixed relationship. Alternatively, the assembled system can be advanced together past a certain part of the anatomy, such as beyond the petrous portion of the ICA, the carotid siphon, the origin of the ophthalmic artery, or other areas, and then advanced in a stepwise manner with the tapered distal end region 346 remaining distal to the distal end 215 of the aspiration catheter 200 during the stepwise advancement. The occlusion site 105 can include the angiographic limit of contrast 120 and an embolus 115 downstream of the angiographic limit of contrast 120. The catheter advancement element (CAE) 300 can be advanced to a location past the angiographic limit of contrast 120 without crossing the embolus 115 (box 915). The catheter 200 can be advanced over the catheter advancement element 300 to position the distal end 215 of the catheter 200 at a treatment site located past the angiographic limit of contrast 120 (box 920). Aspiration can be applied to the catheter 200 (box 925).

Advancing the catheter advancement element 300 in the method of FIG. 10 can include positioning the distal end 325 of the catheter advancement element 300 between a portion of the embolus 115 and the vessel wall. Advancing the catheter advancement element 300 can include positioning the distal end 325 of the catheter advancement element 300 without crossing the embolus 115 with the distal end 325 of the catheter advancement element 300. Advancing the catheter advancement element 300 can include positioning the distal end 325 of the catheter advancement element 300 as far as possible without buckling of the catheter advancement element 300. Advancing the catheter advancement element 300 can include interrogating the treatment site to locate the proximal face of the embolus 115. Advancing the catheter advancement element 300 can include using the tapered distal end region 346 of the catheter advancement element 300 to dissect past the soft clot material 125 at the proximal face of the embolus 115 and to probe denser material of the embolus 115.

Advancing the catheter 200 in the method of FIG. 10 can include positioning the distal end 215 of the catheter 200 at a proximal face of the embolus 115, for example, through soft clot material 125 proximal of the embolus 115 to reach the proximal face. Positioning the distal end 215 of the catheter 200 at the proximal face of the embolus 115 can compress the embolus 115. Advancing the catheter 200 can also include positioning the distal end 215 of the catheter 200 past the proximal face of the embolus 115 without crossing the embolus 115. Advancing the catheter 200 can also include positioning the distal end 215 of the catheter 200 past the angiographic limit of contrast 120 until resistance is felt indicating the proximal face of the embolus 115.

The catheter 200 can be advanced over the catheter advancement element 300 and the catheter advancement element 300 removed after the catheter 200 is at the treatment site. Alternatively, the catheter advancement element 300 can be removed prior to or during catheter advancement to the treatment site described in more detail below. In some implementations, the catheter 200 can be advanced over the catheter advancement element 300 to a location at or near the angiographic limit of contrast 120 followed by withdrawal of the catheter advancement element 300, which allows the catheter 200 to advance further distally to toward the embolus 115. The act of withdrawing the catheter advancement element 300, particularly when the anatomy to reach the treatment site is very tortuous, can improve the chances of first-pass aspiration embolectomy by causing the distal catheter portion 222 to ride forward into the face of the embolus 115. This forward motion of the catheter 200 upon withdrawal of the catheter advancement element 300 may be caused by forces stored in the catheter 200 during navigation through the tortuous anatomy of the catheter system 150. The stored forces can be released upon withdrawal of the catheter advancement element 300 through the lumen 223 of the catheter 200 to automatically or passively drive the catheter 200 distal end 215 distally towards the embolus 115. Allowing the distal end 215 of the aspiration catheter 200 to ride the momentum of the forces released results in the distal end 215 of the catheter 200 nesting with or embedding in the proximal face of the embolus 115 in a natural and automatic manner without any external force applied by a user to advance the catheter 200 (although some manual pressure can be applied). The stored forces discussed above may be described as tension, energy, forces, or axial compression occurring in the catheter during delivery due to friction during advancement through the anatomy. The passive forward motion due to release of stored forces in the catheter can advance the distal end 215 of the catheter 200 forward from a few millimeters to a few centimeters. For example, the passive forward motion may be between about 2 mm and about 30 mm. In order to allow the catheter to ride forward to the face of the embolus 115, the user avoids the typical technique of actively pulling back on the proximal end of the catheter to maintain the position of the distal end 215 of the catheter during withdrawal of the catheter advancement element.

Although several figures illustrate the catheter advancement element 300 and subsequently the catheter 200 advanced between the embolus and the vessel wall, it should be understood that this is only one example of the position of the distal-most ends of the catheter system. The distal-most end 325 of the catheter advancement element 300 can alternatively be used to probe softer areas of the embolus that are not along the vessel wall and burrow partially into the embolus, rather than between the embolus and the vessel wall, to guide advancement of the catheter 200. As an alternative to locating the distal end of the catheter 200 between the embolus 115 and the vessel wall, the catheter distal end 215 can be engaged with a proximal face of the embolus 115, embedded into a face of the embolus 115, or embedded into the bulk of the embolus 115. Further, when the catheter 200 external diameter is substantially matched to the inner diameter of the vessel at the location of the embolus, the catheter distal end 215 can be advanced to partially engulf or surround a portion of the embolus 115.

Withdrawing the catheter advancement element 300 relative to the catheter 200 can create an immediate vacuum within the distal end region of the catheter 200 without any external aspiration being applied to the catheter system at the proximal end region (e.g., through the RHV of the base sheath). The plunger effect is due, in part, to the size difference between the outer diameter of the catheter advancement element 300 and the inner diameter of the catheter 200. The tolerance between the components is small enough (e.g., between about 0.003" and 0.015" (0.0762 mm-0.381 mm)) that the catheter advancement element 300, particularly when the guidewire and/or liquid within the lumen of the catheter advancement element 300 or a syringe, RHV, or other closed component is coupled at the proximal luer 364 of the catheter advancement element 300 creates a closed system, acts like a plunger in a syringe upon withdrawal of the catheter advancement element. The internal vacuum created draws embolic material towards or into the distal end 215 of the catheter 200 and also helps to drive the catheter forward. The creation of an internal vacuum in combination with the catheter 200 being passively driven in a distal direction towards the embolus 115 can improve outcomes of aspiration-only embolectomy.

The method of FIG. 10 can include a step of injecting contrast agent into the cerebral vessel to visualize the occlusion site by angiogram. The contrast agent can form a plurality of visible zones. A first zone can be a high contrast region located proximal to the angiographic limit of contrast. The high contrast region can identify blood flow through the cerebral vessel. A second zone can be a low contrast region located distal to the angiographic limit of contrast. The low contrast region can infiltrate slowly or minimally with contrast agent. The low contrast region can identify a location of the embolus and/or soft clot material proximal of the location of the embolus. A diffuse contrast region may be located between the high contrast region and the low contrast region indicating softer or less dense clot material. The catheter advancement element 300 can be positioned so that the distal-most end 325 is past the low contrast region and the distal-most end 215 of the catheter 200 is positioned past the low contrast region.

Figure 11:
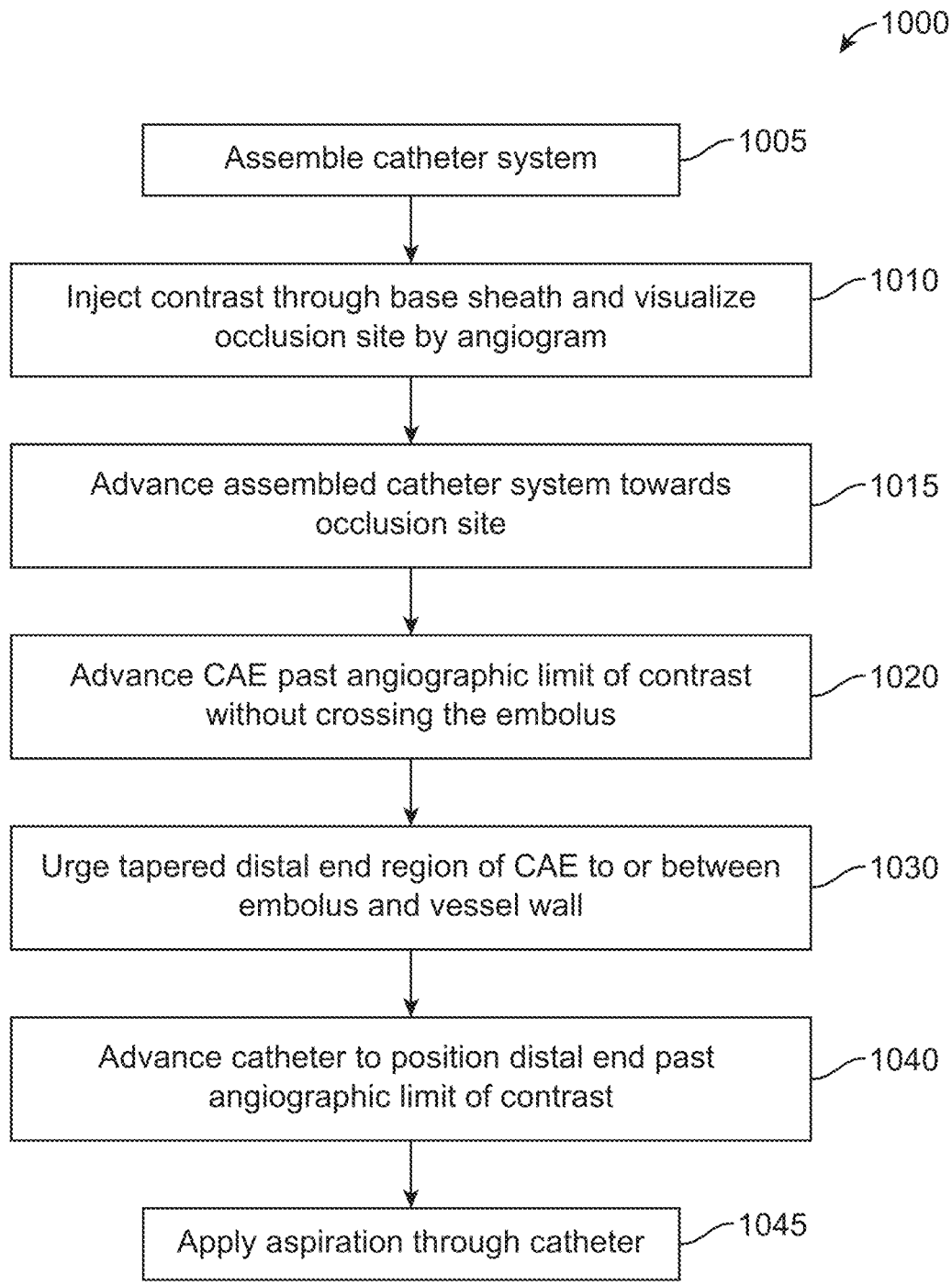
FIG. 11 is a flow diagram of an interrelated implementation of a method of aspiration embolectomy in a cerebral vessel.

FIG. 11 is a flow diagram showing another method 1000 of using the catheter systems described herein. The catheter system 100 can be assembled (box 1005). The base sheath 400 of the catheter system 100 can be advanced from a femoral access site to the level of the carotid artery. Additionally, the catheter advancement element 300 can be assembled with the catheter 200 such that the tapered distal end region 346 extends distal to the distal end 215 of the aspiration catheter 200. Contrast can be injected through the base sheath 400 and the occlusion site 105 visualized by angiogram (box 1010). The assembled catheter system 150 can be advanced together towards the occlusion site (box 1015). The occlusion site 105 can include the angiographic limit of contrast 120 and an embolus 115 downstream of the angiographic limit of contrast 120. The catheter advancement element 300 can be advanced to a location past the angiographic limit of contrast 120 without crossing the embolus 115 (box 1020). The tapered distal end region 346 of the catheter advancement element 300 can be urged to seat with a proximal face of the embolus 115. The tapered distal end region 346 can also be urged between the embolus 115 and the vessel wall (box 1030) to enlarge and/or create space between the embolus 115 and the vessel wall. The catheter 200 can be advanced to position the distal end 215 of the catheter 200 at a treatment site located past the angiographic limit of contrast 120 (box 1040). Aspiration can be applied through the catheter 200 (box 1045).

Although aspiration has been described as being applied after the catheter 200 is positioned at the treatment site, another method starts application of aspiration as the catheter 200 is being advanced to position the distal end 215 at the treatment site. In some patients, an actual space exists between the embolus 115 and the vessel wall. The catheter advancement element 300 can find this space. In other patients, there is no actual space that exists and the tapered distal end region 346 of the catheter advancement element 300 can create the space between the embolus 115 and the vessel wall. For example, it can peel or bluntly dissect between the vessel wall and at least a portion of the embolus 115. The separation of at least a portion the embolus 115 (e.g., a proximal portion) from the vessel wall can improve aspiration of the embolus. This peeling or blunt dissection of the portion of the embolus 115 from the vessel wall can reduce adherence of the embolus to the vessel wall and increase the likelihood of a first-pass aspiration because the adhesion of the embolus 115 to the vessel wall is loosened by the catheter advancement element 300. In still further patients, the tapered distal end region 346 of the catheter advancement element 300 seats with a proximal face of the embolus 115.

The distal end region 346 of the catheter advancement element 300 can be advanced to being positioned within the soft clot material 125 proximal to the proximal face of the embolus 115, within the embolus 115, or distally past the face of the embolus 115. The catheter advancement element 300 does not cross the embolus. The softness and taper of the distal end region 346 can prevent the catheter advancement element 300 from crossing the embolus 115 unlike a guidewire. In some implementations, the soft clot material 125 may be visible on an angiogram or other imaging technique and distinguishable from both the high contrast region and low contrast region as a diffuse contrast region located between the high contrast region and the low contrast region. There may be an interface between the soft clot material and the embolus because the soft clot material may be penetrated to some extent by the injected contrast agent whereas the embolus may not be penetrated by contrast or only minimally penetrated. In this implementation, the catheter advancement element may be advanced to a location relative to the diffuse contrast region or to the interface between the diffuse contrast region and the low contrast region. For example, the catheter advancement element may be advanced to the interface between where the soft clot material is located (i.e., diffuse contrast region) or beyond the soft clot material that may indicate the location of the embolus (i.e., low contrast region). The tapered distal end region of the catheter advancement element is very soft and flexible so that it naturally or automatically stops approximately at or millimeters beyond the interface between the soft clot material and the embolus. In some implementations, the tapered distal end region of the catheter advancement element can advance beyond the proximal face of the embolus finding or creating a space between at least a portion of the embolus and the vessel wall. If the tapered distal end region of the catheter advancement element is advanced beyond this natural stopping point and further advancing pressure is applied by a user, the catheter advancement element can begin to buckle and/or prolapse giving the user feedback that the desired advancement has been achieved. This resistance can be felt by a user prior to actual buckling. The tapered catheter advancement element can provide the user with tactile feedback of the position of the distal end region of the tapered catheter advancement element with respect to the interface between the soft clot material and the embolus. The markers on the catheter advancement element alone or in combination with the markers of the catheter can also confirm by angiogram the lack of buckling.

Advancing the catheter in the method of FIG. 11 can include positioning the distal end 215 of the catheter 200 at a proximal face of the embolus 115, for example, through soft clot material 125 proximal of the embolus 115 to reach the proximal face. Positioning the distal end 215 of the catheter 200 at the proximal face of the embolus 115 can compress the embolus 115. Advancing the catheter 200 can also include positioning the distal end 215 of the catheter 200 past the proximal face of the embolus 115 without crossing the embolus 115. Advancing the catheter 200 can also include positioning the distal end 215 of the catheter 200 past the angiographic limit of contrast 120 until resistance is felt indicating the proximal face of the embolus 115. The catheter 200 may also be advanced employing the forward motion caused by release of forces in the catheter system upon withdrawal of the catheter advancement element 300 back through the catheter lumen, as described elsewhere herein.

The tapered catheter advancement element 300 can be advanced together with the aspiration catheter 200 through the internal carotid artery with the tapered distal end region 346 of the catheter advancement element 300 positioned distal of the distal end 215 of the aspiration catheter 200. The tapered catheter advancement element 300 can then be advanced with respect to the aspiration catheter 200 into or beside the embolus 115 to an aspiration location. Most often, the tapered catheter advancement element 300 can be advanced to the final aspiration location without the use of a guidewire. However, a guidewire may be positioned within the lumen of the tapered catheter advancement element 300 and parked proximal of the tapered distal end region 346 for potential use in the event that the tapered catheter advancement element 300 without the guidewire does not reach the embolus 115. The guidewire may help to close the catheter system 150 such that withdrawal of the catheter advancement element 300 creates automatic aspiration through the catheter 200 as described elsewhere herein. Alternately, the guidewire may be removed prior to withdrawal of the catheter advancement element 300. FIGS. 7A-7B show the distal end 215 of the catheter 200 as seen by the marker band 224*a* has been brought up over the tapered catheter advancement element 300 to a location within or past the soft clot material. The tapered catheter advancement element 300 can then be withdrawn proximally in preparation for aspiration of the embolus 115. FIGS. 8A-8B show the distal end 215 of the catheter 200 as seen by the marker band 224*a* advanced distally due to released forces in the catheter past the interface between the soft clot material 125 and the embolus 115 and the catheter partially surrounds the proximal end of the embolus, also referred to as the embolus tail.

The distal end 215 of the aspiration catheter 200 can be advanced beyond the soft clot material 125, within the embolus 115, or beyond the diffuse contrast region 110, but does not cross the embolus 115. The distal end 215 of the aspiration catheter 200 can be advanced to a location that is past the soft clot material 125 and proximal to the location of the embolus 115. The distal end 215 of the aspiration catheter 200 can be advanced to a location that is past the soft clot material 125 and past at least a portion of the embolus 115. Advancing the distal end 215 of the aspiration catheter 200 past at least a portion of the embolus 115 may compress the embolus 115 slightly between where the embolus 115 is still adhered to the vessel wall and the distal end 215 of the catheter 200. The distal end 215 of the aspiration catheter 200 while it can advance beyond at least a portion of the embolus 115 preferably does not cross the embolus 115.

The aspiration catheter 200 need not be advanced over the tapered catheter advancement element 300 held fixed at the RHV to reach the face of the embolus 115. The catheter advancement element 300 can be withdrawn relative to the catheter 200 prior to the catheter 200 reaching the proximal face of the embolus 115.

The catheter advancement element 300 is designed to have a soft, flexible tapered distal end region 346 that remains available outside the aspiration catheter 200 during advancement to interrogate the embolus 115. As discussed above, forces may be stored in the catheter 200 during navigation of the catheter system through the tortuous anatomy. The relatively stiff proximal end region of the catheter advancement element 300 and the very flexible distal end region 346 of the catheter advancement element 300 generates forces in the catheter 200 differently than, for example, a guidewire or microcatheter would. The stored forces or forward load on the aspiration catheter 200 can be released upon proximal withdrawal of the catheter advancement element 300 through the lumen 223 of the catheter 200. Release of forces or forward load causes the aspiration catheter 200 to automatically drive distally towards the embolus 115. The catheter 200 can be actively pulled back during withdrawal of the catheter advancement element 300 to prevent this distal travel of the catheter 200 distal end. In an alternative method, the catheter 200 proximal end is held fixed during withdrawal of the catheter advancement element 300 allowing the catheter 200 to ride the forward momentum towards the embolus 115. For example, the aspiration catheter 200 may be positioned a distance proximal to the proximal face of the embolus 115, such as within the soft clot material. The aspiration catheter 200 can be positioned at or distal to the angiographic limit of contrast 120. The aspiration catheter 200 can be positioned tip-to-tip with the catheter advancement element 300 prior to removal of the catheter advancement element. The aspiration catheter 200 can also be positioned a distance proximal to the tip of the catheter advancement element 300. The distance proximal can vary between a few millimeters to a few centimeters depending on the user preference or the tortuosity of the vasculature and the potential energy of the catheter system prior to withdrawal of the catheter advancement element. The catheter 200 can be allowed to ride the momentum of release upon withdrawal of the catheter advancement element 300 to seat or nest the distal end 215 of the catheter 200 against the proximal face of the embolus 115. Allowing the aspiration catheter 200 to ride the momentum of the release results in the distal end 215 of the catheter 200 nesting with the proximal face of the embolus 115 in a natural and automatic manner without any external force applied by a user to advance the catheter 200. The act of proximal withdrawal of the catheter advancement element 300 can cause the aspiration catheter 200 to travel distally, in some instances multi-centimeter distances, closer to the embolus 115 without any distal force needing be applied by a user on the aspiration catheter 200 (although some additional manual force may be provided, if desired). The force of this catheter movement is relatively low such that the aspiration catheter 200 can naturally find the proximal face of the embolus 115 safely and with good contact between the catheter 200 and the embolus 115, but without the catheter 200 (or anything else) crossing the embolus 115.

First-pass aspiration is more likely when the catheter 200 is allowed to ride forward and seat during withdrawal of the catheter advancement element 300. This natural seating with the embolus 115 occurs passively or automatically without the surgeon needing to know exactly where the proximal face of the embolus 115 is. The fresh, soft clot material 125 that accumulates at the proximal face of the embolus 115 is typically unorganized and not dense enough to prevent the aspiration catheter 200 from traversing through it. Additionally, the aspiration catheter 200 has a soft distal end 215 and the distal force driving the catheter 200 forward is low enough that the motion does not damage the vessel nor does it cause the catheter 200 to cross the embolus 115. A surgeon may also apply a small amount of force to encourage further distal travel of the catheter 200 toward the embolus 115 allowing for the natural seating with the embolus 115 to occur. Naturally seating on, against, or around the embolus can provide for a less traumatic advancement of the catheter 200 than relying solely on manually advancing the catheter 200 distally. In some implementations, the user may want a slight compression of the embolus 115 against the distal end 215 of the catheter 200 as it travels distally.

Riding the forward momentum also assists surgeons in selecting the appropriate catheter size. The catheter 200 can ride the forward momentum until it runs into organized or more dense embolus 115 or until it reaches a bifurcation, or a smaller vessel where it cannot pass. The natural advancement of the catheter 200 can find the optimum embolic aspiration site in an atraumatic manner without a user applying distally-directed force and without needing to advance the catheter 200 over the catheter advancement element 300. In addition, all of this can be performed without any component (e.g., guidewire or catheter advancement element or catheter) crossing the embolus. If the catheter distal end does not reach the occlusion site either with or without the catheter advancement element, the first catheter can be fixed in place, the catheter advancement element removed and a smaller catheter can be inserted to the occlusion site.

The occlusive material can be captured at, within, or through the distal end 215 of the aspiration catheter 200 while applying aspiration from an external aspiration source, for example, an aspiration source coupled to the RHV 434 of the base sheath 400. The occlusive material can also be captured during proximal withdrawal of the catheter advancement element 300. As mentioned above, the tubular portion of the catheter advancement element can have an outer diameter that forms a relatively snug tolerance with the aspiration catheter. A difference between the outer diameter at a snug point of the tubular portion and the inner diameter of the lumen at the distal end of the distal, catheter portion can be no more than about 0.015", for example, between about 0.003" and 0.015". This relatively large outer diameter of the catheter advancement element 300 snug region in combination with a relatively small inner diameter of the lumen 368 of the catheter advancement element 300, typically filled by the guidewire and/or liquid, results in the catheter advancement element 300 being relatively occlusive to the aspiration catheter 200 when positioned in its lumen 223 and forming a closed system. The catheter advancement element 300 is generally removed before any external aspiration is applied through the lumen 223 of the aspiration catheter 200. As the distal end region 346 of the occlusive catheter advancement element 300 is withdrawn through the lumen 223 of the aspiration catheter 200, particularly when withdrawn quickly, a vacuum is automatically created at the distal end of the catheter 200. This automatic creation of pressure is internal to the catheter system and occurs without any vacuum applied proximally such as at the RHV with an aspiration device. The catheter advancement element acts like a plunger in a syringe. For example, the catheter advancement element 300 can be positioned at its distal-most position relative to an embolus 115 and the aspiration catheter 200 can be advanced to a location at or beyond the angiographic limit of contrast 120, the catheter advancement element 300 can be withdrawn proximally back into the lumen 223 of the aspiration catheter 200. The snug region between the two tubes also moves proximally. The proximal motion of the catheter advancement element 300 relative to the aspiration catheter 200 can, like the plunger in a syringe, automatically create a suction force at the distal opening of the aspiration catheter 200 without any external aspiration being applied at the proximal end of the catheter system.

The act of withdrawing the catheter advancement element 300 relative to the catheter 200 can simultaneously drive the catheter 200 distally towards the embolus 115 and automatically create a vacuum at the distal end of the catheter 200 to immediately start capturing or pulling embolic material towards the lumen 223 of the catheter 200 as the catheter 200 is urged toward and seating against the embolus 115. Each improves the success of first-pass embolectomy. The vacuum automatically generated may or may not be sufficient to aspirate the entire embolus 115 into the lumen 223 of the aspiration catheter 200. In some implementations, the automatic generation of vacuum within the catheter 200 caused by withdrawal of the catheter advancement element 300 relative to the catheter 200 can cause at least a portion of the embolus to be pulled into the lumen 223 of the catheter 200 before an aspiration source is connected to the proximal hemostasis valve 434 of the base sheath 400.

Figure 12:
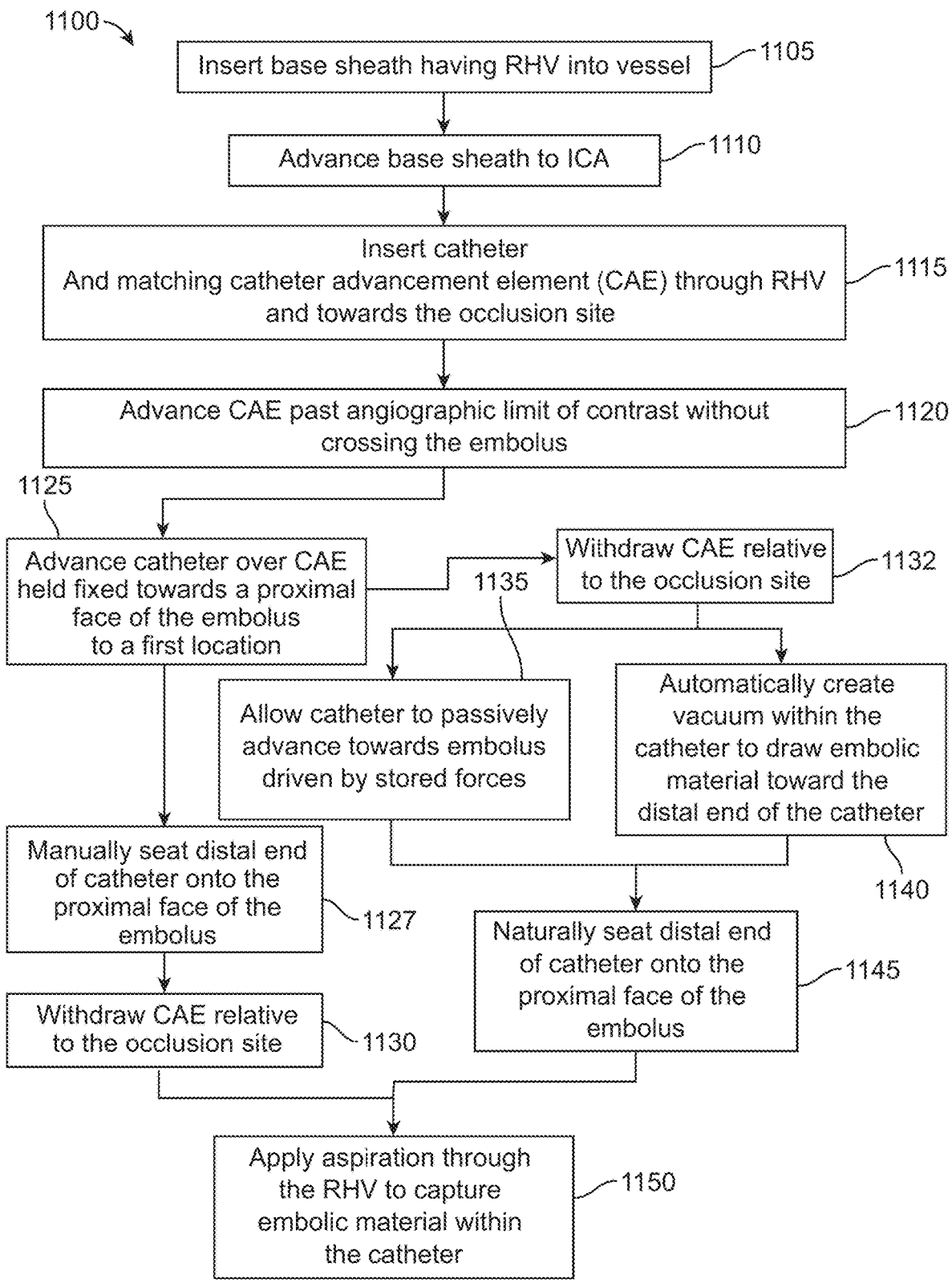
FIG. 12 is a flow diagram of an interrelated implementation of a method of aspiration embolectomy in a cerebral vessel.

FIG. 12 is a flow diagram showing another method 1100 of using the catheter systems described herein to remove an embolus in a cerebral vessel of a patient. A base sheath 400 is inserted into a vessel (Box 1105). The vessel can be the common femoral artery and the base sheath 400 may be an 8 Fr long sheath inserted over a guidewire. The base sheath 400 is advanced until a distal end region 408 of the base sheath is positioned distal to the common carotid artery such as within the ICA (Box 1110). FIG. 15A also illustrates the base sheath 400 advanced until a distal end region of the base sheath is positioned within the ICA. The base sheath 400 may be back bled and placed on continuous flush with an RHV. The base sheath 400 can be advanced over a guidewire until its distal tip is in the mid- to lower cervical ICA. The aspiration catheter 200 (which may be preloaded with matching catheter advancement element (CAE) 300) is inserted into the base sheath 400 (Box 1115) and advanced out through the distal end of the base sheath 400. The catheter 200 and catheter advancement element 300 can be inserted as a unit or individually in a nested fashion. The aspiration catheter may be an 0.070" (1.778 mm) or an 0.088" (2.235 mm) aspiration catheter having a suitably sized catheter advancement element positioned within its lumen so that a snug point between the two components is created. The catheter advancement element 300 and the aspiration catheter 200 may be advanced together towards the occlusion site 105. The assembled system of device may have the tapered distal end region of the catheter advancement element extending distal to the distal end of the catheter. FIG. 15A shows an aspiration catheter 200 having a catheter advancement element with a tapered distal end region 346 extending distal to the distal end of the catheter 200 advanced out the distal end of the base sheath 400 positioned within the ICA. The assembled system of device can be advanced together towards the occlusion site in the cerebral vessel of the patient. The occlusion site may be visible on angiogram and can include an angiographic limit of contrast and an embolus downstream of the angiographic limit of contrast. FIG. 15A also shows the embolus 115 downstream of the angiographic limit of contrast 120 within the M1. The catheter advancement element 300 is advanced to a target location that is past the angiographic contrast limit 120 (Box 1120) without crossing the embolus. FIG. 15B illustrates the distal end region 346 of the catheter advancement element 300 advanced past the angiographic contrast limit 120 and through the soft clot material 125 upstream of the embolus 115. The distal-most end 325 of the catheter advancement element 300 passively probes to find and/or create space beside the embolus 115 or between at least a portion of the embolus 115 and the vessel wall. This technique of passive probing to find and/or create a space is referred to as the Hand Under the Pillow (HUP) technique. The catheter may be advanced to position the distal end of the catheter at a treatment site located past the angiographic limit of contrast and aspiration applied to the catheter. The catheter advancement element 300 can be held fixed relative to the occlusion site 105 and the aspiration catheter 200 advanced, manually or automatically, over it towards a proximal face of the embolus to a first location (Box 1125). The first location may be a distance away from the proximal face of the embolus 115. The distal end of the catheter 200 can be seated onto the proximal face of the embolus (Box 1127) and then withdraw the catheter advancement element 300 relative to the occlusion site 105 (Box 1130). The withdrawal of the catheter advancement element 300 can cause the catheter to passively advance into the embolus or to compress the embolus.

In other implementations, the catheter advancement element 300 is withdrawn relative to the occlusion site 105 (Box 1132) and the aspiration catheter 200 is allowed to advance passively towards the embolus 115 driven by stored forces in the catheter system 150 (Box 1135). The aspiration catheter 200 may advance passively, with or without any user force being applied. Withdrawal of the catheter advancement element 300 so that the distal end region 346 enters the lumen 223 of the aspiration catheter 200 can simultaneously create an internal vacuum within a region of the aspiration catheter lumen 223 causing embolic material to be drawn toward or into the distal end 215 of the catheter 200 (Box 1140). The vacuum can be created automatically without any external aspiration being applied at the RHV of the base sheath. The distal end of the catheter can naturally seat with the proximal face of the embolus (Box 1145). The internal vacuum may also facilitate distal advancement of the catheter 200 towards the embolus 115. FIG. 15C illustrates the catheter advancement element 300 withdrawn proximally (arrow P) relative to the catheter 200 so that the distal marker 344a is now inside the lumen of the catheter 200 a distance proximal to the distal end 215 of the catheter 200. The catheter 200, in turn, has passively advanced (arrow D) into the embolus 115 so that at least a portion of the embolus 115 is inside the lumen of the catheter 200. In some implementations, the distal end 215 of the aspiration catheter 200 is urged against the embolus 115 compressing it by the release of stored forces in the catheter 200. Once the distal end 215 of the aspiration catheter 200 is in position (e.g., at or against the face of the embolus) and the catheter advancement element 300 removed from the lumen of the catheter, the RHV on the base sheath 400 can be sealed and external aspiration initiated through the same RHV such as via a side-arm (Box 1150). The embolus 115 can be aspirated from the patient through the catheter 200 via the aspiration pressure alone. FIG. 15D illustrates the embolus 115 inside the catheter 200 after delivering aspiration pressure through the system. Alternatively, the catheter 200 having the embolus corked at the distal opening of the catheter can be slowly withdrawn, for example towards a lumen of a larger bore catheter and/or the base sheath, as aspiration is applied to effect embolus removal.

Figure 13:
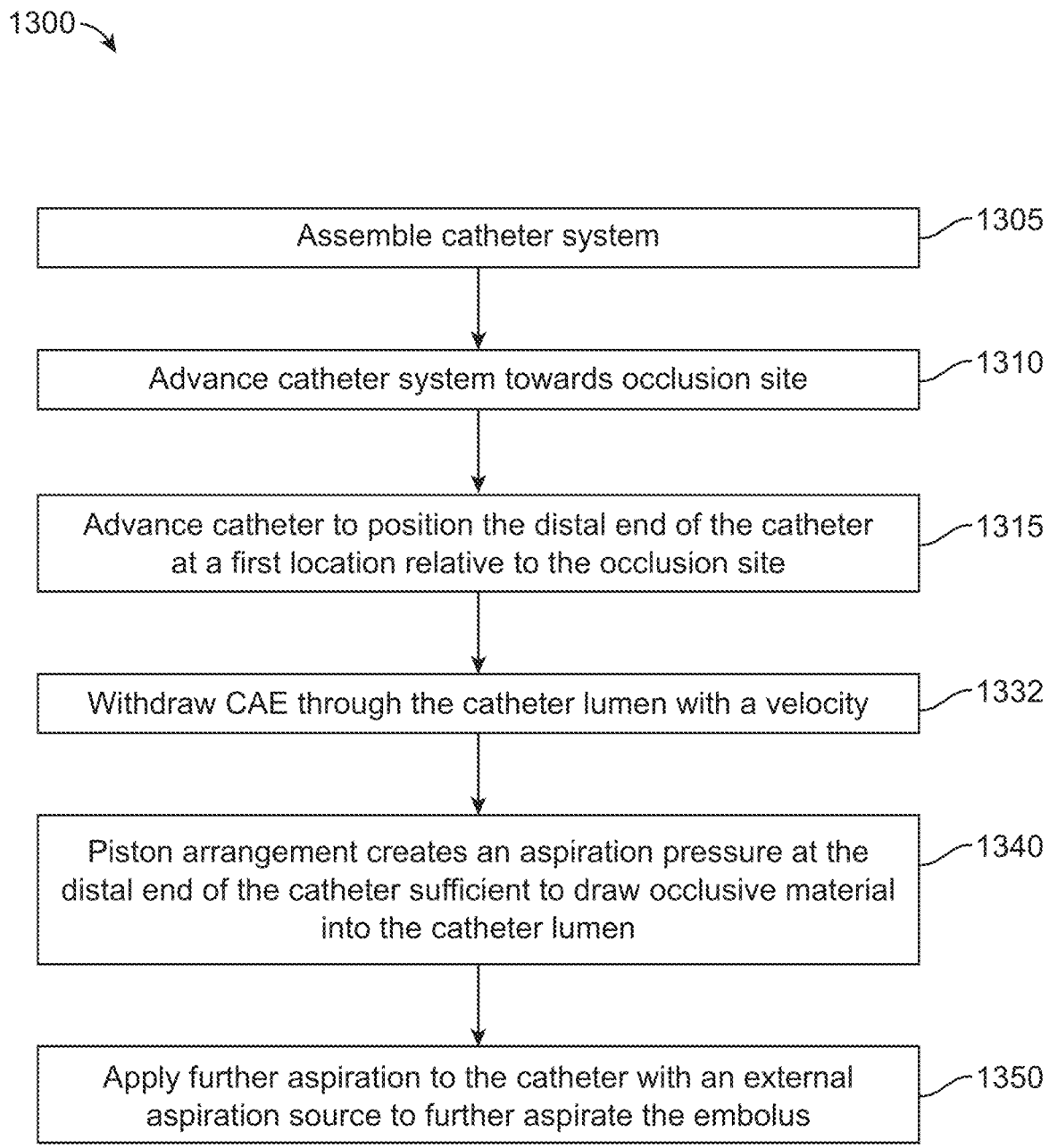
FIG. 13 is a flow diagram of an interrelated implementation of a method of aspiration embolectomy in a cerebral vessel.

FIG. 13 is a flow diagram showing another method 1300 of using the catheter systems described herein to perform aspiration-only embolectomy. A base sheath 400 of the catheter system 100 can be advanced from a femoral access site to the level of the carotid artery and contrast can be injected through the catheter system 100 to visualize the occlusion site 105 by angiogram (box 1015). The catheter system 150 can be assembled so that the tapered distal end region 346 of the catheter advancement element 300 extends distal to the distal end 215 of the aspiration catheter 200 (Box 1305). The catheter advancement element can substantially fill the lumen 223 of the catheter 200 along a length to create a piston arrangement. In preferred implementations, the length to create the piston arrangement is at least about 10 cm of the catheter length. The length can be about 4 mm to about 75 cm. The assembled catheter system 150 can be advanced together towards an occlusion site in a cerebral vessel of a patient (Box 1310). The occlusion site 105 can include occlusive material lodged in the cerebral vessel, which may include embolus 115 and soft clot material 125 upstream of the embolus. The tapered distal end region of the catheter advancement element can be positioned within occlusive material at the occlusion site. The catheter can be advanced to position the distal end of the catheter at a first location proximal to the occlusion site (Box 1315). A syringe may be coupled to the luer 364 of the catheter advancement element prior to its withdrawal from the catheter lumen. The syringe closes the lumen 368 and thus, the system thereby maximizing the piston effect upon withdrawal. The catheter advancement element 300 can be withdrawn through the catheter lumen (Box 1332). The catheter advancement element 300 can be withdrawn with a velocity, such as at a velocity of about 4 cm per second up to about 165 cm per second, or at a velocity of about 8 cm per second up to about 75 cm per second, that the piston arrangement creates an aspiration pressure at the distal end region of the catheter sufficient to draw occlusive material into the catheter lumen (Box 1340). The withdrawal step can be performed manually or automatically. Further aspiration can be applied to the catheter with an external aspiration source to further aspirate the embolus (1350).

FIG. 14 is a flow diagram of an interrelated method 1400 of treating a cerebral vessel of a patient. A system of devices having a catheter and a catheter advancement element CAE can be assembled where the catheter advancement element substantially fills the catheter lumen along a length to create a piston arrangement (Box 1405). The length to create the piston arrangement can be at least about 10 cm of the catheter length. The catheter system can be advanced towards an occlusion site (Box 1410). The occlusion site can be in a cerebral vessel of a patient that is visible on angiogram. The tapered distal end region of the catheter advancement element can be positioned within occlusive material at the occlusion site (Box 1415). A syringe may be coupled to the luer of the catheter advancement element prior to its withdrawal from the catheter lumen to maximize the piston effect upon withdrawal. The catheter advancement element can be withdrawn through the catheter lumen (Box 1420). The piston arrangement can create an aspiration pressure at the distal end of the catheter sufficient to draw a portion of the occlusive material into the catheter lumen (Box 1425). The occlusive material can include dense embolus and less dense clot. Withdrawing the catheter advancement element can cause the catheter to advance and seat the distal end of the catheter against a proximal face of the embolus. The withdrawing can cause the catheter to move in a distal direction towards the occlusion site driven by the release of forces stored in the system of devices during delivery. A combination of the aspiration pressure from withdrawing the catheter advancement element and the distal motion of the catheter can cause the portion of the occlusive material to enter the catheter lumen. The withdrawal step can be performed manually or automatically. Further aspiration can be applied to the catheter with an external aspiration source following the withdrawal of the catheter advancement element from the catheter lumen. The external aspiration source can be applied through an RHV of a base sheath through which the system of devices is positioned. The catheter advancement element can be removed before the distal end of the catheter is at a face of the embolus.

The initial aspiration of occlusive material during withdrawal of the catheter advancement element can be described as facilitated engagement as the withdrawal facilitates improved embolus engagement with the catheter. Further aspiration from an external aspiration source may be applied to further aspirate the embolus. The distal end of the catheter 200 can be placed close to the embolus in the occlusive material for efficient aspiration. Aspiration without the distal end of the catheter 200 against the embolus can cause vessel collapse or "suck down" which can prevent successful embolus aspiration. An outer diameter of the catheter 200 can be sized close to a vessel size to maximize efficiency of aspiration. It may be desirable to use a nested system of successively larger catheter sizes to create a family of aspiration catheters all working from a single point of operation via the single RHV. The nested catheter system allows the user to attempt to reach the occlusion with a first larger bore catheter and then if the larger bore catheter does not reach the treatment site, the smaller bore catheter can be advanced for aspiration. An example of a system of nested catheters is described in U.S. Patent Publication No. 2020/0289136, filed on Jun. 2, 2020, which is incorporated herein by reference in its entirety.

The velocity at which the catheter advancement element 300 is withdrawn from the catheter lumen can be constant. The velocity of the catheter advancement element 300 withdrawal can change so that the catheter advancement element 300 accelerates through the catheter lumen. For example, the catheter advancement element 300 can be withdrawn a first distance through the catheter lumen at an initial velocity and accelerate to a second velocity along a second distance. The second velocity can be greater than the first velocity. The change in velocity can be small along the first distance and become greater along the second distance. For example, the initial withdrawal of the catheter advancement element 300 can be slow and steady. The acceleration can initially be at a high rate or at a low rate, but soon approaches zero once the initial velocity is achieved over the first distance. Once the catheter advancement element 300 is withdrawn the first distance, the catheter advancement element 300 can be withdrawn very quickly the second distance. The acceleration can be at a high rate or at a low rate before it approaches zero once the second velocity is achieved over the second distance. The acceleration of the catheter advancement element withdrawal over the second distance can be constant. The acceleration of the catheter advancement element withdrawal over the second distance can also change. The rate of change in acceleration, such as an increase in acceleration with increased distance of withdrawal of the catheter advancement element 300, can provide an additional impact force or jerk on the occlusive material. This method differs from a typical practice of removing coaxial system elements slowly and in a manner so as not to disrupt the position of the other system elements.

Withdrawing an embolus corked at the distal opening of the catheter back to the distal opening of the guide sheath can increase the risk of fragmentation and embolization depending on the distance it must be withdrawn before being fully encapsulated within a lumen. Thus, it may be desirable to use a nested system of successively larger catheter sizes to create a family of aspiration catheters all working from a single point of operation via the single RHV. This allows for the smallest bore catheter advanced most distal to withdraw only a short distance into a larger bore catheter, which in turn can suction the embolus en toto, or, if needed, be withdrawn another short distance into a larger bore catheter that can suction the embolus from the body. The likelihood of the captured clot from fragmenting is thereby reduced and the likelihood of the clot being aspirated en toto is increased.

Materials

One or more components of the catheters described herein may include or be made from a variety of materials including one or more of a metal, metal alloy, polymer, a metal-polymer composite, ceramics, hydrophilic polymers, polyacrylamide, polyethers, polyamides, polyethylenes, polyurethanes, copolymers thereof, polyvinyl chloride (PVC), PEO, PEO-impregnated polyurethanes such as Hydrothane, Tecophilic polyurethane, Tecothane, PEO soft segmented polyurethane blended with Tecoflex, thermoplastic starch, PVP, and combinations thereof, and the like, or other suitable materials.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

Inner liner materials of the catheters described herein can include low friction polymers such as PTFE (polytetrafluoroethylene) or FEP (fluorinated ethylene propylene), PTFE with polyurethane layer (Tecoflex). Reinforcement layer materials of the catheters described herein can be incorporated to provide mechanical integrity for applying torque and/or to prevent flattening or kinking such as metals including stainless steel, Nitinol, Nitinol braid, helical ribbon, helical wire, cut stainless steel, or the like, or stiff polymers such as PEEK. Reinforcement fiber materials of the catheters described herein can include various high tenacity polymers like Kevlar, polyester, meta-para-aramide, PEEK, single fiber, multi-fiber bundles, high tensile strength polymers, metals, or alloys, and the like. Outer jacket materials of the catheters described herein can provide mechanical integrity and can be contracted of a variety of materials such as polyethylene, polyurethane, PEBAX, nylon, Tecothane, and the like. Other coating materials of the catheters described herein include paralene, Teflon, silicone, polyimide-polytetrafluoroethylene, and the like. The inner liner may further include different surface finishes, such as dimples, bumps, ridges, troughs. The surface finishes may be randomly disposed, linearly disposed, spirally disposed, or otherwise disposed using a specific pattern along the length of the catheter. It is further contemplated that the inner liner may include a mixture of different surface finishes, for example, one section may have dimples, another section may have troughs, etc. Additionally, the surface finish may be incorporated along the entire length of the catheter or only in sections of the catheter. It is also contemplated that the inner liner may further include an electrosprayed layer, whereby materials could be incorporated into the inner liner. Examples of materials can include low friction materials as described above. Alternatively, the electrosprayed or electrospun layer may incorporate a beneficial agent that becomes free from the coating when exposed to blood, or to compression from a clot, for example, the beneficial agent may be a tissue plasminogen activator (tPA) or heparin encased in alginate.

Implementations describe catheters and delivery systems and methods to deliver catheters to target anatomies. However, while some implementations are described with specific regard to delivering catheters to a target vessel of a neurovascular anatomy such as a cerebral vessel, the implementations are not so limited and certain implementations may also be applicable to other uses. For example, the catheters can be adapted for delivery to different neuroanatomies, such as subclavian, vertebral, carotid vessels as well as to the coronary anatomy or peripheral vascular anatomy, to name only a few possible applications. Although the systems described herein are described as being useful for treating a particular condition or pathology, that the condition or pathology being treated may vary and are not intended to be limiting.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the catheters and/or delivery systems to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

The catheter system disclosed herein may be packaged together in a single package, where the catheters and catheter advancement element are packaged in a coil tube. The finished package would be sterilized using sterilization methods such as Ethylene oxide or radiation and labeled and boxed. Instructions for use may also be provided in-box or through an internet link printed on the label.

What is claimed is:

1. A method of treating a cerebral vessel of a patient, the method comprising:
    assembling a system of devices, the assembled system of devices comprising:
        an outer catheter having a catheter lumen and a distal end; and
        an inner catheter extending through the catheter lumen comprising a non-expandable flexible elongate body having a tapered distal end region that extends distal to the distal end of the outer catheter, and wherein the non-expandable flexible elongate body substantially fills the catheter lumen along a length to create a piston arrangement and wherein the tapered distal end region tapers from a first outer diameter to a second outer diameter, the second outer diameter located distal to and being smaller than the first outer diameter;
    advancing the outer catheter towards an occlusion site having occlusive material lodged in a cerebral vessel of a patient to position the distal end of the outer catheter at a first location relative to the occlusion site;
    withdrawing the inner catheter from within the catheter lumen with a velocity;
    creating an aspiration pressure at the distal end of the outer catheter with the piston arrangement, the aspiration pressure sufficient to draw the occlusive material into the catheter lumen; and
    applying further aspiration to the outer catheter with an external aspiration source after removal of the inner catheter from the catheter lumen to further aspirate the occlusive material.

2. The method of claim 1, wherein the occlusive material comprises embolus, and wherein the step of withdrawing the inner catheter causes the outer catheter to advance and seat the distal end of the outer catheter against a proximal face of the embolus.

3. The method of claim 1, wherein the occlusive material comprises embolus, and further comprising removing the inner catheter before the distal end of the outer catheter is at the embolus.

4. The method of claim 1, wherein withdrawing the inner catheter from the catheter lumen comprises capturing the occlusive material at, within, or through the distal end of the outer catheter while removing the inner catheter.

5. The method of claim 1, wherein the step of applying further aspiration to the outer catheter is performed through a rotating hemostatic valve of a base sheath through which the system of devices is positioned.

6. The method of claim 1, wherein a clearance between the inner catheter and the outer catheter lumen is less than about 0.006" along the length to create the piston arrangement.

7. The method of claim 1, wherein the length to create the piston arrangement is at least 10 cm of a length of the catheter lumen of the outer catheter.

8. The method of claim 1, wherein the tapered distal end region of the inner catheter tapers along a distance that is between 5 mm and 40 mm.

9. The method of claim 1, wherein the first outer diameter is at least 1.5 times the second outer diameter.

10. The method of claim 1, wherein the step of withdrawing the inner catheter causes the outer catheter to move in a distal direction towards the occlusion site driven by release of forces stored in the system of devices during delivery.

11. The method of claim 10, wherein a combination of the aspiration pressure from withdrawing the inner catheter and distal motion of the outer catheter causes a portion of the occlusive material to enter the catheter lumen.

12. The method of claim 1, further comprising advancing the assembled system of devices together towards the occlusion site.

13. The method of claim 12, wherein advancing the assembled system of devices together towards the occlusion site comprises advancing the assembled system of devices together without a guidewire extending through the inner catheter.

14. The method of claim 12, wherein advancing the assembled system of devices together towards the occlusion site comprises advancing the assembled system of devices together over a guidewire.

15. The method of claim 12, wherein advancing the assembled system of devices together towards the occlusion site comprises advancing the assembled system of devices together with a guidewire positioned within the inner catheter so a distal end of the guidewire is positioned proximal of a distal end of the inner catheter.

16. The method of claim 12, further comprising visualizing the assembled system of devices using fluoroscopy; adjusting relative positions of the inner catheter and/or the outer catheter; and resuming advancing of the assembled system of devices while in an adjusted relative position.

17. The method of claim 12, further comprising adjusting the assembled system of device during advancing the assembled system of device to achieve a tip-to-taper position, wherein the tip-to-taper position comprises the distal end of the outer catheter being aligned near a proximal end of the tapered distal end region of the inner catheter.

18. The method of claim 17, wherein the inner catheter comprises a first radiopaque marker identifying a proximal end of the tapered distal end region of the inner catheter, and wherein the outer catheter comprises a second radiopaque marker identifying the distal end of the outer catheter, wherein the first and second radiopaque markers aid in achieving the tip-to-taper position.

19. A method of treating a cerebral vessel of a patient, the method comprising:

assembling a system of devices in an advancement configuration, the assembled system of devices comprising:
  an outer catheter having a catheter lumen and a distal end; and
  an inner catheter extending through the catheter lumen, wherein a tapered distal end region of the inner catheter extends distal to the distal end of the outer catheter when assembled in the advancement configuration, and wherein the inner catheter substantially fills the catheter lumen along a length to create a piston arrangement; and advancing the assembled system of devices in the advancement configuration so that the distal end of the outer catheter is positioned near an occlusion site in a cerebral vessel of a patient visible on angiogram;

positioning the tapered distal end region of the inner catheter within occlusive material at the occlusion site;

withdrawing the inner catheter through the catheter lumen causing the piston arrangement to create an aspiration pressure at the distal end of the outer catheter sufficient to draw a portion of the occlusive material into the catheter lumen; and applying aspiration to the catheter lumen with an external aspiration source after removal of the inner catheter from the catheter lumen to further aspirate occlusive material.

20. The method of claim 19, wherein the step of withdrawing the inner catheter causes the distal end of the outer catheter to move in a distal direction towards the occlusion site driven by release of forces stored in the system of devices during delivery.

21. The method of claim 19, wherein a combination of the aspiration pressure from withdrawing the inner catheter and distal motion of the distal end of the outer catheter causes the portion of the occlusive material to enter the catheter lumen.

22. The method of claim 19, wherein the step of applying further aspiration to the outer catheter is performed through a rotating hemostatic valve of a base sheath through which the system of devices is positioned.

23. The method of claim 19, wherein a clearance between the inner catheter and the catheter lumen is less than about 0.006" along the length to create the piston arrangement.

24. The method of claim 19, wherein the length to create the piston arrangement is at least 10 cm of a length of the catheter lumen of the outer catheter.

25. The method of claim 19, wherein the occlusive material comprises embolus.

26. The method of claim 25, wherein the step of withdrawing the inner catheter causes the distal end of the outer catheter to advance and seat against a proximal face of the embolus.

27. The method of claim 25, wherein the step of withdrawing the inner catheter is performed before the distal end of the outer catheter is positioned at a face of the embolus.

* * * * *